United States Patent
Mizuki et al.

(10) Patent No.: US 9,963,429 B2
(45) Date of Patent: May 8, 2018

(54) CARBAZOLE DERIVATIVE, MATERIAL FOR ORGANIC ELECTROLUMINESCENT ELEMENT WHICH COMPRISES SAME, AND ORGANIC ELECTROLUMINESCENT ELEMENT AND ELECTRONIC DEVICE EACH MANUFACTURED USING SAME

(71) Applicant: IDEMITSU KOSAN CO., LTD., Chiyoda-ku (JP)

(72) Inventors: Yumiko Mizuki, Basel (CH); Hirokatsu Ito, Ichihara (JP); Tasuku Haketa, Chiba (JP); Tomoharu Hayama, Utsunomiya (JP); Kazuki Nishimura, Sodegaura (JP); Masahiro Kawamura, Chiba (JP); Mitsuru Shibata, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 128 days.

(21) Appl. No.: 14/911,352

(22) PCT Filed: Sep. 1, 2014

(86) PCT No.: PCT/JP2014/072951
§ 371 (c)(1),
(2) Date: Feb. 10, 2016

(87) PCT Pub. No.: WO2015/033894
PCT Pub. Date: Mar. 12, 2015

(65) Prior Publication Data
US 2016/0204361 A1    Jul. 14, 2016

(30) Foreign Application Priority Data
Sep. 4, 2013 (JP) .................................. 2013-183537

(51) Int. Cl.
*H01L 51/00* (2006.01)
*C07D 209/88* (2006.01)
(Continued)

(52) U.S. Cl.
CPC ......... *C07D 209/86* (2013.01); *C07D 209/88* (2013.01); *C07D 403/14* (2013.01);
(Continued)

(58) Field of Classification Search
None
See application file for complete search history.

(56) References Cited

U.S. PATENT DOCUMENTS

2012/0205636 A1*  8/2012  Kim .................. C09K 11/06
                                                            257/40
2012/0223276 A1   9/2012  Parham et al.
(Continued)

FOREIGN PATENT DOCUMENTS

CN    101062929 A    10/2007
CN    101126020 A    2/2008
(Continued)

OTHER PUBLICATIONS

Machine-generated English-language translation of KR 2013-0093207 A.*
(Continued)

*Primary Examiner* — Vu A Nguyen
(74) *Attorney, Agent, or Firm* — Oblon, McClelland, Maier & Neustadt, L.L.P.

(57) ABSTRACT

A novel carbazole derivative represented by formula (1) in which two or more groups each having a specific structure, such as a carbazolyl group, are bonded to two or more of 2-, 3- and 4-positions of the carbazole derivative is useful as a material for organic electroluminescence devices. A material (Continued)

for organic electroluminescence devices including the carbazole derivative, an organic electroluminescence device employing the carbazole derivative, and an electronic equipment are described.

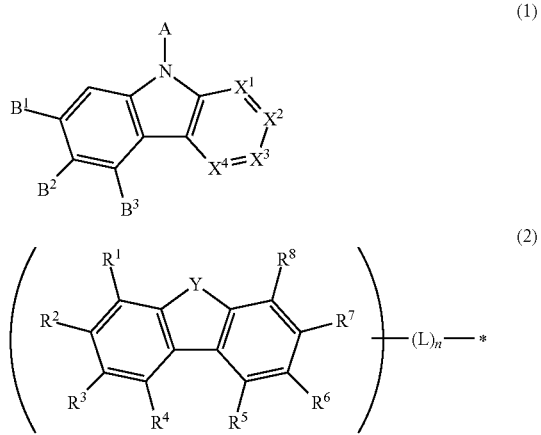

wherein at least two selected from $B^1$ to $B^3$ are represented by formula (2) and A, $X^1$ to $X^4$, L, n, Y, and $R^1$ to $R^8$ are as defined in claim 1.

24 Claims, 1 Drawing Sheet

(51) Int. Cl.
C07D 209/86 (2006.01)
C09K 11/02 (2006.01)
C09K 11/06 (2006.01)
C07D 403/14 (2006.01)
H01L 51/50 (2006.01)

(52) U.S. Cl.
CPC ............ *C09K 11/025* (2013.01); *C09K 11/06* (2013.01); *H01L 51/0054* (2013.01); *H01L 51/0067* (2013.01); *H01L 51/0072* (2013.01); C09K 2211/1007 (2013.01); C09K 2211/1029 (2013.01); C09K 2211/185 (2013.01); H01L 51/0059 (2013.01); H01L 51/0085 (2013.01); H01L 51/5012 (2013.01); H01L 51/5016 (2013.01); H01L 51/5056 (2013.01); H01L 51/5064 (2013.01)

(56) References Cited

U.S. PATENT DOCUMENTS

2013/0306962 A1    11/2013    Yamamoto et al.
2014/0231794 A1*    8/2014    Iwakuma ............ C07D 405/14
                                                                    257/40

FOREIGN PATENT DOCUMENTS

| KR | 10-2013-0093207 A |   | 8/2013 |   |
| KR |     20130093207 A | * | 8/2013 | ............ H01L 51/50 |
| WO |     2011/049325 A2 |   | 4/2011 |   |
| WO |     2011/057706 A2 |   | 5/2011 |   |
| WO |     2012/108879 A1 |   | 8/2012 |   |
| WO |     2014/021569 A1 |   | 2/2014 |   |

OTHER PUBLICATIONS

Doctoral Dissertation by Tissa Sajoto (May 2008, USC).*
Kazuyuki Moriwaki, et al., "Photochemical Reaction of 1,3,5-Tris(diphenylamino)benzene" Journal of Photopolymer Science and Technology, 1999, vol. 12, No. 5, pp. 777-780 (2 pages).
International Search Report dated Oct. 21, 2014 for PCT/JP2014/072951 filed on Sep. 1, 2014.
Office Action as received in the corresponding Japanese Patent Application No. JP2015-535462 dated Jan. 9, 2018.

* cited by examiner

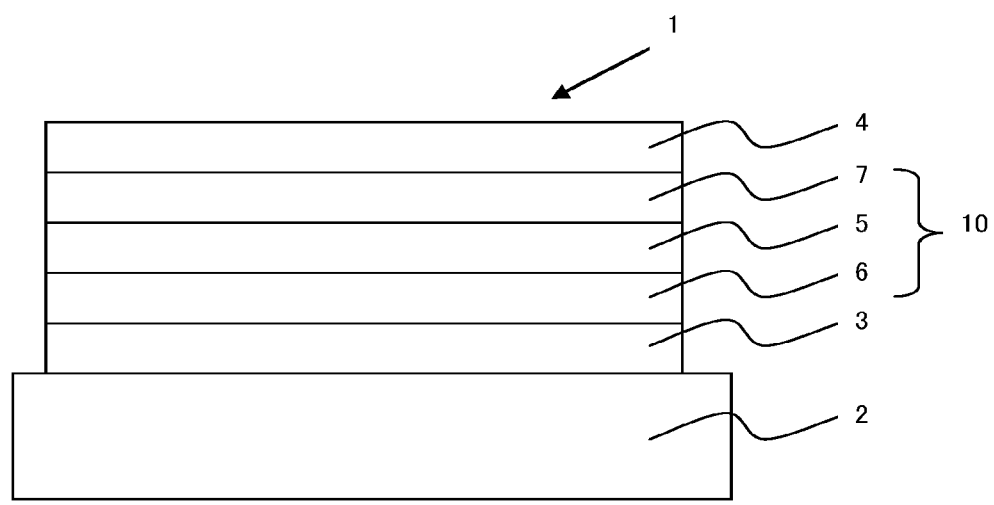

CARBAZOLE DERIVATIVE, MATERIAL FOR ORGANIC ELECTROLUMINESCENT ELEMENT WHICH COMPRISES SAME, AND ORGANIC ELECTROLUMINESCENT ELEMENT AND ELECTRONIC DEVICE EACH MANUFACTURED USING SAME

TECHNICAL FIELD

The present invention relates to carbazole derivatives, materials for organic electroluminescence devices comprising the carbazole derivatives, and organic electroluminescence devices and electronic equipment each employing the carbazole derivatives.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, and blue colors has been made most actively, and the intensive research has been made to improve their properties.

A compound in which two carbazolyl groups are bonded to 1- and 3-positions of a carbazole is disclosed as a material for organic EL devices in Patent Literatures 1 and 2.

However, a novel material is still required to be developed in the field of organic EL device to further improve the device performance.

CITATION LIST

Patent Literature

Patent Literature 1: WO 2011/049325
Patent Literature 2: CN 101126020A

SUMMARY OF INVENTION

Technical Problem

The present invention has been made to solve the above problem and an object of the invention is to provide a new material useful as a material for organic EL devices.

Solution to Problem

As a result of extensive research in view of achieving the above object, the inventors have found that a carbazole derivative in which two or more groups each having a specific structure, such as a carbazolyl group, are bonded to two or more of 2-, 3- and 4-positions of the carbazole derivative is effective as a material for organic EL devices for improving device performance.

In an aspect of the present invention, a carbazole derivative described below is provided:

(1) a carbazole derivative represented by formula (1):

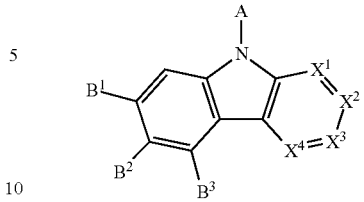

wherein:

A represents a substituted or unsubstituted aryl group having 6 to 60 ring carbon atoms or a substituted or unsubstituted heteroaryl group having 5 to 60 ring atoms;

$X^1$ represents N or CH;

$X^2$ to $X^4$ each represent N or CR;

R and $B^1$ to $B^3$ each independently represent a hydrogen atom or a substituent, wherein adjacent substituents may be bonded to each other to form a saturated or unsaturated ring structure and when more than one R occurs, groups R may be the same or different; and at least two selected from $B^1$ to $B^3$ are represented by formula (2):

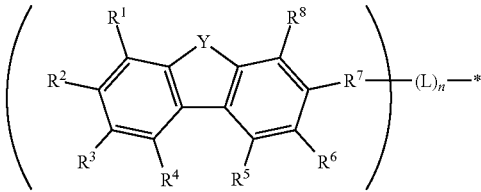

wherein

* represents a bonding site of $B^1$ to $B^3$ to the carbon atom shown in formula (1);

n is an integer of 0 to 4;

L represents a substituted or unsubstituted arylene group having 6 to 60 ring carbon atoms, a substituted or unsubstituted heteroarylene group having 5 to 60 ring atoms, or a substituted or unsubstituted alkylene group having 1 to 50 carbon atoms;

Y represents NZ, O, S, or CR'R";

$R^1$ to $R^8$, Z, R', and R" each independently represent a single bond, a hydrogen atom or a substituent, wherein adjacent substituents may be bonded to each other to form a saturated or unsaturated ring structure;

provided that when Y is NZ, $R^1$ and $R^8$ are hydrogen atoms; and one selected from $R^1$ to $R^8$, Z, R', and R" represents a single bond which bonds to L, wherein when n is 0, formula (2) bonds to formula (1) via a single bond, and when n is 2 or more, groups L may be the same or different and may be bonded to each other to form a saturated or unsaturated ring structure;

(2) a material for organic electroluminescence devices which comprises the carbazole derivative;

(3) an organic electroluminescence device which comprises an organic thin film layer between a cathode and an anode, wherein the organic thin film layer comprises one or more layers which comprise a light emitting layer and at least one layer of the organic thin film layer comprises the carbazole derivative;

(4) an electronic equipment which comprises the organic electroluminescence device; and (5) a carbazole derivative represented by formula (10):

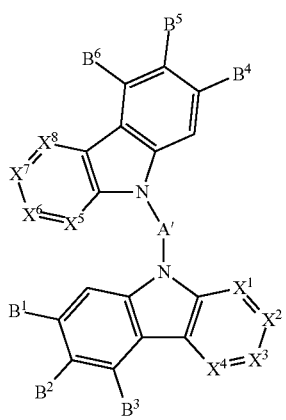

(10)

wherein:

A' represents a substituted or unsubstituted arylene group having 6 to 60 ring carbon atoms or a substituted or unsubstituted heteroarylene group having 5 to 60 ring atoms;

$X^1$ and $X^5$ each represent N or CH;

$X^2$ to $X^4$ and $X^6$ to $X^8$ each represent N or CR;

R and $B^1$ to $B^6$ each independently represent a hydrogen atom or a substituent, wherein adjacent substituents may be bonded to each other to form a saturated or unsaturated ring structure; and at least two selected from $B^1$ to $B^3$ are represented by formula (2):

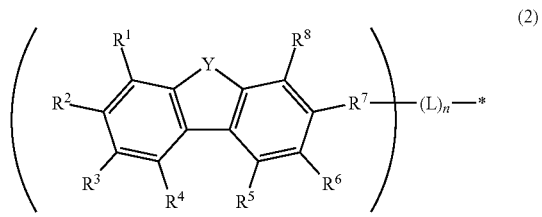

(2)

wherein:

\* represents a bonding site of $B^1$ to $B^3$ to the carbon atom shown in formula (10);

n is an integer of 0 to 4;

L represents a substituted or unsubstituted arylene group having 6 to 60 ring carbon atoms, a substituted or unsubstituted heteroarylene group having 5 to 60 ring atoms, or a substituted or unsubstituted alkylene group having 1 to 50 carbon atoms;

Y represents NZ, O, S, or CR'R";

$R^1$ to $R^8$, Z, R', and R" each independently represent a single bond, a hydrogen atom or a substituent, wherein adjacent substituents may be bonded to each other to form a saturated or unsaturated ring structure;

provided that when Y is NZ, $R^1$ and $R^8$ are hydrogen atoms; and one selected from $R^1$ to $R^8$, Z, R', and R" represents a single bond which bonds to L, wherein when n is 0, formula (2) bonds to formula (10) via a single bond, and when n is 2 or more, groups L may be the same or different and may be bonded to each other to form a saturated or unsaturated ring structure.

Advantageous Effects of Invention

By the present invention, a novel material useful as a material for organic EL devices and an organic EL device employing the material are provided.

BRIEF DESCRIPTION OF DRAWINGS

FIG. 1 is a schematic illustration of the structure of an organic EL device in an aspect of the present invention.

DESCRIPTION OF EMBODIMENTS

The term "a to b carbon atoms" referred to by "a substituted or unsubstituted group X having a to b carbon atoms" used herein is the number of carbon atoms of the unsubstituted group X and does not include any carbon atom in the substituent of the substituted group X.

When adjacent groups are bonded to each other to form a ring, any carbon atom of a group having a to b carbon atoms may be bonded to any carbon atom of another group having a to b carbon atoms.

The number of "ring carbon atoms" referred to herein means the number of the carbon atoms included in the atoms which are members forming the ring itself of a compound in which a series of atoms or molecules is bonded to form the ring, for example, a monocyclic compound, a fused ring compound, a cross-linked compound, a spiro ring compound, a carbocyclic compound, and a heterocyclic compound. If the ring has a substituent, the carbon atom in the substituent is not included in the ring carbon atom. The same applies to the number of "ring carbon atom" described below, unless otherwise noted.

The number of "ring atom" referred to herein means the number of the atoms which are members forming the ring itself of a compound in which a series of atoms or molecules is bonded to form the ring, for example, a monocyclic compound, a fused ring compound, a cross-linked compound, a spiro ring compound, a carbocyclic compound, and a heterocyclic compound. The atom not forming the ring, for example, hydrogen atom(s) for saturating the valence of the atom which forms the ring, and the atom in a substituent on the ring are not counted as the ring atom. The same applies to the number of "ring atoms" described below, unless otherwise noted.

The definition of "hydrogen atom" used herein includes isotopes different in the neutron numbers, i.e., light hydrogen (protium), heavy hydrogen (deuterium), and tritium.

The optional substituent referred to by "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth) acryloyl group; an epoxy group; and an oxetanyl group.

These groups may have a substituent selected from the above optional substituents.

Carbazole Derivative

The carbazole derivative in an aspect of the present invention is represented by formula (1):

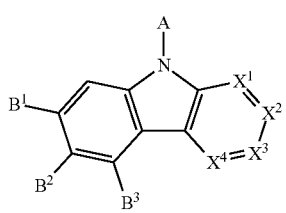

(1)

wherein:

A represents a substituted or unsubstituted aryl group having 6 to 60 ring carbon atoms or a substituted or unsubstituted heteroaryl group having 5 to 60 ring atoms;

$X^1$ represents N or CH;

$X^2$ to $X^4$ each represent N or CR;

R and $B^1$ to $B^3$ each independently represent a hydrogen atom or a substituent, wherein adjacent substituents may be bonded to each other to form a saturated or unsaturated ring structure and when more than one R occurs, groups R may be the same or different; and at least two selected from $B^1$ to $B^3$ are represented by formula (2):

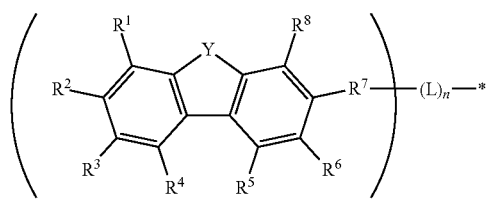

(2)

wherein

* represents a bonding site of $B^1$ to $B^3$ to the carbon atom shown in formula (1);

n is an integer of 0 to 4;

L represents a substituted or unsubstituted arylene group having 6 to 60 ring carbon atoms, a substituted or unsubstituted heteroarylene group having 5 to 60 ring atoms, or a substituted or unsubstituted alkylene group having 1 to 50 carbon atoms;

Y represents NZ, O, S, or CR'R";

$R^1$ to $R^8$, Z, R', and R" each independently represent a single bond, a hydrogen atom or a substituent, wherein adjacent substituents may be bonded to each other to form a saturated or unsaturated ring structure;

provided that when Y is NZ, $R^1$ and $R^8$ are hydrogen atoms; and one selected from $R^1$ to $R^8$, Z, R', and R" represents a single bond which bonds to L, wherein when n is 0, formula (2) bonds to formula (1) via a single bond, and when n is 2 or more, groups L may be the same or different and may be bonded to each other to form a saturated or unsaturated ring structure.

In formula (1), preferably two selected from $B^1$ to $B^3$, i.e., $B^1$ and $B^2$, $B^1$ and $B^3$, or $B^2$ and $B^3$, are represented by formula (2), and more preferably $B^1$ and $B^2$ are represented by formula (2).

In formula (2), Y preferably represents NZ and n is preferably 0 or 1 and more preferably 1.

The carbazole derivative of formula (1) is preferably represented by formula (3):

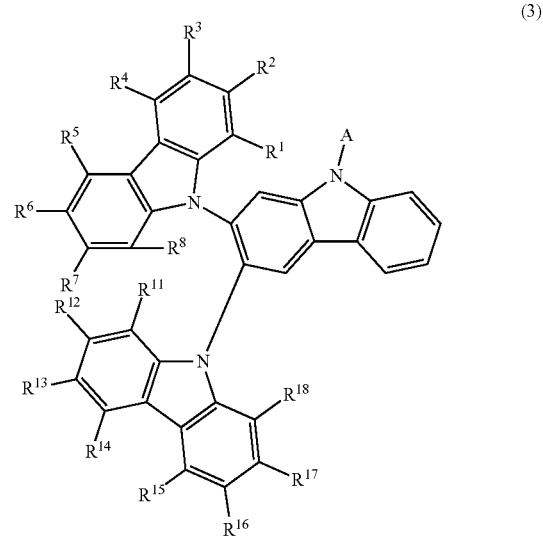

(3)

wherein $R^{11}$ to $R^{18}$ are the same as defined above with respect to $R^1$ to $R^8$.

The carbazole derivative of formula (3) is particularly preferably represented by formula (4) or (5):

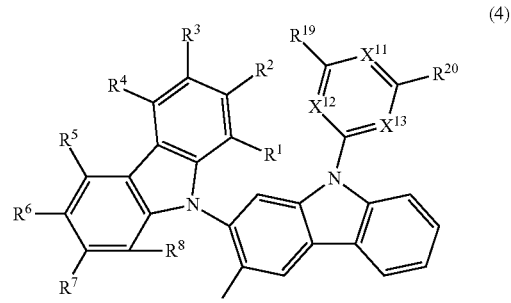

(4)

-continued

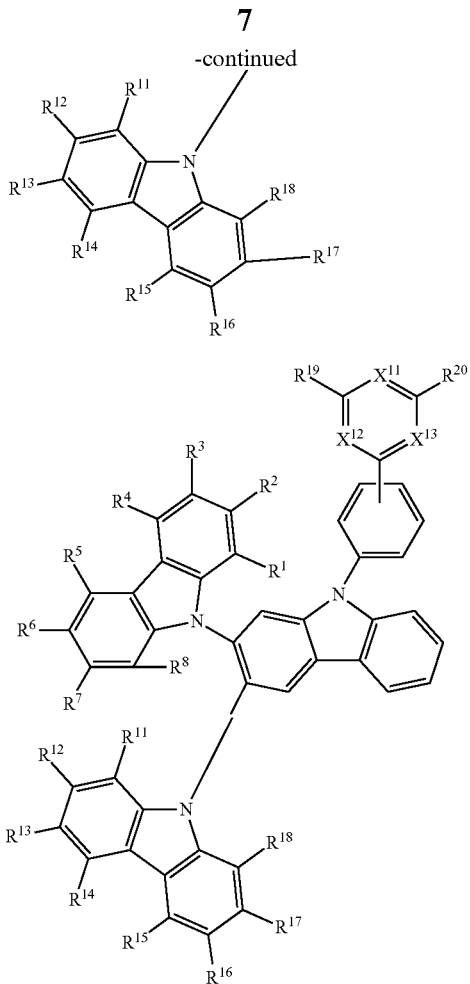

(5)

wherein:

$X^{11}$ to $X^{13}$ each independently represent $CR^{51}$ or N, provided that at least one selected from $X^{11}$ to $X^{13}$ represents N; and $R^{19}$ to $R^{20}$ and $R^{51}$ each independently represent a hydrogen atom or a substituent, wherein when more than one $R^{51}$ occurs, groups $R^{51}$ may be the same or different.

The carbazole derivative in an aspect of the present invention may be represented by formula (10):

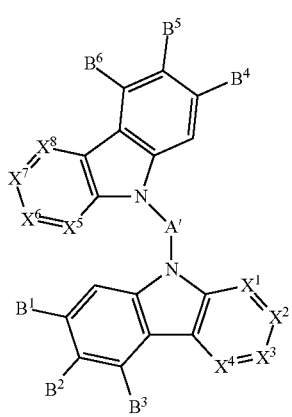

(10)

wherein:

A' represents a substituted or unsubstituted arylene group having 6 to 60 ring carbon atoms or a substituted or unsubstituted heteroarylene group having 5 to 60 ring atoms;

$X^1$ and $X^5$ each represent N or CH;

$X^2$ to $X^4$ and $X^6$ to $X^8$ each represent N or CR;

R and $B^1$ to $B^6$ each independently represent a hydrogen atom or a substituent, wherein adjacent substituents may be bonded to each other to form a saturated or unsaturated ring structure and when more than one R occurs, groups R may be the same or different; and at least two selected from $B^1$ to $B^3$ are represented by formula (2) described above.

In a preferred carbazole derivative of formula (10), at least two selected from $B^1$ to $B^3$ are represented by formula (2) described below and at least two selected from $B^4$ to $B^6$ are represented by formula (2) described above.

The carbazole derivative of formula (10) is preferably represented by formula (11):

(11)

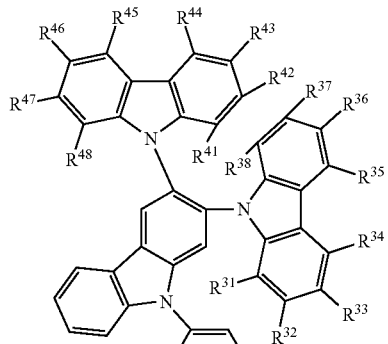

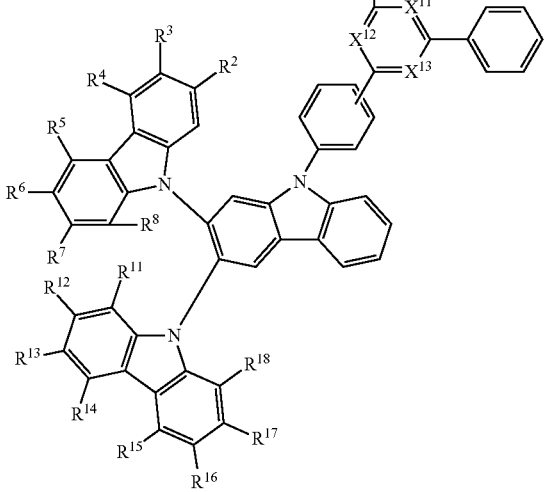

wherein:

$X^{11}$ to $X^{13}$ each independently represent $CR^{51}$ or N;

$R^1$ to $R^8$, $R^{11}$ to $R^{18}$, $R^{31}$ to $R^{38}$ and $R^{41}$ to $R^{48}$ are the same as defined above with respect to $R^1$ to $R^8$ of formula (1); and $R^{51}$ represents a hydrogen atom or a substituent, when more than one $R^{51}$ occurs, groups $R^{51}$ may be the same or different.

Formula (2) is preferably represented by formula (2-1), more preferably by formula (2-2), and still more preferably by formula (2-3):

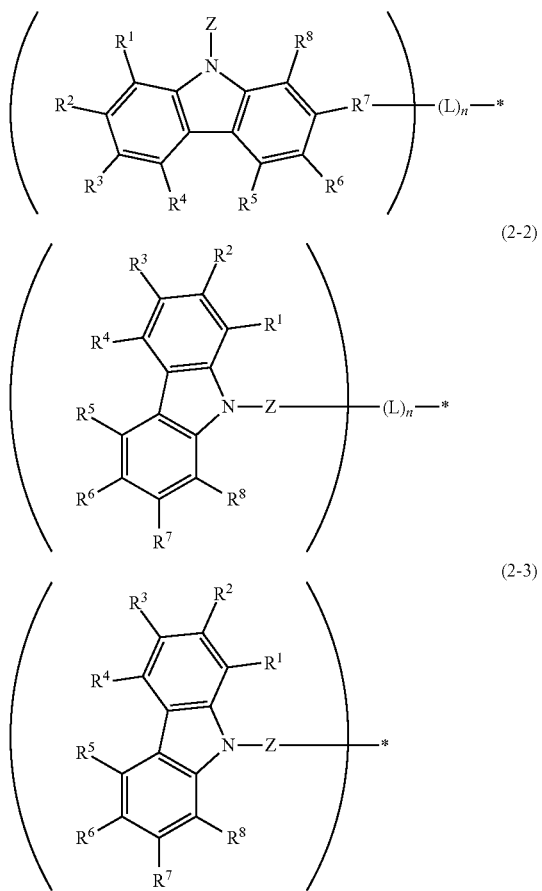

In formulae (1) to (5) and (10) to (11), R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R" each independently represent a hydrogen atom or a substituent which is preferably selected from the group (A), more preferably selected from the group (B), and still more preferably selected from the group (C), each described below.

The group (A) consists of a substituted or unsubstituted alkyl group having 1 to 50 carbon atoms; a substituted or unsubstituted cycloalkyl group having 3 to 50 ring carbon atoms; a substituted or unsubstituted aryl group (a synonym for an aromatic hydrocarbon group and the same applies below) having 6 to 60 ring carbon atoms; a substituted or unsubstituted aralkyl group having 7 to 61 carbon atoms; an amino group; a mono- or disubstituted amino group having a substituent selected from a substituted or unsubstituted alkyl group having 1 to 50 carbon atoms and a substituted or unsubstituted aryl group having 6 to 60 ring carbon atoms; a substituted or unsubstituted alkoxy group having 1 to 50 carbon atoms; a substituted or unsubstituted aryloxy group having 6 to 60 ring carbon atoms; a substituted or unsubstituted alkylthio group having 1 to 50 carbon atoms; a substituted or unsubstituted arylthio group having 6 to 60 ring carbon atoms; a mono-, di-, or trisubstituted silyl group having a substituent selected from a substituted or unsubstituted alkyl group having 1 to 50 carbon atoms and a substituted or unsubstituted aryl group having 6 to 60 ring carbon atoms; a substituted or unsubstituted heteroaryl group (a synonym for a heterocyclic group and the same applies below) having 5 to 60 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 60 ring carbon atoms; a disubstituted phosphoryl group having a substituent selected from a substituted or unsubstituted alkyl group having 1 to 50 carbon atoms and a substituted or unsubstituted aryl group having 6 to 60 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl- or aryl-substituted carbonyl group; a carboxyl group; a vinyl group; a (meth)acryloyl group; an epoxy group; and an oxetanyl group.

The group (B) consists of a substituted or unsubstituted alkyl group having 1 to 50 carbon atoms; a substituted or unsubstituted cycloalkyl group having 3 to 50 ring carbon atoms; a substituted or unsubstituted aryl group having 6 to 60 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 60 ring carbon atoms; a substituted or unsubstituted alkoxy group having 1 to 50 carbon atoms; a substituted or unsubstituted aryloxy group having 6 to 60 ring carbon atoms; a substituted or unsubstituted alkylthio group having 1 to 50 carbon atoms; a substituted or unsubstituted arylthio group having 6 to 60 ring carbon atoms; a mono-, di-, or trisubstituted silyl group having a substituent selected from a substituted or unsubstituted alkyl group having 1 to 50 carbon atoms and a substituted or unsubstituted aryl group having 6 to 60 ring carbon atoms; a substituted or unsubstituted heteroaryl group having 5 to 60 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 60 ring carbon atoms; a disubstituted phosphoryl group having a substituent selected from a substituted or unsubstituted alkyl group having 1 to 50 carbon atoms and a substituted or unsubstituted aryl group having 6 to 60 ring carbon atoms.

The group (C) consists of a substituted or unsubstituted alkyl group having 1 to 50 carbon atoms; a substituted or unsubstituted cycloalkyl group having 3 to 50 ring carbon atoms; a substituted or unsubstituted aryl group having 6 to 60 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 60 ring carbon atoms; a mono-, di-, or trisubstituted silyl group having a substituent selected from a substituted or unsubstituted alkyl group having 1 to 50 carbon atoms and a substituted or unsubstituted aryl group having 6 to 60 ring carbon atoms; a substituted or unsubstituted heteroaryl group having 5 to 60 ring atoms; a halogen atom; and a cyano group.

Of the above substituents, preferred are a substituted or unsubstituted phenyl group; a substituted or unsubstituted biphenylyl group; a substituted or unsubstituted terphenylyl group; a substituted or unsubstituted naphthyl group; a substituted or unsubstituted phenanthryl group; a substituted or unsubstituted fluorenyl group; a substituted or unsubstituted 9,9'-spirobifluorenyl group; a substituted or unsubstituted chrysenyl group; a substituted or unsubstituted triphenylenyl group; a substituted or unsubstituted 9,9-dimethylfluorenyl group; a substituted or unsubstituted 9,9-diphenylfluorenyl group; a substituted or unsubstituted pyridyl group; a substituted or unsubstituted pyrimidinyl group; a substituted or unsubstituted triazinyl group; a substituted or unsubstituted benzofuranyl group; a substituted or unsubstituted isobenzofuranyl group; a substituted or unsubstituted quinolyl group; a substituted or unsubstituted isoquinolyl group; a substituted or unsubstituted quinazolinyl group; a substituted or unsubstituted benzothiophenyl group; a substituted or unsubstituted isobenzothiophenyl group; a substituted or unsubstituted indolizinyl group; a substituted or unsubstituted dibenzofuranyl group; a substituted or unsubstituted dibenzothiophenyl group; a substituted or unsubstituted carbazolyl group; a substituted or unsubstituted azatriphenylenyl group; a substituted or unsubstituted diazatriphenylenyl group; a substituted or unsubstituted xanthenyl group; a substituted or unsubstituted azacarbazolyl group; a substituted or unsubstituted azadibenzofuranyl group; and a substituted or unsubstituted azadibenzothiophenyl group.

Examples of the alkyl group having 1 to 50, preferably 1 to 18, more preferably 1 to 8 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, an octadecyl group, a tetracosanyl group, and a tetracontanyl group. Preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, and an octadecyl group. More preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), and an octyl group (inclusive of isomeric groups).

Examples of the cycloalkyl group having 3 to 50, preferably 3 to 10, more preferably 3 to 8, still more preferably 5 or 6 ring carbon atoms include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the aryl group having 6 to 60, preferably 6 to 25, more preferably 6 to 18 ring carbon atoms include a phenyl group, a naphthyl group, a naphthylphenyl group, a biphenylyl group, a terphenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, a dibenzanthryl group, a 9,9-dimethylfluorenyl group, and a 9,9-diphenylfluorenyl group. Preferred are a phenyl group, a naphthyl group, a biphenylyl group, a terphenylyl group, a phenanthryl group, a benzophenanthryl group, a fluorenyl group, a 9,9'-spirobifluorenyl group, a benzofluorenyl group, a dibenzofluorenyl group, a chrysenyl group, a benzochrysenyl group, a s-indacenyl group, an as-indacenyl group, a triphenylenyl group, a benzotriphenylenyl group, an anthryl group, a 9,9-dimethylfluorenyl group, and a 9,9-diphenylfluorenyl group. More preferred are a phenyl group, a biphenylyl group, a terphenylyl group, a naphthyl group, a phenanthryl group, a fluorenyl group, a 9,9'-spirobifluorenyl group, a chrysenyl group, a triphenylenyl group, a 9,9-dimethylfluorenyl group, and a 9,9-diphenylfluorenyl group.

The heteroaryl group having 5 to 60, preferably 5 to 24, more preferably 5 to 13 ring atoms include at least one, preferably 1 to 5, more preferably 1 to 3, and still more preferably 1 or 2 hetero atoms, for example, a nitrogen atom, a sulfur atom, an oxygen atom, and a phosphorus atom.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, and a dinaphthothienothiophenyl group. Preferred are a pyridyl group, a pyridazinyl group, a pyrimidinyl group, a pyrazinyl group, a triazinyl group, an imidazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a quinazolinyl group, a quinoxalinyl group, a benzimidazolyl group, a benzoxazolyl group, a benzothiazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, an azatriphenylenyl group, a diazatriphenylenyl group, a xanthenyl group, an azacarbazolyl group, an azadibenzofuranyl group, and an azadibenzothiophenyl group. More preferred are a pyridyl group, a pyrimidinyl group, a triazinyl group, a benzofuranyl group, an isobenzofuranyl group, a quinolyl group, an isoquinolyl group, a quinazolinyl group, a benzothiophenyl group, an isobenzothiophenyl group, an indolizinyl group, a dibenzofuranyl group, a dibenzothiophenyl group, a carbazolyl group, an azatriphenylenyl group, a diazatriphenylenyl group, a xanthenyl group, an azacarbazolyl group, an azadibenzofuranyl group, and an azadibenzothiophenyl group.

Examples of the aralkyl group having 7 to 61 total carbon atoms having an aryl group having 6 to 60, preferably 6 to 25, more preferably 6 to 18 ring carbon atoms include those having the aryl group mentioned above.

Examples of the mono- or di-substituted amino group having a substituent selected from an alkyl group having 1 to 50, preferably 1 to 18, more preferably 1 to 8 carbon atoms and an aryl group having 6 to 60, preferably 6 to 25, more preferably 6 to 18 ring carbon atoms include those having a substituent selected from the alkyl group and the aryl group mentioned above. Preferred is the di-substituted amino group and more preferred is the di-substituted amino group having a substituent selected from the aryl group mentioned above.

Examples of the alkoxy group having an alkyl group having 1 to 50, preferably 1 to 18, more preferably 1 to 8 carbon atoms include those having the alkyl group mentioned above, with a methoxy group and an ethoxy group being preferred.

Examples of the aryloxy group having an aryl group having 6 to 60, preferably 6 to 25, more preferably 6 to 18 ring carbon atoms include those having the aryl group mentioned above, with a phenoxy group being preferred.

Examples of the alkylthio group having an alkyl group having 1 to 50, preferably 1 to 18, more preferably 1 to 8 carbon atoms include those having the alkyl group mentioned above.

Examples of the arylthio group having an aryl group having 6 to 60, preferably 6 to 25, more preferably 6 to 18 ring carbon atoms include those having the aryl group mentioned above.

Examples of the mono-, di-, or trisubstituted silyl group having a substituent selected from an alkyl group having 1 to 50, preferably 1 to 18, more preferably 1 to 8 carbon atoms and an aryl group having 6 to 60, preferably 6 to 25, more preferably 6 to 18 ring carbon atoms include those having a substituent selected from the alkyl group and the aryl group mentioned above, for example, a trimethylsilyl group, a triethylsilyl group, a t-butyldimethylsilyl group, a vinyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group.

Examples of the haloalkyl group having 1 to 50, preferably 1 to 18, more preferably 1 to 8 carbon atoms include those obtained by replacing one or more hydrogen atoms of the alkyl groups mentioned above with a halogen atom, such as a fluorine atom, a chlorine atom, a bromine atom and an iodine atom.

Examples of the sulfonyl group having a substituent selected from an alkyl group having 1 to 50, preferably 1 to 18, more preferably 1 to 8 carbon atoms and an aryl group having 6 to 60, preferably 6 to 25, more preferably 6 to 18 ring carbon atoms include those having a substituent selected from the alkyl group and the aryl group mentioned above.

Examples of the di-substituted phosphoryl group having a substituent selected from an alkyl group having 1 to 50, preferably 1 to 18, more preferably 1 to 8 carbon atoms and an aryl group having 6 to 60, preferably 6 to 25, more preferably 6 to 18 ring carbon atoms include those having a substituent selected from the alkyl group and the aryl group mentioned above.

Examples of the alkylsulfonyloxy group, the arylsulfonyloxy group, the alkylcarbonyloxy group, the arylcarbonyloxy group, and the alkyl- or aryl-substituted carbonyl group include those having a substituent selected from the alkyl group and the aryl group mentioned above.

Of the above substituents, preferred are a fluorine atom, a cyano group, the alkyl group, the substituted or unsubstituted aryl group, the substituted or unsubstituted heteroaryl group, and the di-substituted amino group.

Examples of the substituted or unsubstituted aryl group having 6 to 60 ring carbon atoms for A of formula (1) include those described with respect to the substituent represented by R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R".

Examples of the substituted or unsubstituted heteroaryl group having 5 to 60 ring atoms for A include those mentioned above with respect to the substituent represented by R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R".

Examples of the substituted or unsubstituted arylene group having 6 to 60 ring carbon atoms for A' of formula (10) include divalent groups corresponding to the aryl groups mentioned above with respect to the substituent represented by R, $B^1$ to $B^3$, $R^1$ to $R^8$, $R^{11}$ to $R^{20}$, $R^{31}$ to $R^{38}$, $R^{41}$ to $R^{48}$, $R^{51}$, Z, R', and R".

Examples of the substituted or unsubstituted heteroarylene group having 5 to 60 ring atoms for A' include divalent groups corresponding to the heteroaryl groups mentioned above with respect to the substituent represented by R, $B^1$ to $B^3$, $R^1$ to $R^8$, $R^{11}$ to $R^{20}$, $R^{31}$ to $R^{38}$, $R^{41}$ to $R^{48}$, $R^{51}$, Z, R', and R".

Examples of the substituted or unsubstituted arylene group having 6 to 60 ring carbon atoms for L of formula (2) include divalent groups corresponding to the aryl groups mentioned above with respect to the substituent represented by R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R".

Examples of the substituted or unsubstituted heteroarylene group having 5 to 60 ring atoms for L include divalent groups corresponding to the heteroaryl groups mentioned above with respect to the substituent represented by R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R".

Examples of the substituted or unsubstituted alkylene group having 1 to 50 carbon atoms for L include divalent groups corresponding to the alkyl groups mentioned above with respect to the substituent represented by R, $B^1$ to $B^6$, $R^1$ to $R^8$, $R^1$ to $R^{20}$, $R^{31}$ to $R^{38}$, $R^{41}$ to $R^{48}$, $R^{51}$, Z, R', and R".

In formulae (1) to (5) and (10), examples of the ring which may be formed by the bonding between the adjacent substituents selected from R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R" include a substituted or unsubstituted aryl group having 6 to 60 ring carbon atoms or a substituted or unsubstituted heteroaryl group having 5 to 60 ring atoms.

Examples of the substituted or unsubstituted aryl group having 6 to 60 ring carbon atoms include those mentioned above with respect to the substituent represented by R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R".

Examples of the substituted or unsubstituted heteroaryl group having 5 to 60 ring atoms include those mentioned above with respect to the substituent represented by R, $B^1$ to $B^6$, $R^1$ to $R^8$, $R^{11}$ to $R^{20}$, $R^{31}$ to $R^{38}$, $R^{41}$ to $R^{48}$, $R^{51}$, Z, R', and R".

The carbazole derivative in an aspect of the invention preferably comprises a ring-containing substituent, particularly, A comprises a ring-containing group.

A material for organic EL devices which comprises a carbazole derivative comprising a ring-containing substituent has an effect of, for example, providing an organic thin film with good film properties.

Examples of the ring-containing group include those comprising a group selected from a substituted or unsubstituted cycloalkyl group having 5 to 60, preferably 3 to 6, and more preferably 5 or 6 ring carbon atoms; a substituted or unsubstituted aryl group having 6 to 60, preferably 6 to 24, and more preferably 6 to 18 ring carbon atoms; an aralkyl group having 7 to 61 carbon atoms in total, which includes a substituted or unsubstituted aryl group having 6 to 60, preferably 6 to 24, and more preferably 6 to 18 ring carbon atoms; an amino group having a substituted or unsubstituted aryl substituent having 6 to 60, preferably 6 to 24, and more preferably 6 to 18 ring carbon atoms; an aryloxy group having a substituted or unsubstituted aryl group having 6 to 60, preferably 6 to 24, and more preferably 6 to 18 ring carbon atoms; a silyl group having a substituted or unsubstituted aryl substituent having 6 to 60, preferably 6 to 24, and more preferably 6 to 18 ring carbon atoms; a substituted or unsubstituted heteroaryl group having 5 to 60, preferably 5 to 24, and more preferably 5 to 13 ring atoms; a sulfonyl group having a substituted or unsubstituted aryl substituent having 6 to 60, preferably 6 to 24, and more preferably 6 to 18 ring carbon atoms; and a phosphonyl group having a substituted or unsubstituted aryl substituent having 6 to 60, preferably 6 to 24, and more preferably 6 to 18 ring carbon atoms. Preferred are those comprising a substituted or unsubstituted aryl group having 6 to 60 ring carbon atoms, a substituted or unsubstituted heteroaryl group having 5 to 60 ring atoms, or a mono- or di-substituted amino group having a substituted or unsubstituted aryl group having 6 to 60 ring carbon atoms. The details of the above groups are the same as those mentioned above.

Of the above, a substituted or unsubstituted aryl group having 6 to 60 ring carbon atoms and a substituted or unsubstituted heteroaryl group having 5 to 60 ring atoms are preferred.

The ring-containing group may be a substituent having a ring-containing group thereon. Examples of such a substituent are those as mentioned above.

A is preferably a group represented by formula (I) and more preferably a group represented by formula (II) or (III):

(I)

wherein $L^1$ represents a single bond or a substituted or unsubstituted arylene group having 6 to 30 ring carbon atoms; $R^1$ represents a hydrogen atom or a substituent; s represents an integer of 1 to 5, when s is 2 or more, groups $R^{10}$ may be the same or different; and * represents a bonding site;

(II)

wherein $R^{10}$ represents a hydrogen atom or a substituent; s represents an integer of 1 to 5, when s is 2 or more, groups $R^{10}$ may be the same or different; and * represents a bonding site; and

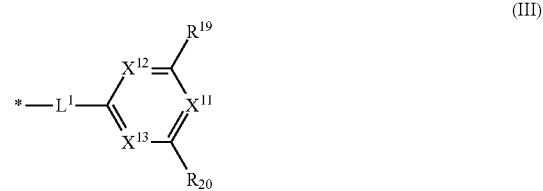
(III)

wherein $L^1$ represents a single bond or a substituted or unsubstituted arylene group having 6 to 30 ring carbon atoms; $X^{11}$ to $X^{13}$ each represent $CR^{51}$ or a nitrogen atom, provided that at least one selected from $X^1$ to $X^{13}$ is a nitrogen atom; $R^{51}$ and $R^{19}$ to $R^{20}$ each independently represent a hydrogen atom or a substituent; adjacent substituents may be bonded to each other to form a saturated or unsaturated ring structure; when more than one $R^{51}$ occurs, groups $R^{51}$ may be the same or different; and * represents a bonding site.

Examples of the ring which is optionally formed by the adjacent groups selected from $R^{51}$ and $R^{19}$ to $R^{20}$ of formula (III) include a substituted or unsubstituted arylene group having 6 to 60 ring carbon atoms and a substituted or unsubstituted heteroarylene group having 5 to 60 ring atoms.

Examples of $R^{10}$ of formulae (I) and (II) include those mentioned above with respect to R, $B^1$ to $B^3$, $R^1$ to $R^8$, $R^{11}$ to $R^{20}$, $R^{31}$ to $R^{38}$, $R^{41}$ to $R^{48}$, $R^{51}$, Z, R', and R".

Examples of $R^{19}$ to $R^{20}$ and $R^{51}$ of formula (III) include those mentioned above with respect to R, $B^1$ to $B^3$, $R^1$ to $R^8$, $R^{11}$ to $R^{18}$, $R^{31}$ to $R^{38}$, $R^{41}$ to $R^{48}$, Z, R', and R". $R^{51}$ more preferably represents a hydrogen atom, a substituted or unsubstituted aryl group having 6 to 30 ring carbon atoms, or a substituted or unsubstituted heteroaryl group having 5 to 30 ring atoms. More preferably, $R^{19}$ to $R^{20}$ each independently represent a substituted or unsubstituted aryl group having 6 to 30 ring carbon atoms or a substituted or unsubstituted heteroaryl group having 5 to 30 ring atoms.

The above carbazole derivative in an aspect of the invention is useful as a material for organic EL devices, and the production method thereof is not particularly limited and one of ordinary skill in the art easily produces the carbazole derivative by utilizing or modifying known synthetic reactions while taking the examples in the present specification into consideration.

Material for Organic Electroluminescence Devices

The material for organic electroluminescence devices in an aspect of the invention comprises the carbazole derivative mentioned above. The content of the carbazole derivative in the material for organic electroluminescence devices is, but not particularly limited, 1% by mass or more, preferably 10% by mass or more, more preferably 50% by mass or more, still more preferably 80% by mass or more, and particularly preferably 90% by mass or more.

The carbazole derivative and the material for organic EL devices each in an aspect of the invention are useful as a material for producing an organic EL device and may be used, for example, in a light emitting layer of a fluorescent emission unit as a host material or a dopant material and in a light emitting layer of a phosphorescent emission unit as a host material. In this case, the light emitting layer comprises the carbazole derivative of the invention together with a fluorescent emitting material or a phosphorescent emitting material. In addition, in either a fluorescent emission unit or a phosphorescent emission unit, the carbazole derivative and the material for organic EL devices of the invention are also useful as a material for forming an anode-side organic thin film layer which is formed between an anode and a light emitting layer and a material for forming a cathode-side organic thin film layer which is formed between a cathode and a light emitting layer, i.e., also useful as a material for forming a hole transporting layer, a hole injecting layer, an electron transporting layer, an electron injecting layer, a hole blocking layer, and an electron blocking layer.

The "emission unit" referred to herein is the smallest unit for emitting light by the recombination of injected holes and injected electrons, which comprises one or more organic layers wherein at least one layer is a light emitting layer.

Examples of the carbazole derivative in an aspect of the present invention are described below, although not limited thereto.

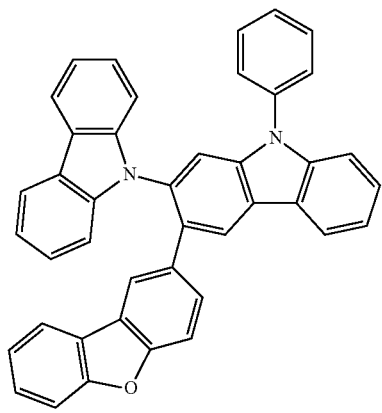

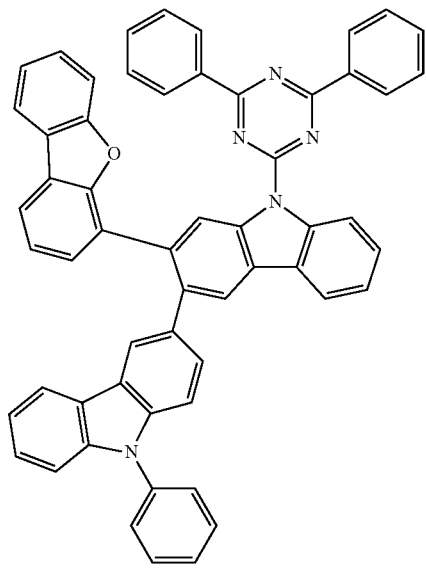

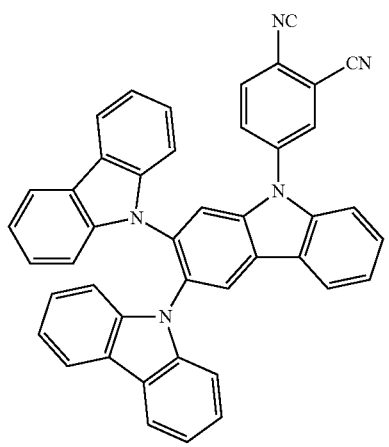

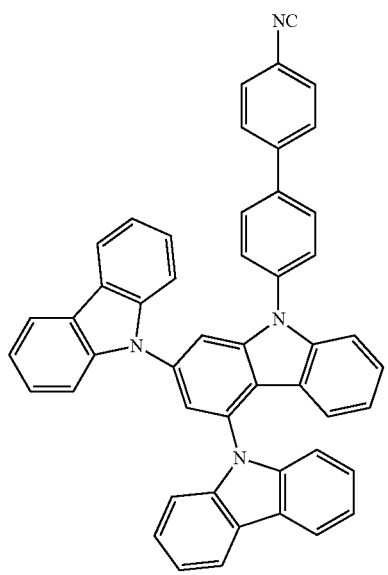

-continued
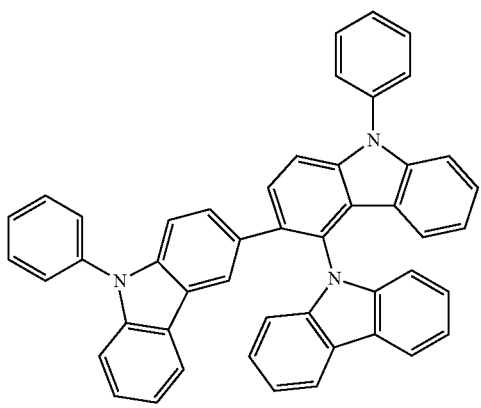
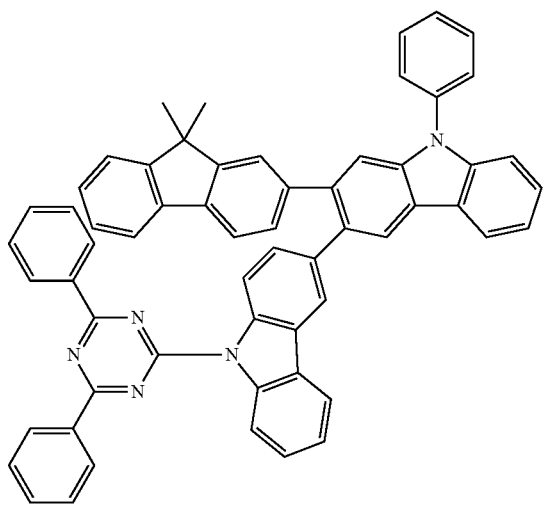
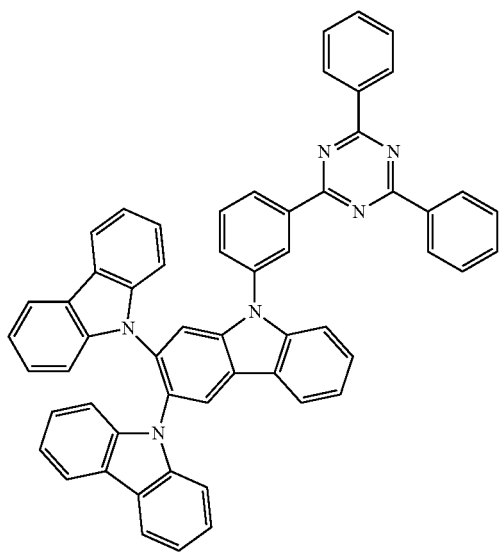
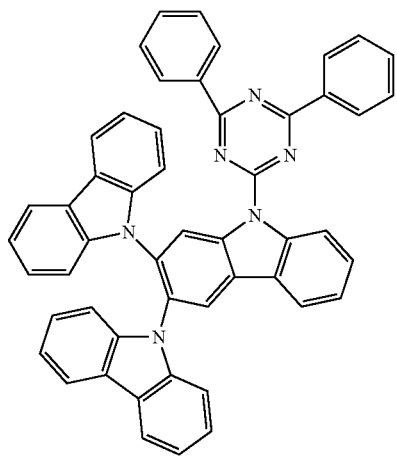
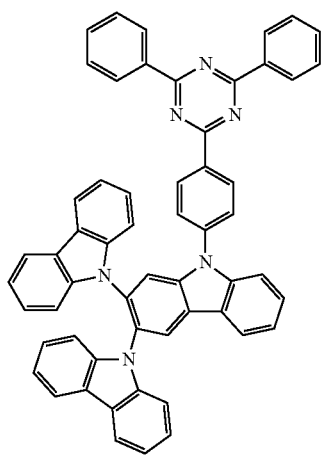
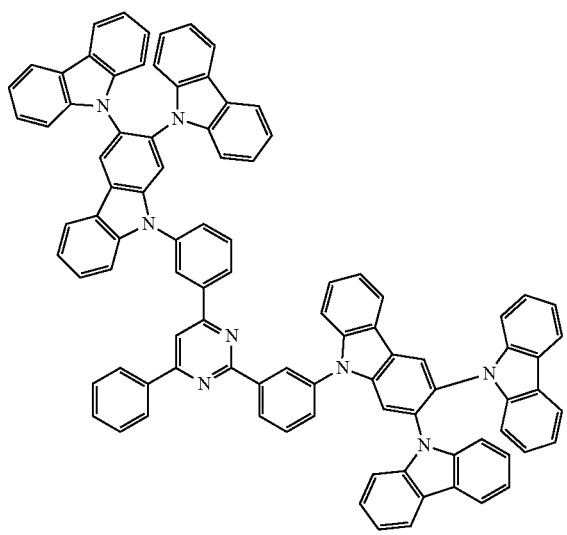

-continued
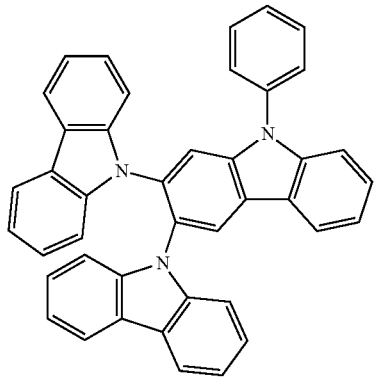
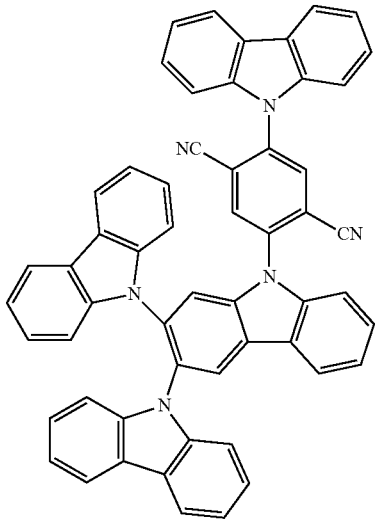
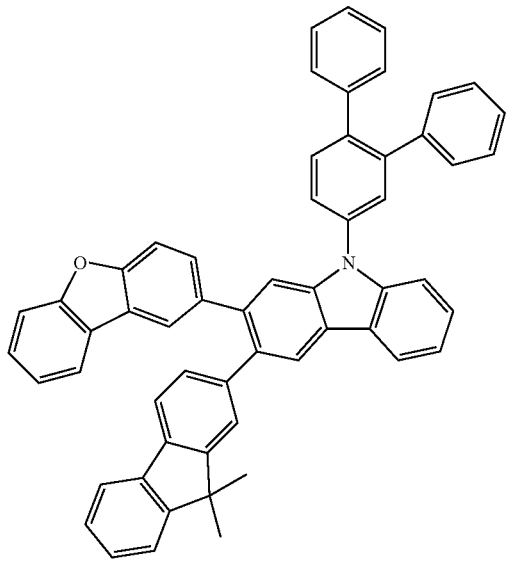
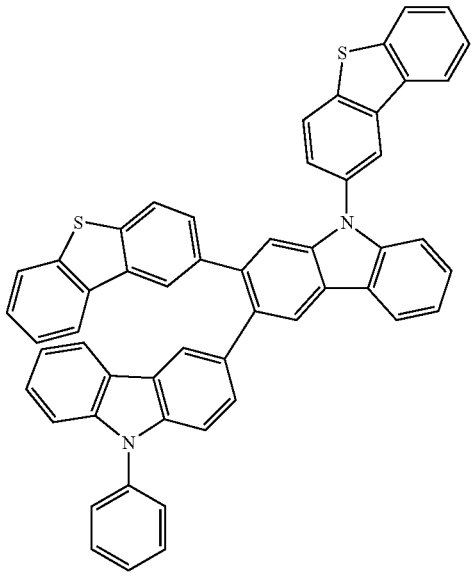
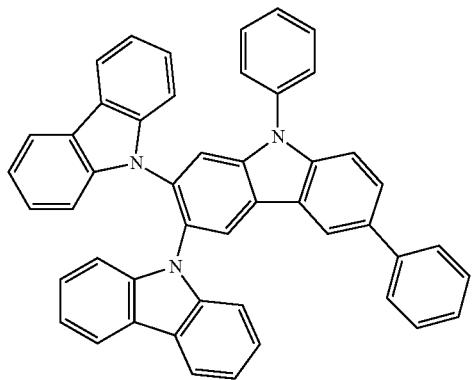
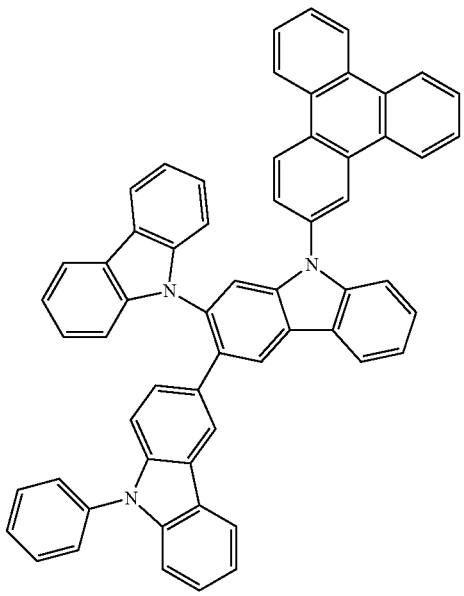

-continued
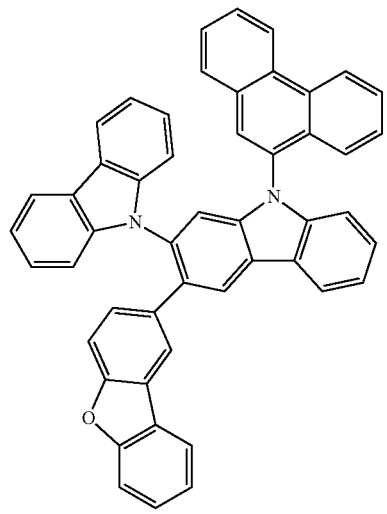
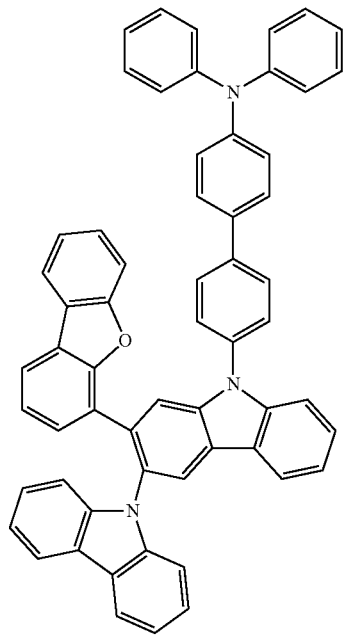
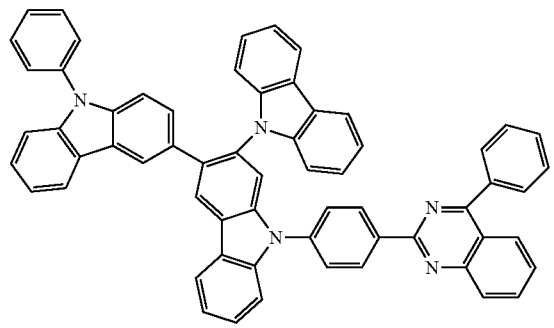
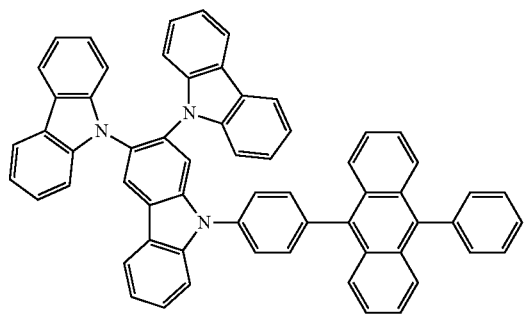
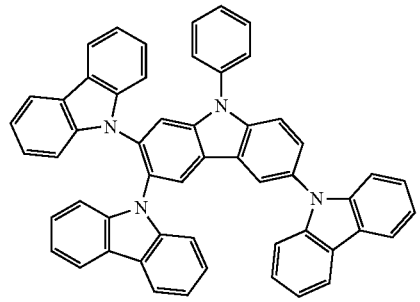
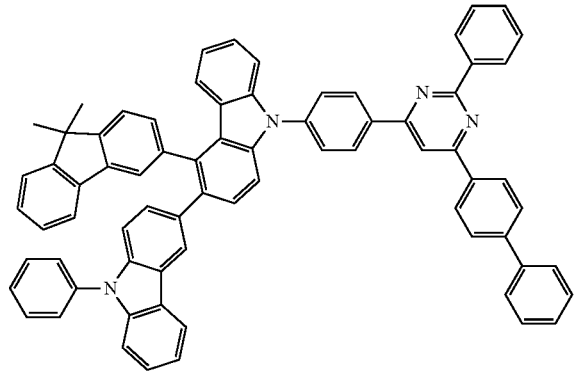

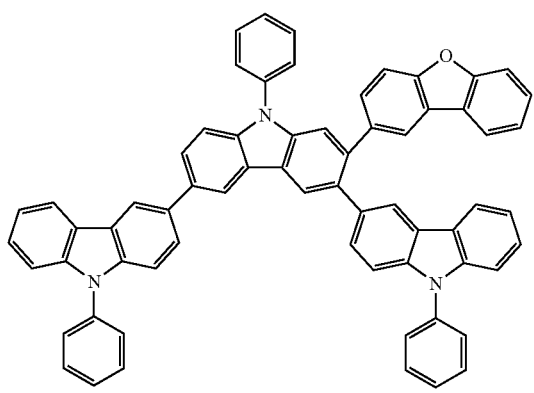
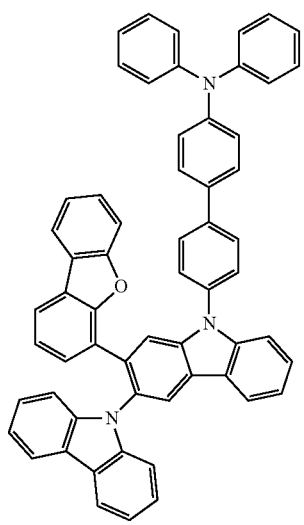
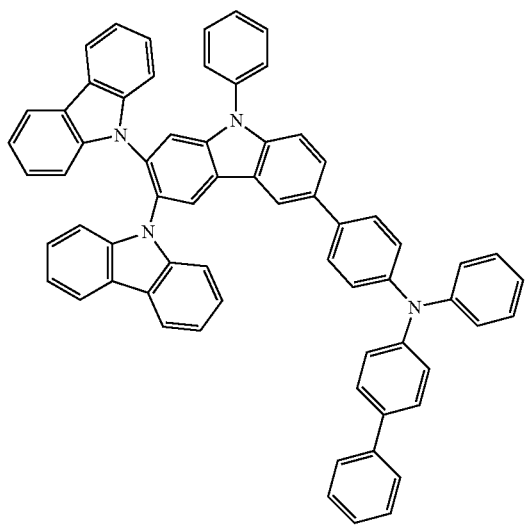
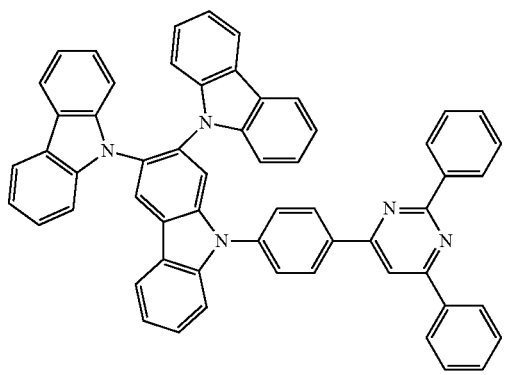
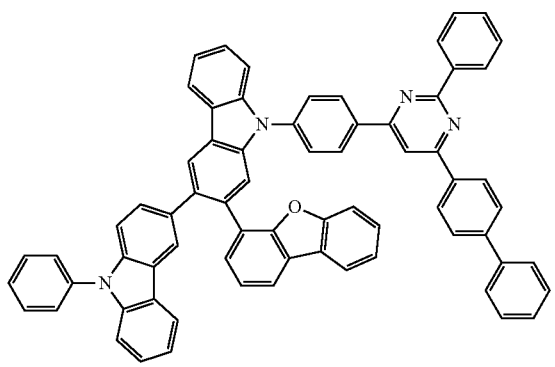
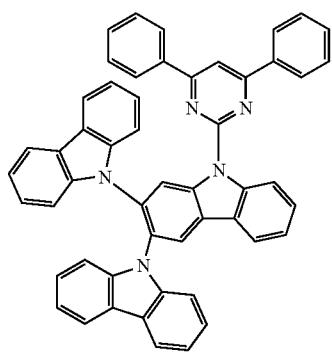

27
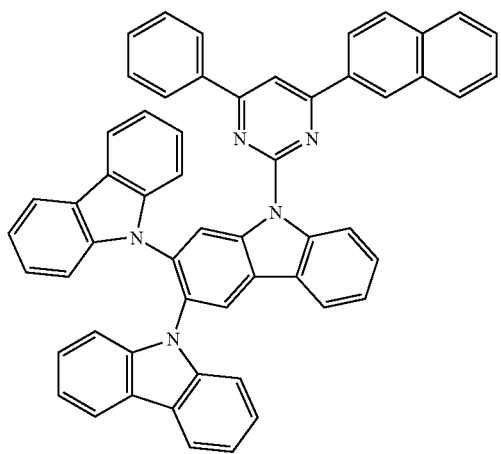
28
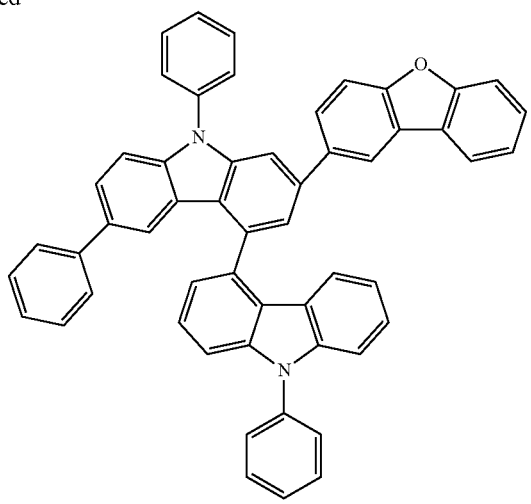
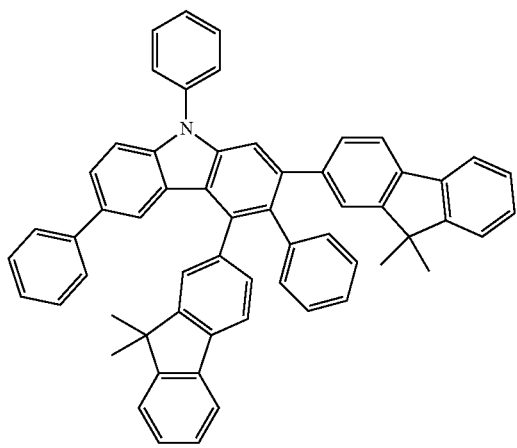
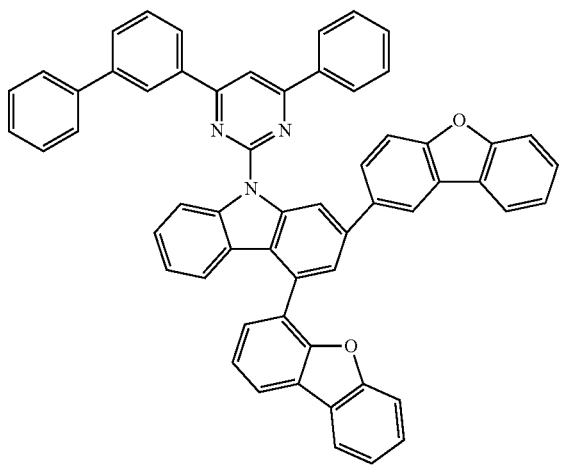
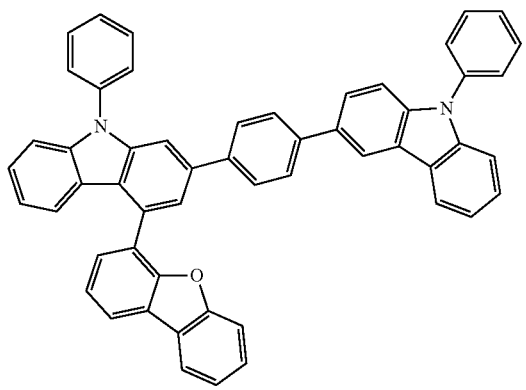
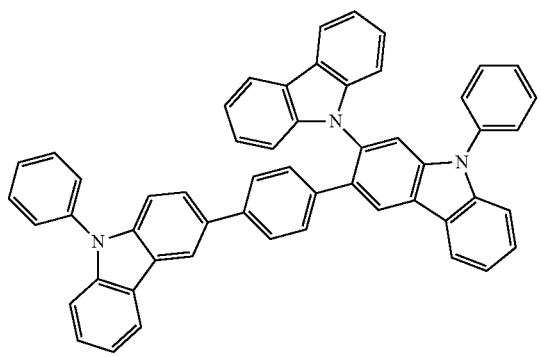

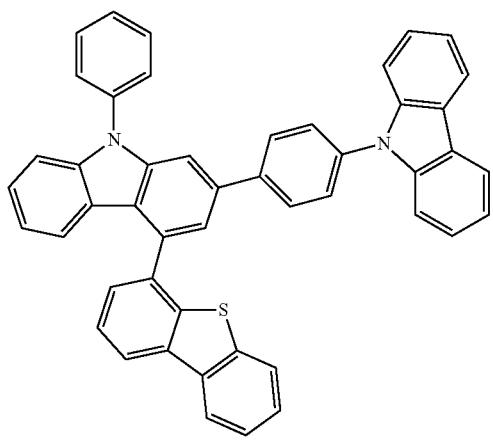
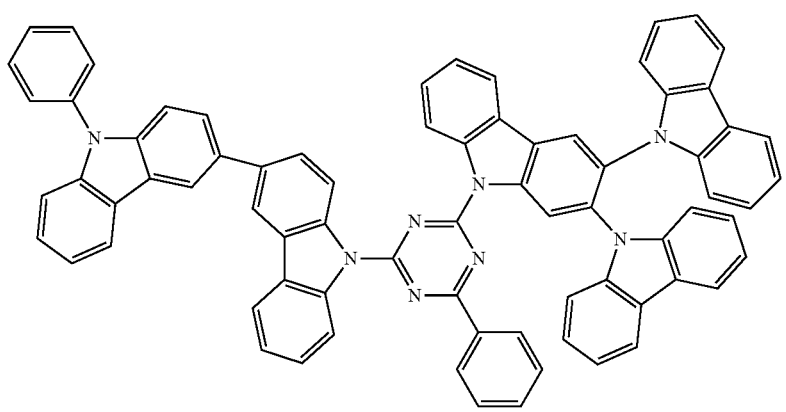
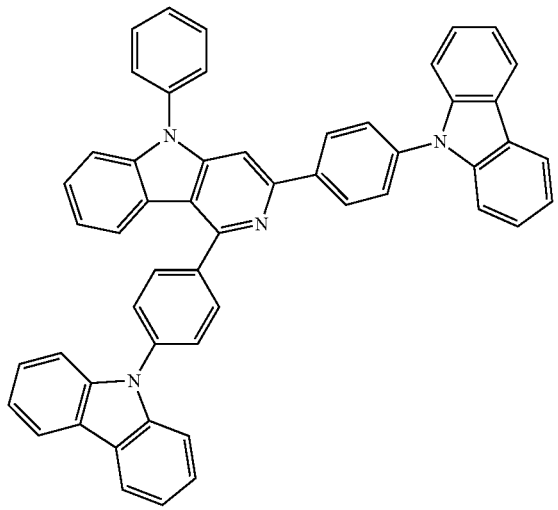

-continued
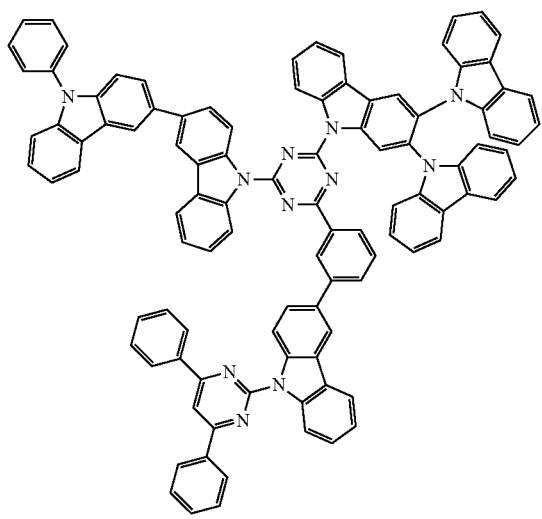 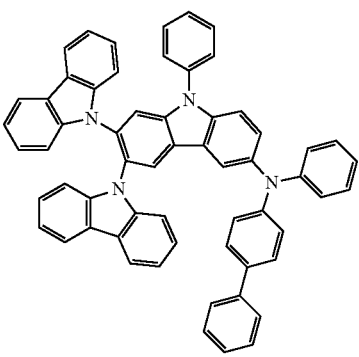
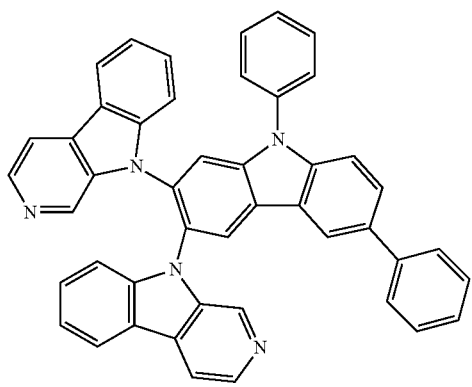 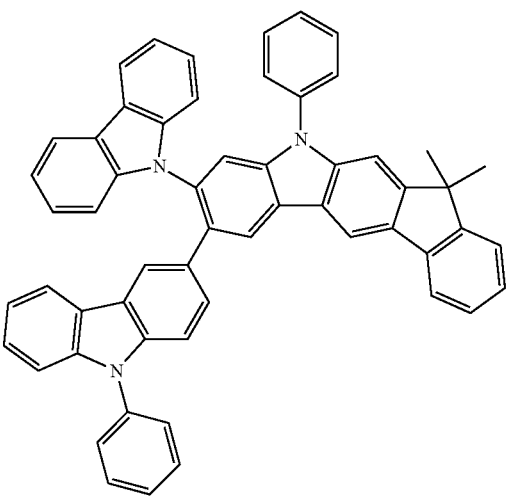
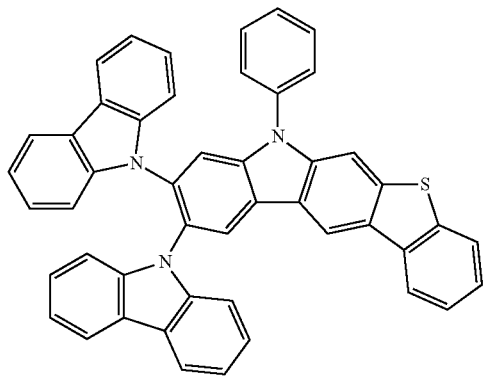 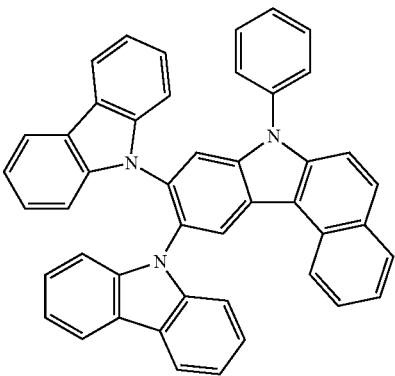

-continued
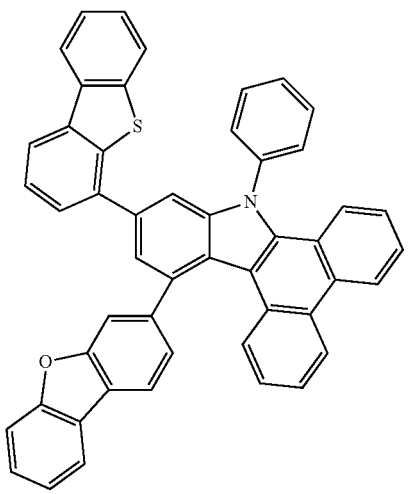
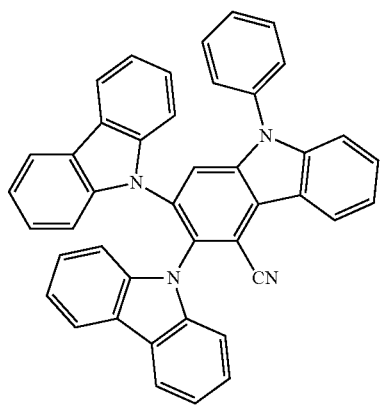
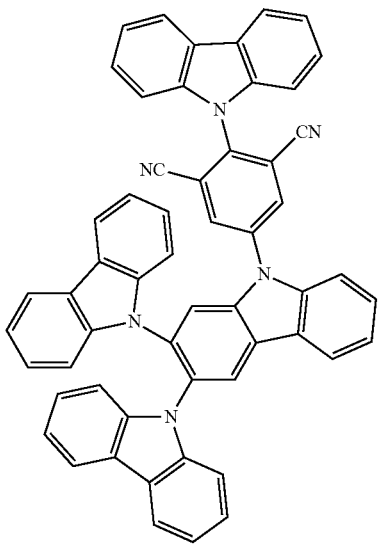
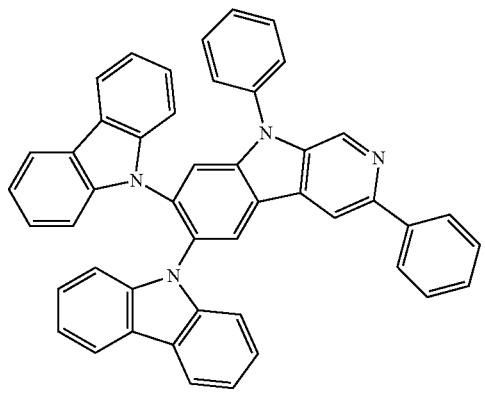
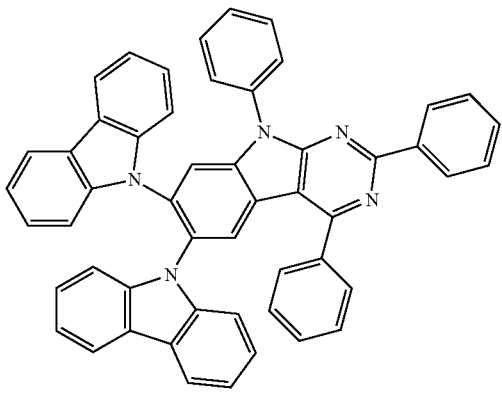
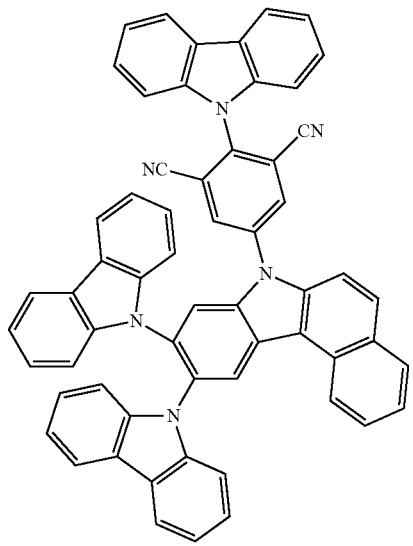

-continued
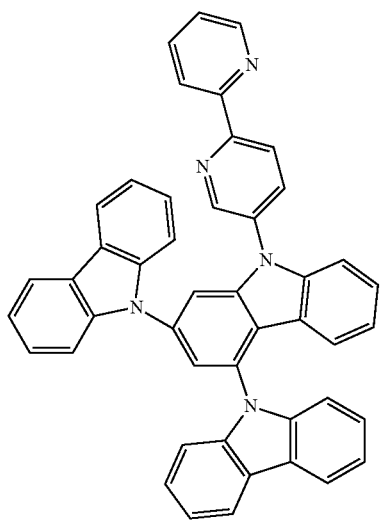
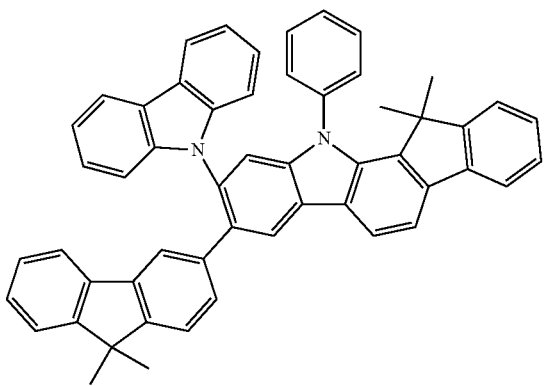
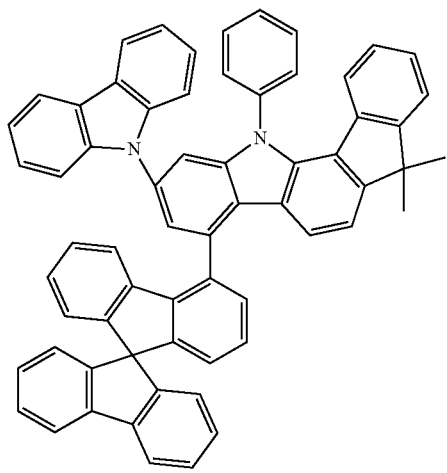
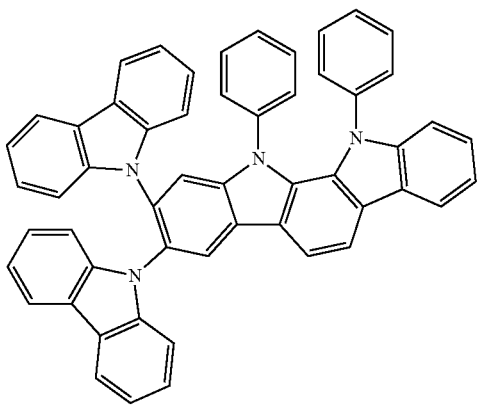
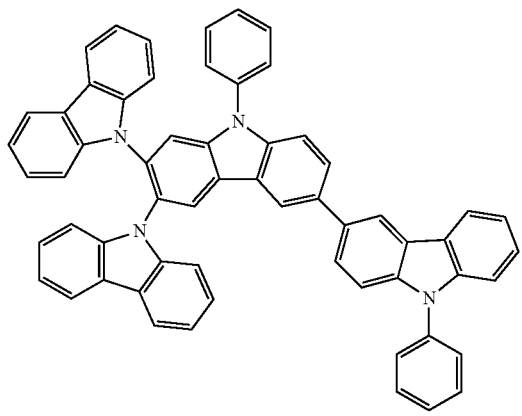
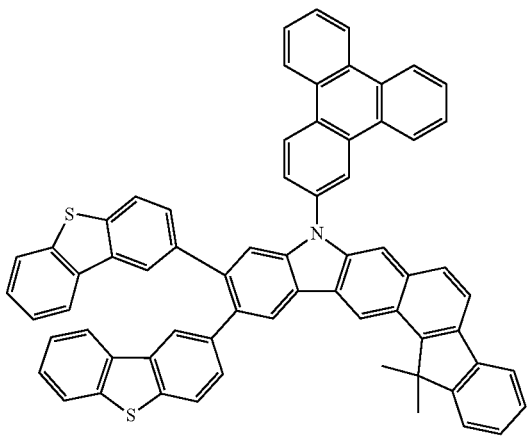

-continued
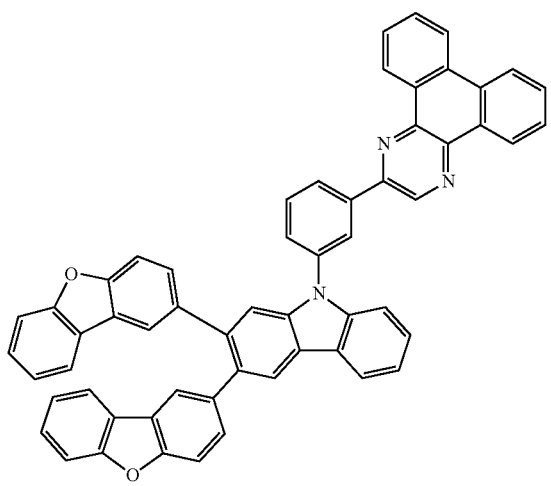
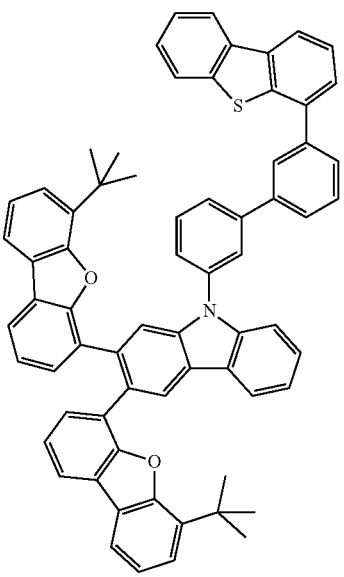
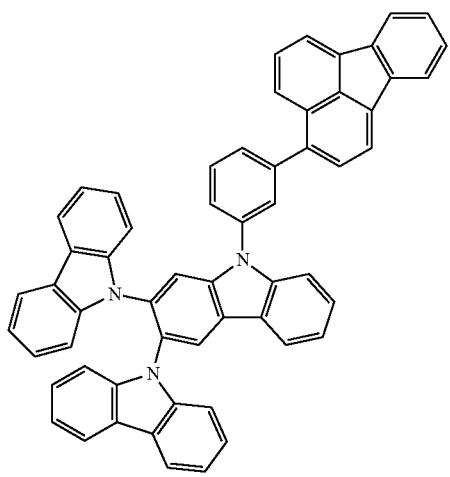
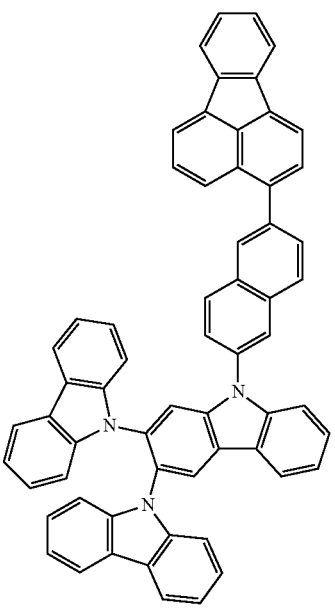
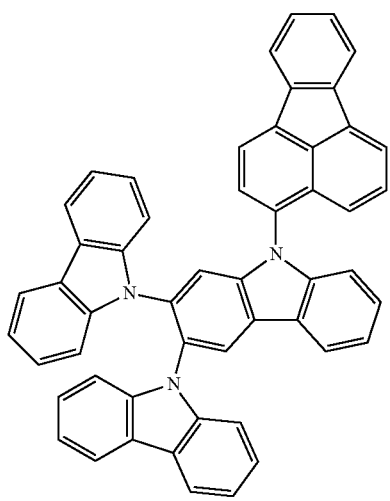
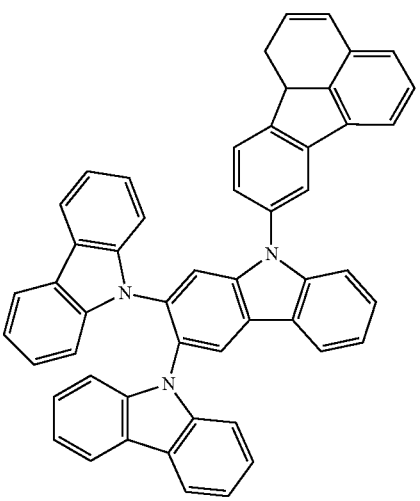

-continued
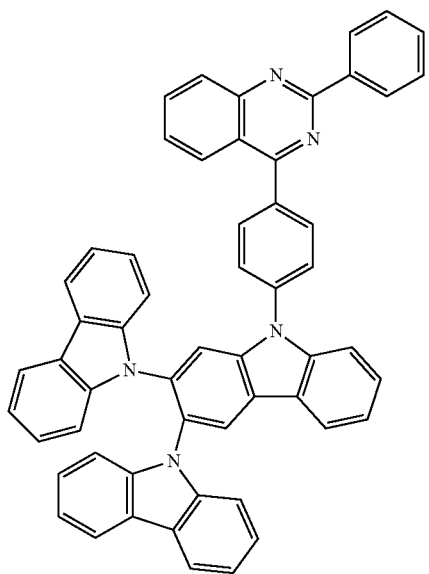
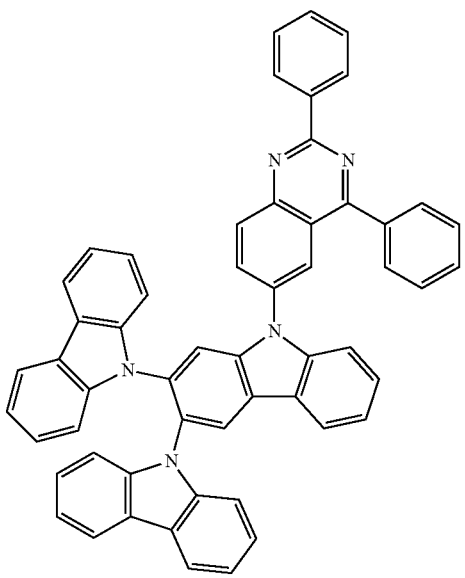
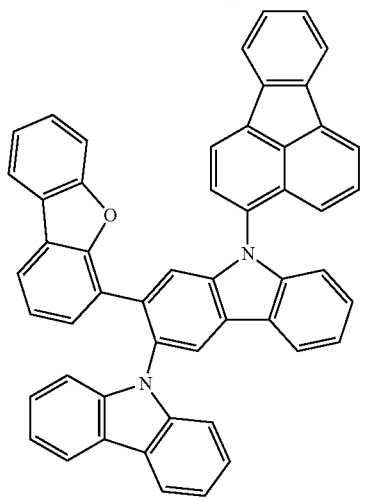
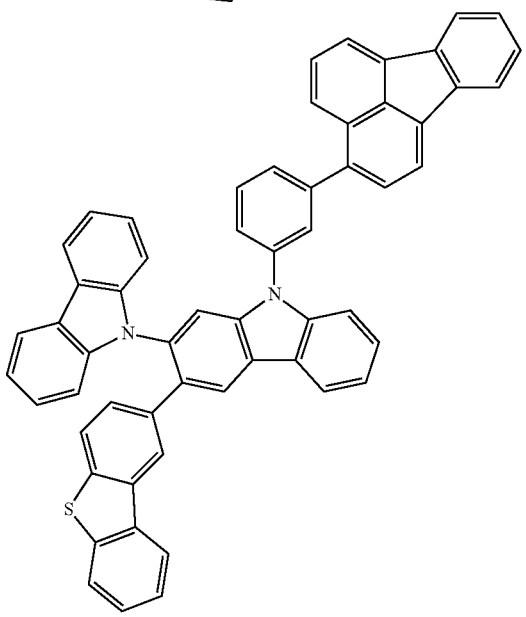
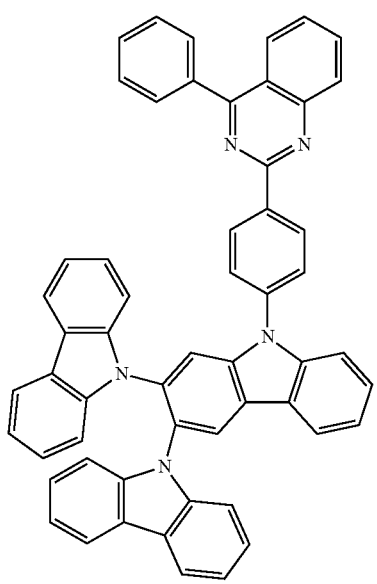

Organic EL Device

The organic EL device in an aspect of the invention will be described below.

The organic EL device comprises an organic thin film layer between a cathode and an anode. The organic thin film layer comprises a light emitting layer and at least one layer of the organic thin film layer comprises the material for organic EL devices described above.

Examples of the organic thin film layer comprising the material for organic EL devices include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The material for organic EL devices may be used in any of the above layers, for example, used in a light emitting layer of a fluorescent emission unit as a host material or a dopant material, in a light emitting layer of a phosphorescent emitting unit as a host material, or in a hole transporting layer, an electron transporting layer, etc. of an emission unit.

The organic EL device in an aspect of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more phosphorescent emitting layers and two or more phosphorescent emitting layers. A space layer may be disposed between light emitting layers to prevent the diffusion of excitons generated in a phosphorescent emitting layer into a phosphorescent emitting layer. Representative layered structures of the emission unit are shown below:
(a) hole transporting layer/light emitting layer (/electron transporting layer);
(b) hole transporting layer/first phosphorescent emitting layer/second phosphorescent emitting layer (/electron transporting layer);
(c) hole transporting layer/phosphorescent emitting layer/space layer/phosphorescent emitting layer (/electron transporting layer);
(d) hole transporting layer/first phosphorescent emitting layer/second phosphorescent emitting layer/sp ace layer/phosphorescent emitting layer (/electron transporting layer);
(e) hole transporting layer/first phosphorescent emitting layer/space layer/second phosphorescent emitting layer/sp ace layer/phosphorescent emitting layer (/electron transporting layer);
(f) hole transporting layer/phosphorescent emitting layer/space layer/first phosphorescent emitting layer/second phosphorescent emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/phosphorescent emitting layer/triplet blocking layer (/electron transporting layer).

The emission color of a phosphorescent emitting layer and that of a phosphorescent emitting layer may be different. For example, the layered structure of the laminated light emitting layer (d) may be hole transporting layer/first phosphorescent emitting layer (red)/second phosphorescent emitting layer (green)/space layer/phosphorescent emitting layer (blue)/electron transporting layer.

An electron blocking layer may be disposed between a light emitting layer and a hole transporting layer or between a light emitting layer and a space layer, if necessary. Also, a hole blocking layer may be disposed between a light emitting layer and a electron transporting layer, if necessary. With such an electron blocking layer or a hole blocking layer, electrons and holes are confined in a light emitting layer to increase the degree of charge recombination in the light emitting layer, thereby improving the lifetime.

A representative device structure of the tandem-type organic EL device is shown below:
(2) Anode/First Emission Unit/Intermediate Layer/Second Emission Unit/Cathode.

The layered structures of the first emission unit and the second emission unit may be independently selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by a known material capable of supplying electrons to the first emission unit and holes to the second emission unit.

A schematic structure of an example of the organic EL device in an aspect of the invention is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer comprising a phosphorescent host and a phosphorescent dopant (phosphorescent emitting material). A hole injecting/transporting layer (an anode-side organic thin film layer) 6 may be disposed between the light emitting layer 5 and the anode 3, and an electron injecting/transporting layer (a cathode-side thin film layer) 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not necessarily mean a material that cannot be used as a material for a fluorescent emitting layer. The same applies to the fluorescent host.

Substrate

The organic EL device in an aspect of the invention is formed on a light-transmissive substrate. The light-transmissive substrate serves as a support for the organic EL device and is preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of organic EL device injects holes to a hole transporting layer or a light emitting layer, and an anode having a work function of 4.5 eV or more is effective. Examples of the material for anode include indium tin oxide alloy (ITO), tin oxide (NESA), indium zinc oxide alloy, gold, silver, platinum, and cupper. The anode is formed by making the material for anode into a thin film by a method, such as a vapor deposition method or a sputtering method. When getting the light emitted from a light emitting layer through the anode, the transmittance of anode to visible light is preferably 10% or more. The sheet resistance of anode is preferably several hundreds Ω/or less. The film thickness of anode depends upon the kind of material and generally 10 nm to 1 μm, preferably 10 to 200 nm.

Cathode

The cathode injects electrons to an electron injecting layer, an electron transporting layer or a light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material for cathode into a thin film by a method, such as a vapor deposition method and a sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons within a light emitting layer. The dopant material causes the excitons generated by recombination to emit light efficiently.

In a phosphorescent device, the major function of the host material is to confine the excitons generated on the dopant within a light emitting layer.

To control the carrier balance in a light emitting layer, the light emitting layer may be made into a double host (host/co-host) layer, for example, by combinedly using an electron transporting host and a hole transporting host.

The light emitting layer may be also made into a double dopant layer, in which two or more kinds of dopant materials having a high quantum yield are combinedly used and each dopant material emits light with its own color. For example, a yellow emission can be obtained by a light emitting layer which is formed by co-depositing a host, a red-emitting dopant, and a green-emitting dopant.

In a laminate of two or more light emitting layers, electrons and holes can be accumulated in the interface between the light emitting layers, and therefore, the recombination region is localized in the interface between the light emitting layers. With this structure, the quantum efficiency can be enhanced.

The easiness of hole injection to a light emitting layer and the easiness of electron injection to a light emitting layer may be different from each other. Also, the hole transporting ability and the electron transporting ability each being expressed by mobility of holes and electrons in a light emitting layer may be different from each other.

The phosphorescent dopant (phosphorescent emitting material) to be used in a light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of luminescent device, a metal complex comprising a metal selected from Ir, Os, and Pt is preferred, with a metal complex, such as an iridium complex, an osmium complex and a platinum complex, particularly an ortho-metallated complex being more preferred, an iridium complex and a platinum complex being still more preferred, and an ortho-metallated iridium complex being particularly preferred.

The content of the phosphorescent dopant in a light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex for the phosphorescent dopant are shown below.

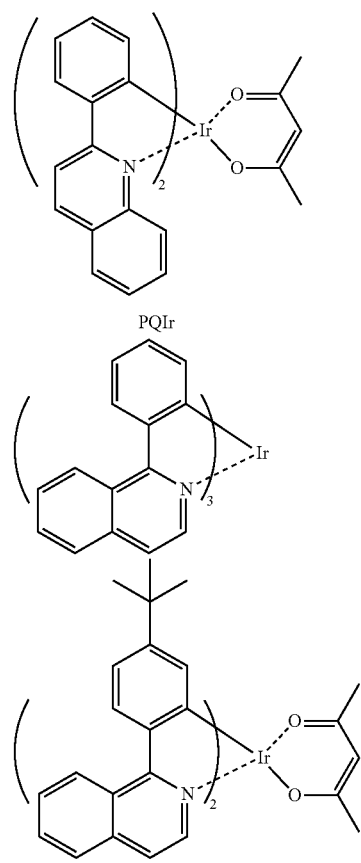

PQIr

-continued
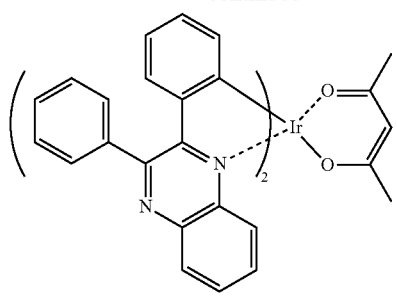
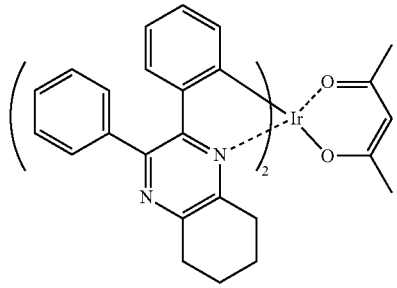
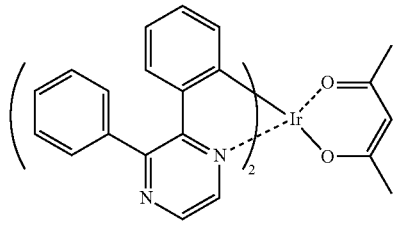
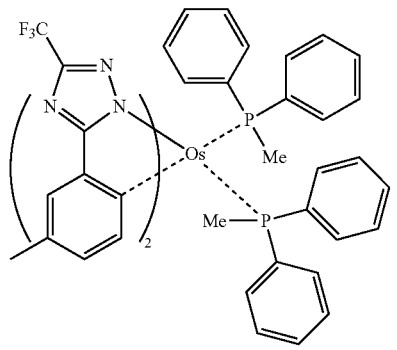
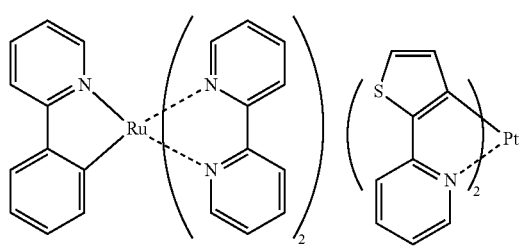
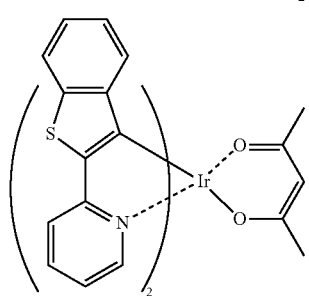
-continued
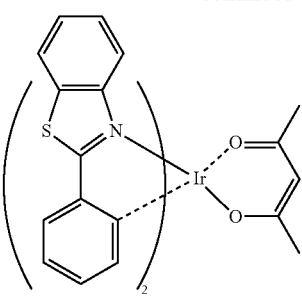
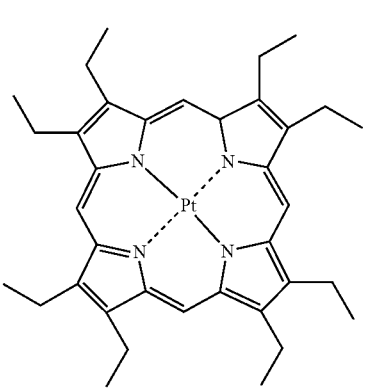
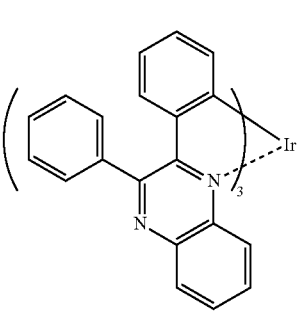
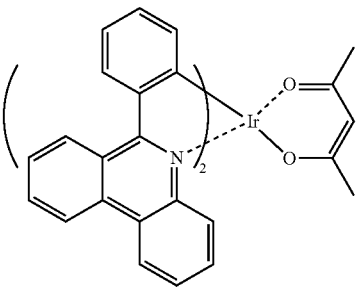
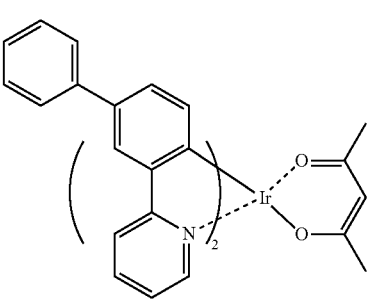

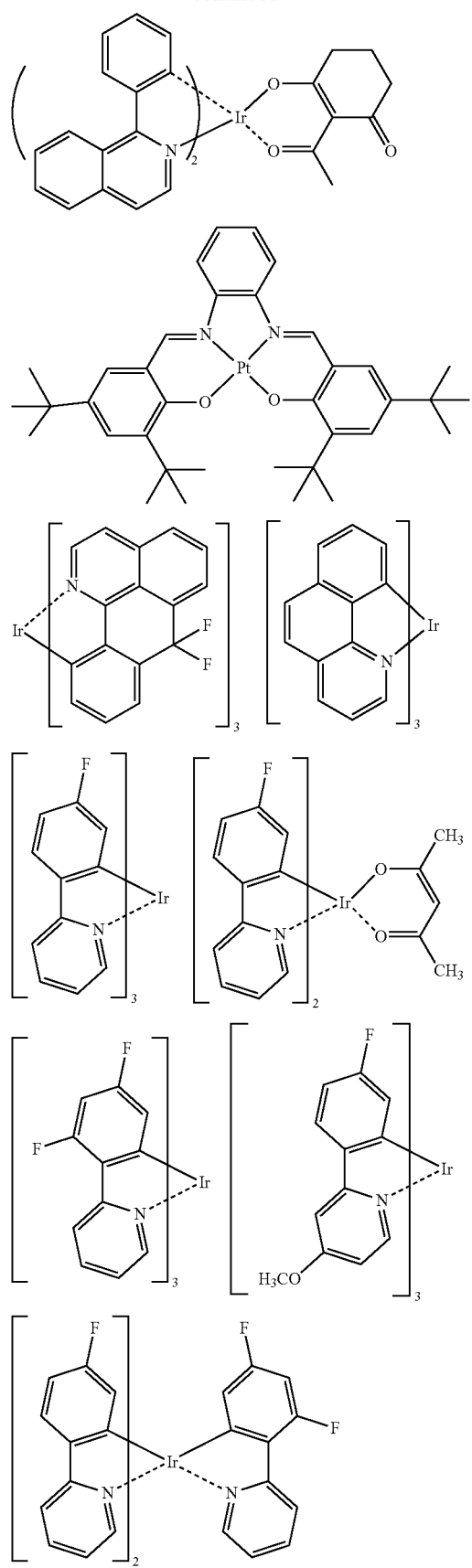
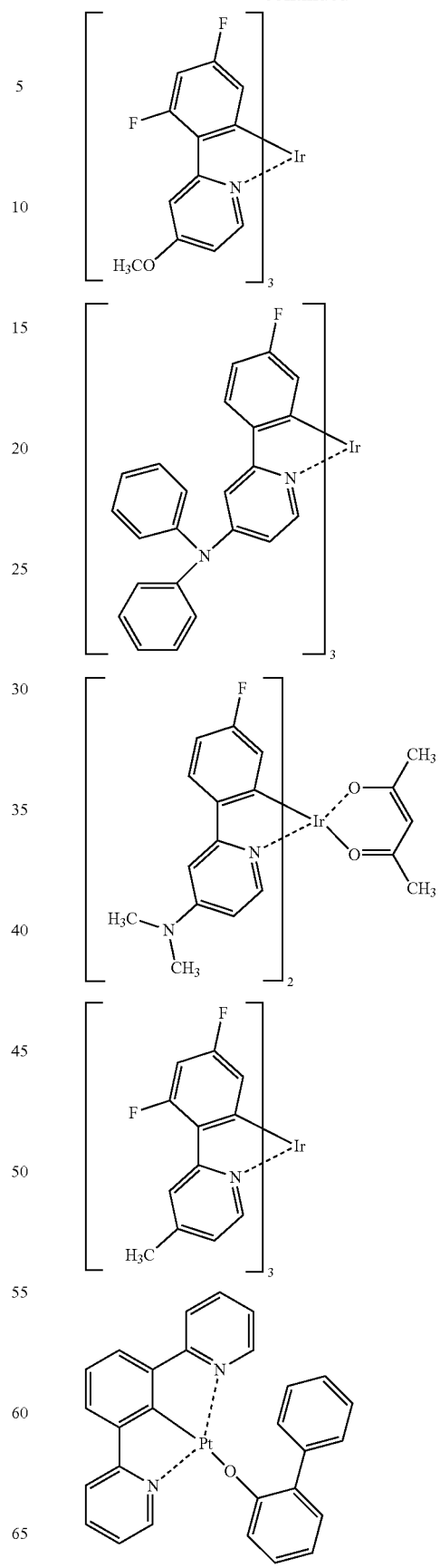

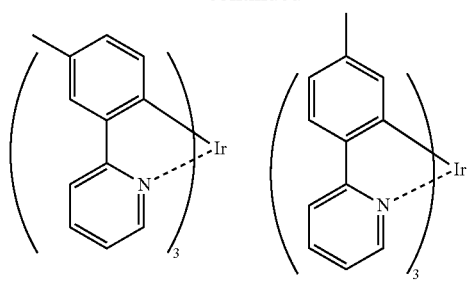
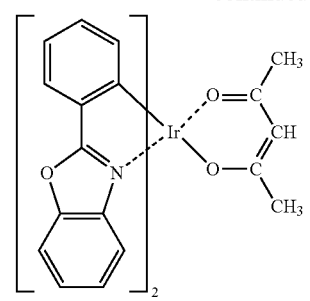
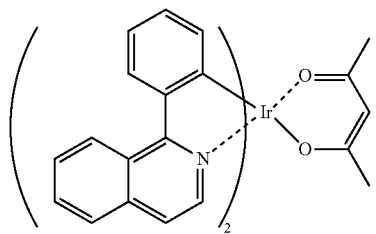
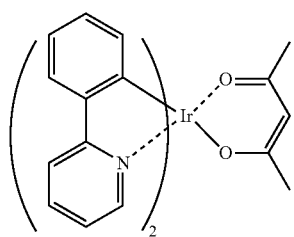
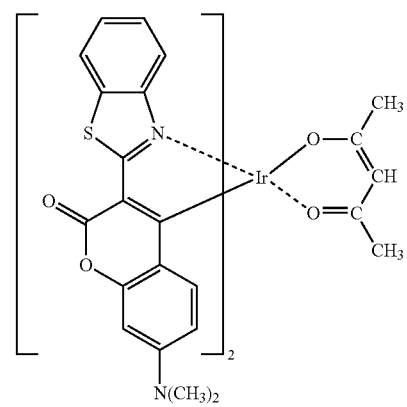
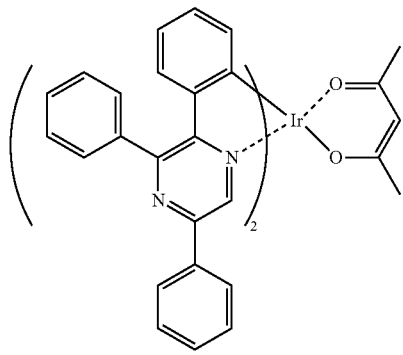
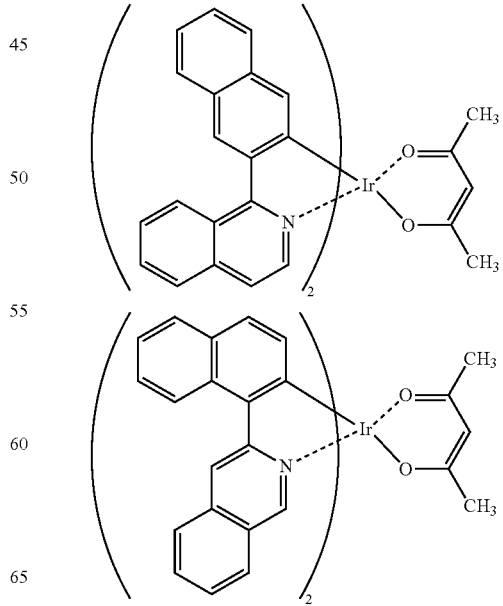
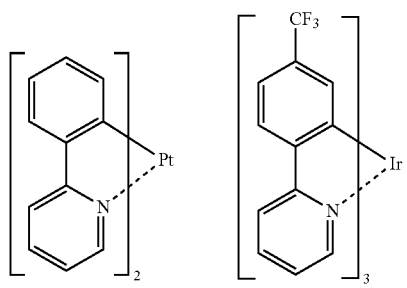
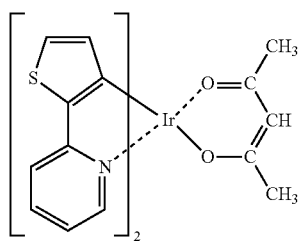
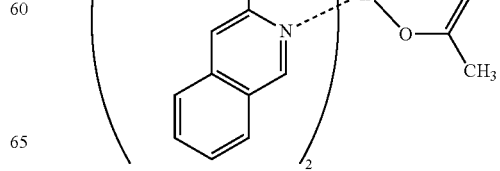

-continued
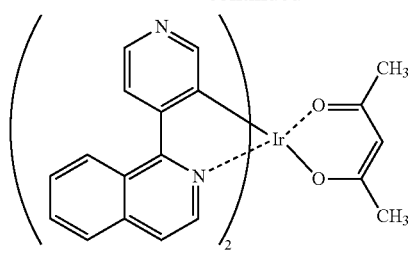
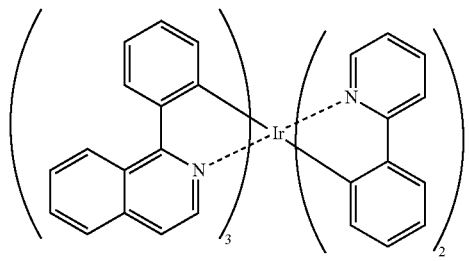
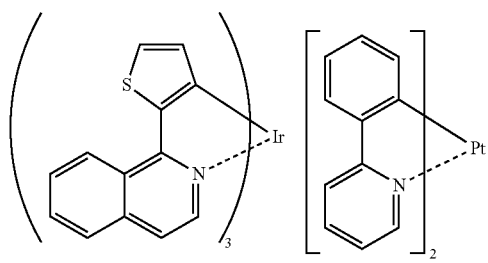
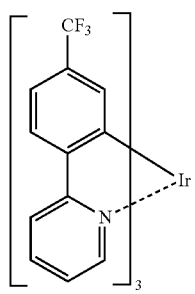
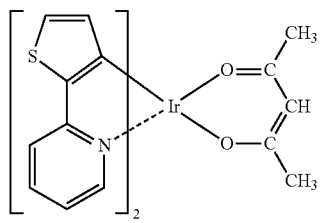
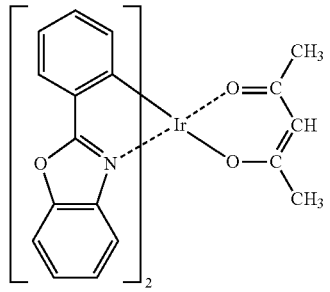
-continued
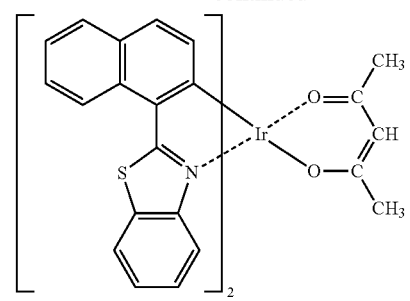
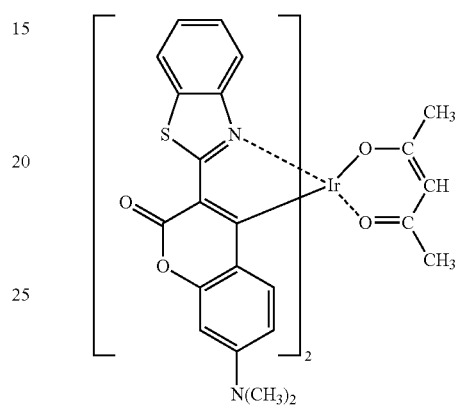
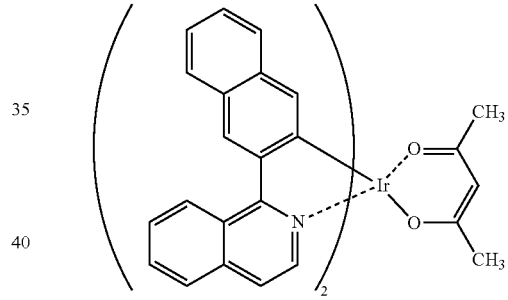
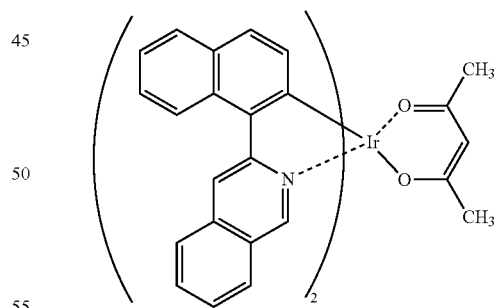
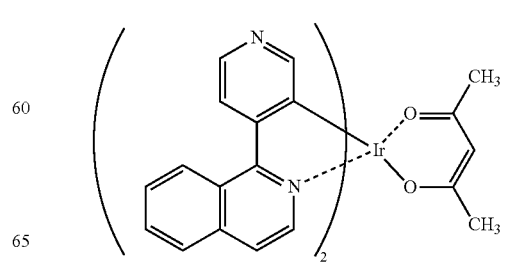

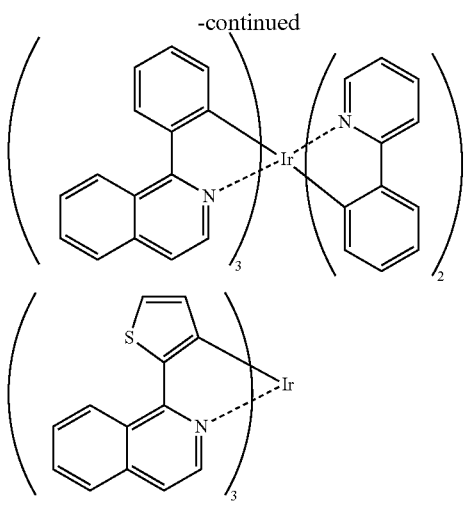

A complex represented by formula (X) is also preferred as the phosphorescent dopant:

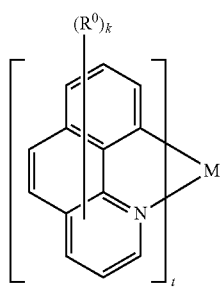

(X)

wherein each $R^0$ independently represents a hydrogen atom or a substituent, k is an integer of 1 to 8, t is an integer of 2 to 4, and M is Ir, Os, or Pt.

Examples of the substituent represented by $R^0$ include those mentioned above with respect to formula (1).

The phosphorescent host is a compound which confines the triplet energy of the phosphorescent dopant efficiently within a light emitting layer to cause the phosphorescent dopant to emit light efficiently. Although the carbazole derivative and the material for organic EL device each in an aspect of the invention are useful as a phosphorescent host, a compound other than the material for organic EL device may be used as the phosphorescent host according to the use of the device. The use of the material for organic EL device in an aspect of the invention is not limited to the use as the phosphorescent host mentioned above.

The material for organic EL device in an aspect of the invention and a compound other than it may be combinedly used in the same light emitting layer as the phosphorescent host materials. Alternatively, the material for organic EL device in an aspect of the invention can be used in one of light emitting layers as a phosphorescent host material and a compound other than it can be used in another of the light emitting layers as a phosphorescent host material. The material for organic EL device in an aspect of the invention may be used in an organic layer other than the light emitting layer. In this case, a compound other than the material for organic EL device may be used as a phosphorescent host of the light emitting layer.

Examples of the compound other than the material for organic EL devices in an aspect of the invention, which is suitable as a phosphorescent host, include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below.

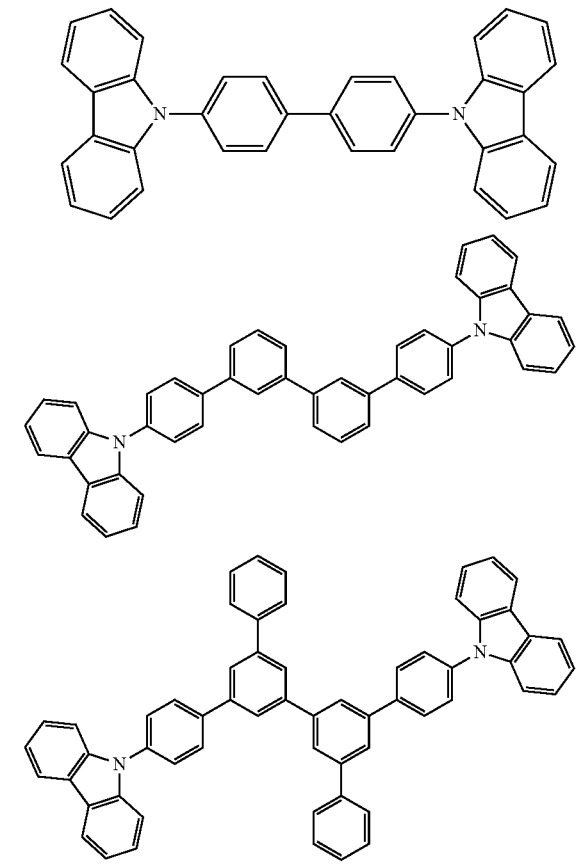

-continued

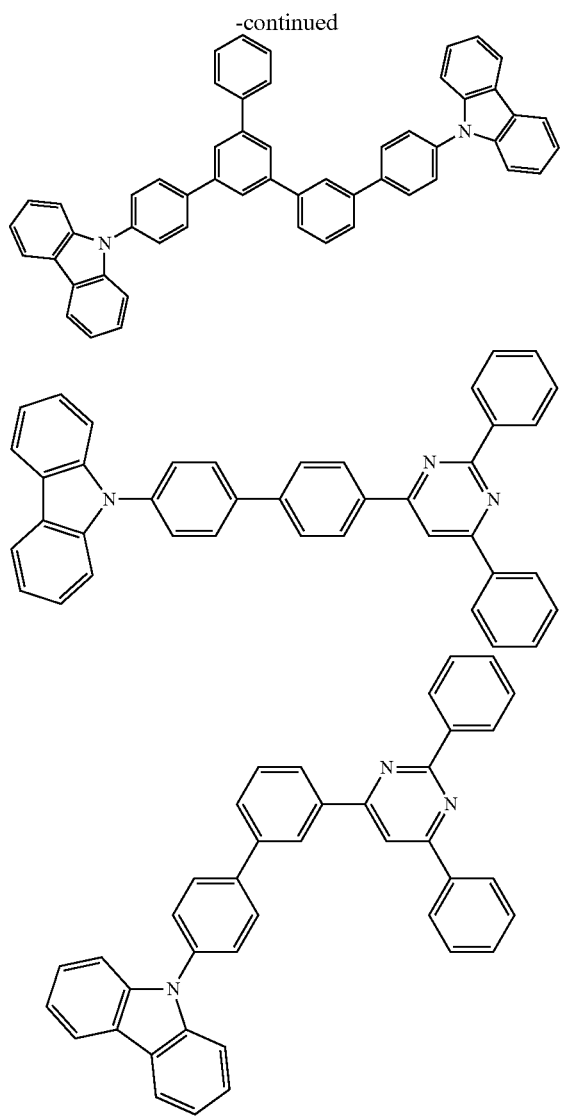

The organic EL device in an aspect of the invention may comprise a light emitting layer comprising a fluorescent material, i.e., a fluorescent emitting layer. The fluorescent emitting layer may be formed from a known fluorescent emitting material, for example, at least one material selected from an anthracene derivative, a fluoranthene derivative, a styrylamine derivative, and an arylamine derivative, with the anthracene derivative and the arylamine derivative being more preferred. In particular, the anthracene derivative is preferably used as a host material and the arylamine derivative is preferably used as a dopant. The materials described in WO 2010/134350 and WO 2010/134352 are preferably used. The material for organic EL device in an aspect of the invention may be used in a fluorescent emitting layer as a fluorescent emitting material or a host material.

Electron-Donating Dopant

The organic EL device in an aspect of the invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include an alkali oxide, such as $Li_2O$, $Cs_2O$, and $K_2O$, and an alkali halide, such as LiF, NaF, CsF, and KF, with LiF, $Li_2O$, and NaF being preferred. Examples of the alkaline earth metal compound include BaO, SrO, CaO, and a mixture thereof, such as $Ba_xSr_{1-x}O$ (0<x<1) and $Ba_xCa_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, the alkaline earth metal complex, and the rare earth metal are not particularly limited as long as containing at least one metal ion selected from an alkali metal ion, an alkaline earth metal ion, and a rare earth metal ion, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivatives thereof.

The electron-donating dopant is added to the interfacial region preferably into a form of layer or island preferably by co-depositing the electron-donating dopant together with an organic compound for forming the interfacial region (a light emitting material, an electron injecting material, etc.) by a resistance heating deposition method, thereby dispersing the electron-donating dopant into the organic compound. The disperse concentration expressed by the molar ratio of the organic compound and the electron-donating dopant is 100:1 to 1:100 and preferably 5:1 to 1:5.

When the electron-donating dopant is formed into a form of layer, a light emitting material or an electron injecting material is made into a layer to form an interfacial organic layer, and then, the electron-donating dopant alone is deposited by a resistance heating deposition method into a layer having a thickness of preferably 0.1 to 15 nm. When the electron-donating dopant is formed into a form of island, a light emitting material or an electron injecting material is made into a form of island to form an interfacial organic layer, and then, the electron-donating dopant alone is deposited by a resistance heating deposition method into a form of island having a thickness of preferably 0.05 to 1 nm.

The molar ratio of the main component and the electron-donating dopant in the organic EL device in an aspect of the invention is preferably 5:1 to 1:5 and more preferably 2:1 to 1:2.

Electron Transporting Layer

The electron transporting layer is an organic layer disposed between a light emitting layer and a cathode and transports electrons from the cathode to the light emitting layer. If two or more electron transporting layers are provided, the organic layer closer to the cathode may be defined as an electron injecting layer in some cases. The electron injecting layer injects electrons from the cathode to the organic layer unit efficiently. The carbazole derivative and the material for organic EL devices in an aspect of the invention may be used in the electron transporting layer (second charge transporting layer) as an electron transporting material.

An aromatic heterocyclic compound having one or more heteroatoms in its molecule is preferably used as an electron transporting material for use in the electron transporting layer, and a nitrogen-containing ring derivative is particularly preferred. The nitrogen-containing ring derivative is preferably an aromatic ring compound having a nitrogen-containing 6- or 5-membered ring, or a fused aromatic ring compound having a nitrogen-containing 6- or 5-membered ring.

The nitrogen-containing ring derivative is preferably a metal chelate complex having a nitrogen-containing ring represented by formula (A):

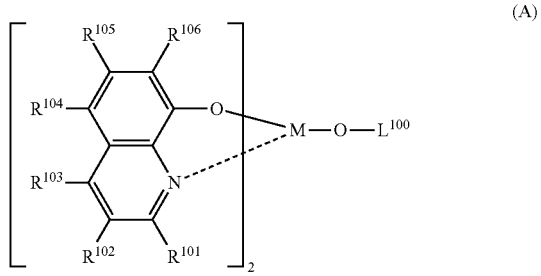

(A)

wherein $R^{101}$ to $R^{105}$ each independently represent a hydrogen atom, a heavy hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heterocyclic group having 5 to 50 ring carbon atoms, each optionally having a substituent.

The halogen atom may include fluorine, chlorine, bromine, and iodine.

The substituted amino group may include an alkylamino group, an arylamino group, and an aralkylamino group.

The alkylamino group and the aralkylamino group are represented by —NQ$^1$Q$^2$. Q$^1$ and Q$^2$ each independently represent an alkyl group having 1 to 20 carbon atoms or an aralkyl group having 1 to 20 carbon atoms. One of Q$^1$ and Q$^2$ may be a hydrogen atom or a heavy hydrogen atom.

The arylamino group is represented by —NAr$^{1'}$Ar$^{2'}$, wherein Ar$^{1'}$ and Ar$^{2'}$ each independently represent a non-fused aromatic hydrocarbon group or a fused aromatic hydrocarbon group, each having 6 to 50 carbon atoms. One of Ar$^{1'}$ and Ar$^{2'}$ may be a hydrogen atom or a heavy hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by —COOY', wherein Y' is an alkyl group having 1 to 20 carbon atoms.

M is aluminum (Al), gallium (Ga), or indium (In), with In being preferred.

L$^{100}$ is a group represented by formula (A') or (A"):

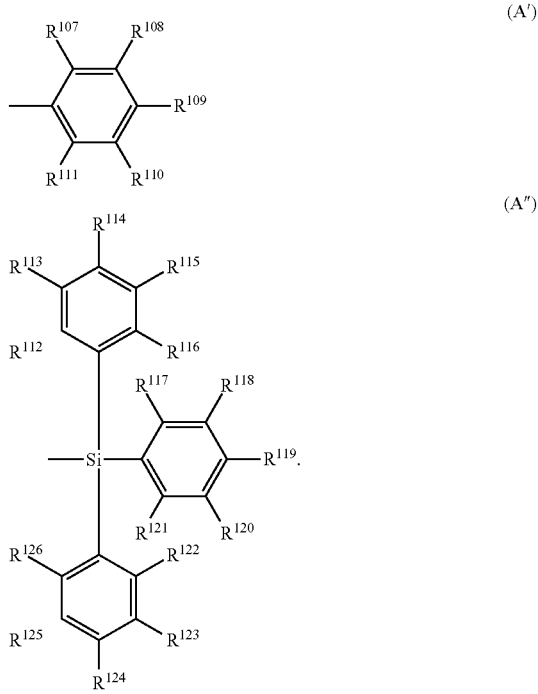

$R^{107}$ to $R^{111}$ of formula (A') each independently represent a hydrogen atom, a heavy hydrogen atom or a substituted or unsubstituted hydrocarbon group having 1 to 40 carbon atoms, wherein groups adjacent to each other may form a ring structure. $R^{112}$ to $R^{126}$ of formula (A") each independently represent a hydrogen atom, a heavy hydrogen atom or a substituted or unsubstituted hydrocarbon group having 1 to 40 carbon atoms, wherein groups adjacent to each other may form a ring structure.

Examples of the hydrocarbon group having 1 to 40 carbon atoms for $R^{107}$ to $R^{126}$ of formulae (A') and (A") are the same as those described above with respect to $R^{101}$ to $R^{106}$ of formula (A). Examples of the divalent group formed by adjacent groups selected from $R^{107}$ to $R^{111}$ which complete a ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

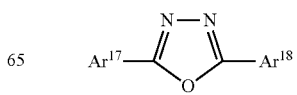

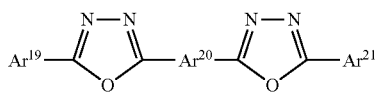

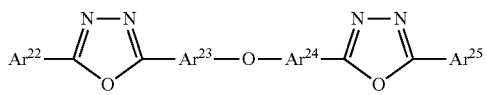

wherein $Ar^{17}$, $Ar^{18}$, $Ar^{19}$, $Ar^{21}$, $Ar^{22}$, and $Ar^{25}$ are each a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different, respectively. Examples of the aromatic hydrocarbon group and the fused aromatic hydrocarbon group include a phenyl group, a naphthyl group, a biphenyl group, an anthranyl group, a perylenyl group, and a pyrenyl group. The optional substituent may be an alkyl group having 1 to 10 carbon atoms, an alkoxyl group having 1 to 10 carbon atoms or a cyano group.

$Ar^{20}$, $Ar^{23}$, and $Ar^{24}$ are each a substituted or unsubstituted divalent aromatic hydrocarbon group or a substituted or unsubstituted divalent fused aromatic hydrocarbon group each having 6 to 50 carbon atoms, and $Ar^{23}$ and $Ar^{24}$ may be the same or different. Examples of the divalent aromatic hydrocarbon group or the divalent fused aromatic hydrocarbon group include a phenylene group, a naphthylene group, a biphenylene group, an anthranylene group, a perylenylene group, and a pyrenylene group. The optional substituent may be an alkyl group having 1 to 10 carbon atoms, an alkoxyl group having 1 to 10 carbon atoms or a cyano group.

An electron transporting compound which has a good thin film-forming property is preferably used. Examples thereof are shown below.

Examples of the nitrogen-containing heterocyclic derivative for use as the electron transporting compound include a nitrogen-containing heterocyclic derivative having the following formulae but exclusive of a metal complex, for example, a compound having a 5- or 6-membered ring which includes a skeleton represented by formula (B) or having a structure represented by formula (C):

wherein $X_1$ is a carbon atom or a nitrogen atom and $Z_1$ and $Z_2$ each independently represent a group of atoms for completing the nitrogen-containing heterocyclic ring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of formulae (B) and (C) or a combination of formulae (B) and (D):

The nitrogen-containing group of the nitrogen-containing aromatic polycyclic compound is selected, for example, from the nitrogen-containing heterocyclic groups shown below:

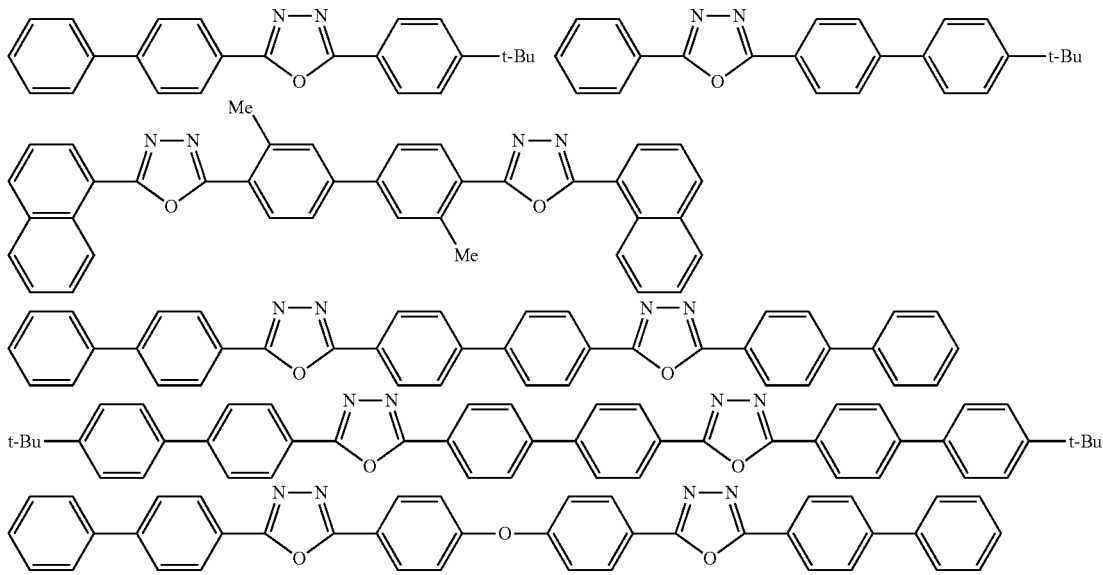

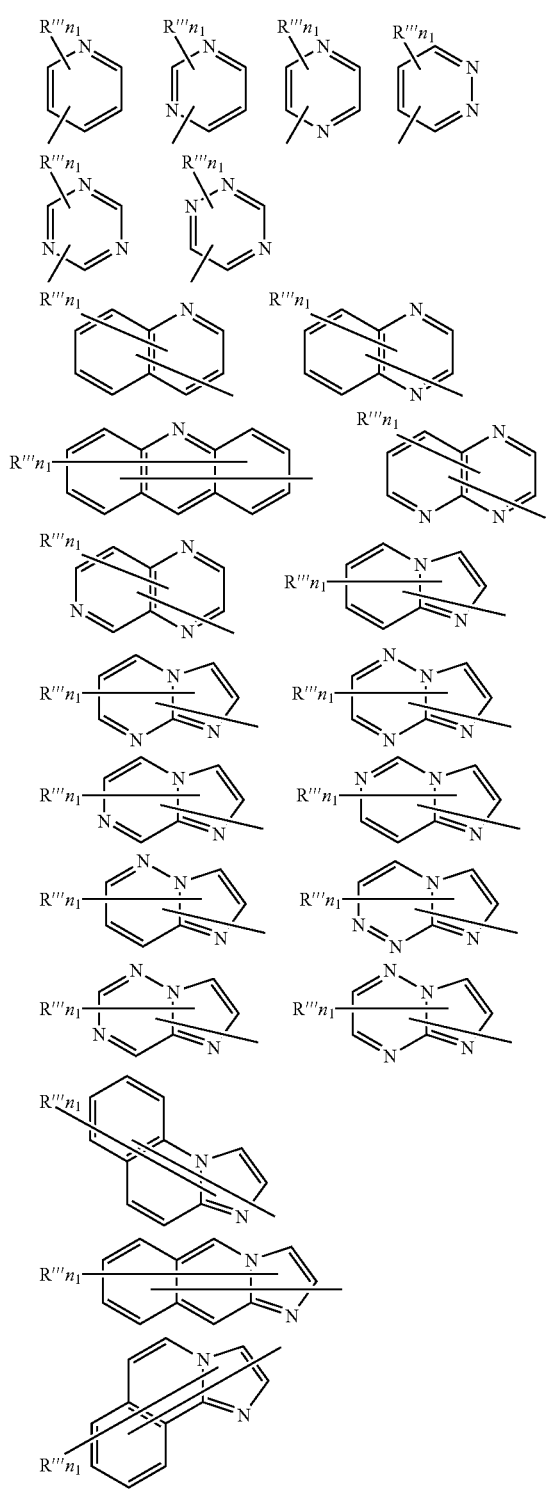

wherein R''' is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; $n_1$ is an integer of 0 to 5; and when $n_1$ is an integer of 2 or more, groups R''' may be the same or different.

A nitrogen-containing heterocyclic derivative represented by formula (D1) is also preferred:

$$\text{HAr-L}^{101}\text{-A}^{101}\text{-Ar}^{102} \tag{D1}$$

wherein HAr is a substituted or unsubstituted nitrogen-containing heterocyclic group having 3 to 40 carbon atoms; $L^{101}$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^{101}$ is a substituted or unsubstituted divalent aromatic hydrocarbon group having 6 to 40 carbon atoms; and $Ar^{102}$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

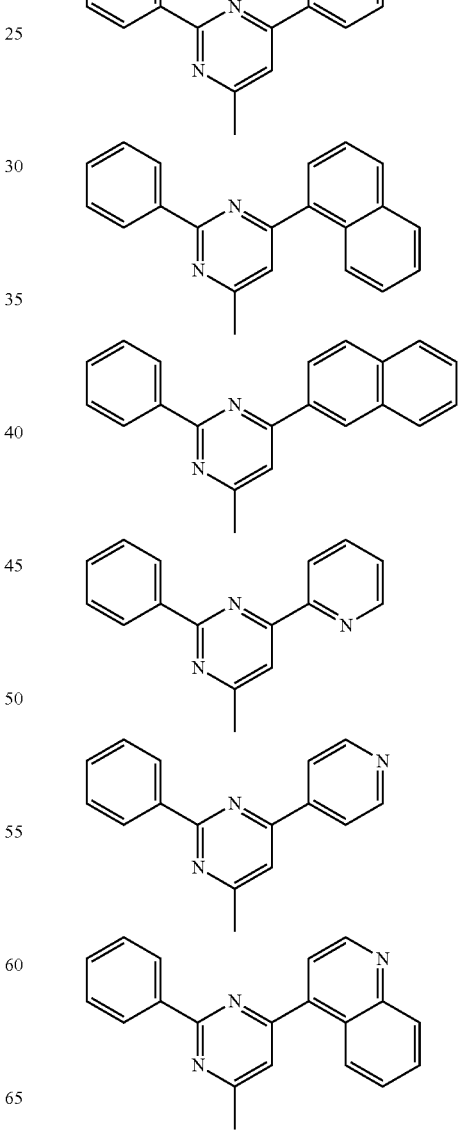

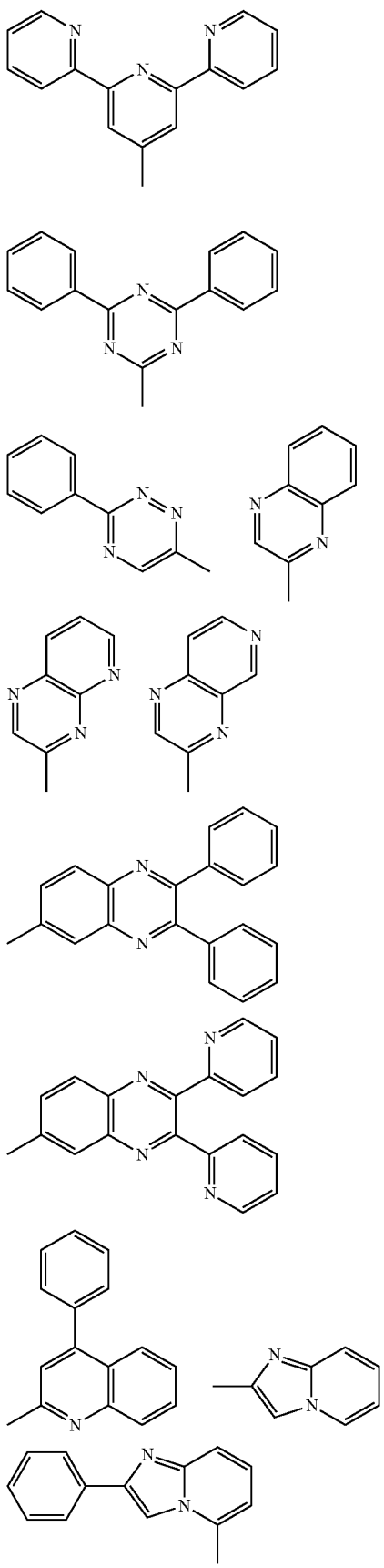

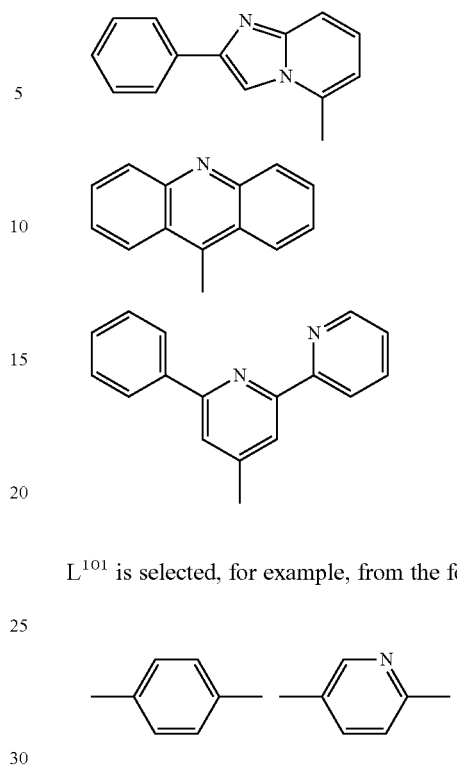

$L^{101}$ is selected, for example, from the following groups:

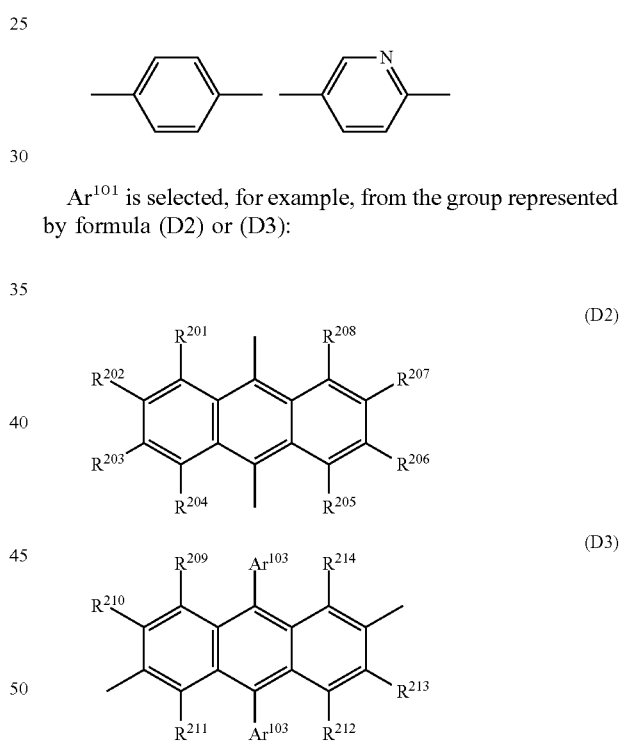

$Ar^{101}$ is selected, for example, from the group represented by formula (D2) or (D3):

$$\text{(D2)}$$
$$\text{(D3)}$$

wherein $R^{201}$ to $R^{214}$ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar^{103}$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

$Ar^{102}$ is selected, for example, from the following groups:

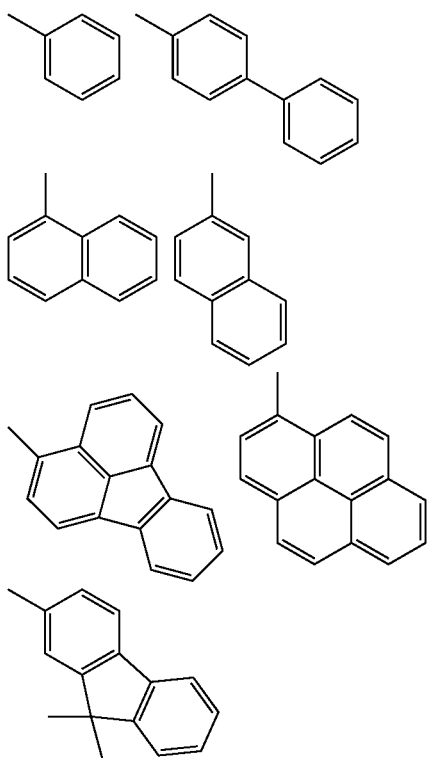

In addition, the following compound is preferably used as the nitrogen-containing aromatic polycyclic compound for use as the electron transporting compound:

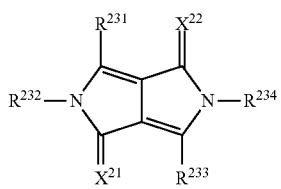

(D4)

wherein $R^{211}$ to $R^{214}$ each independently represent a hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X^{21}$ and $X^{22}$ each independently represent an oxygen atom, a sulfur atom, or a dicyanomethylene group.

Further, the following compound is also suitable as the electron transporting compound:

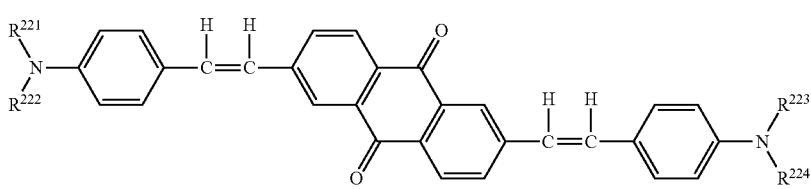

(D5)

wherein $R^{221}$, $R^{222}$, $R^{223}$, and $R^{224}$ may be the same or different and each represent an aromatic hydrocarbon group or a fused aromatic hydrocarbon group each represented by formula (D6):

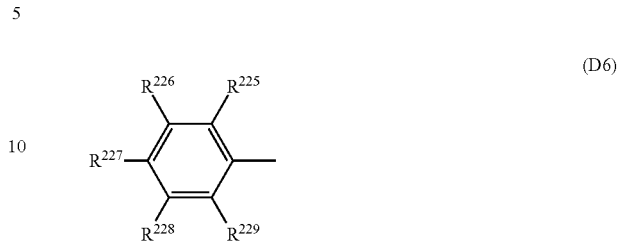

(D6)

wherein $R^{225}$, $R^{226}$, $R^{227}$, $R^{228}$, and $R^{229}$ may be the same or different and each represent a hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms; and at least one selected from $R^{225}$, $R^{226}$, $R^{227}$, $R^{228}$, and $R^{229}$ represents a group other than a hydrogen atom.

Further, a polymer including the nitrogen-containing heterocyclic group or the nitrogen-containing heterocyclic derivative is also usable as the electron transporting compound.

The electron transporting layer of the organic EL device in an aspect of the invention preferably comprises at least one compound selected from the nitrogen-containing heterocyclic derivatives represented by formulae (E) to (G):

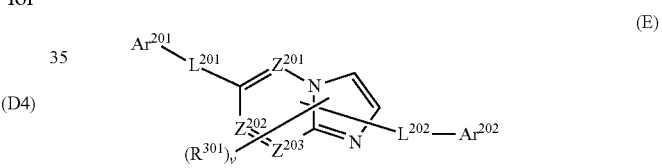

(E)

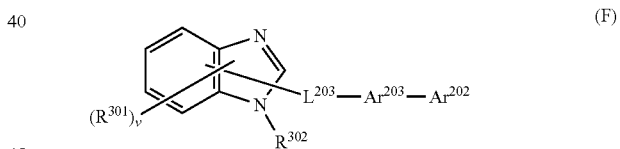

(F)

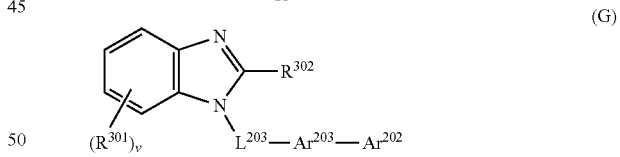

(G)

wherein $Z^{201}$, $Z^{202}$ and $Z^{203}$ each independently represent a nitrogen atom or a carbon atom;

$R^{301}$ and $R^{302}$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxy group having 1 to 20 carbon atoms;

v is an integer of 0 to 5, when v is an integer of 2 or more, groups $R^{301}$ may be the same or different, and adjacent two groups $R^{301}$ may bond to each other to form a substituted or unsubstituted hydrocarbon ring;

$Ar^{201}$ represents a substituted or unsubstituted aryl group having 6 to 50 ring carbon atoms or a substituted or unsubstituted heteroaryl group having 5 to 50 ring atoms;

$Ar^{202}$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxy group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^{201}$ and $Ar^{202}$ is a substituted or unsubstituted fused aromatic hydrocarbon ring group having 10 to 50 ring carbon atoms or a substituted or unsubstituted fused aromatic heterocyclic group having 9 to 50 ring atoms;

$Ar^{203}$ represents a substituted or unsubstituted arylene group having 6 to 50 ring carbon atoms or a substituted or unsubstituted heteroarylene group having 5 to 50 ring atoms; and $L^{201}$, $L^{202}$, and $L^{203}$ each independently represent a single bond, a substituted or unsubstituted arylene group having 6 to 50 ring carbon atoms or a substituted or unsubstituted divalent fused aromatic heterocyclic group having 9 to 50 ring atoms.

Examples of the aryl group having 6 to 50 ring carbon atoms include a phenyl group, a naphthyl group, an anthryl group, a phenanthryl group, a naphthacenyl group, a chrysenyl group, pyrenyl group, a biphenyl group, a terphenyl group, a tolyl group, a fluoranthenyl group, and a fluorenyl group.

Examples of the heteroaryl group having 5 to 50 ring atoms include a pyrrolyl group, a furyl group, a thiophenyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, and an imidazo[1,2-a]pyrimidinyl.

Examples of the alkyl group having 1 to 20 carbon atoms include a methyl group, an ethyl group, a propyl group, a butyl group, a pentyl group, and a hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxy group having 1 to 20 carbon atoms include the alkyl group mentioned above.

Examples of the arylene groups include the groups obtained by removing one hydrogen atom from the aryl group mentioned above.

Examples of the divalent fuse aromatic heterocyclic group having 9 to 50 ring atoms include the groups obtained by removing one hydrogen atom from the fused aromatic heterocyclic group mentioned above with respect to the heteroaryl group.

The thickness of the electron transporting layer is preferably 1 to 100 nm, but not particularly limited thereto.

The electron injecting layer optionally formed adjacent to the electron transporting layer preferably comprises an inorganic compound, such as an insulating material and a semiconductor, in addition to the nitrogen-containing ring derivative. The electron injecting layer comprising the insulating material or the semiconductor effectively prevents the leak of electric current to enhance the electron injecting properties.

The insulating material is preferably at least one metal compound selected from the group consisting of an alkali metal chalcogenide, an alkaline earth metal chalcogenide, an alkali metal halide and an alkaline earth metal halide. The electron injecting properties of the electron injecting layer are further enhanced when the alkali metal chalcogenide, etc. is used in the electron injecting layer. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of preferred alkaline earth metal halide include fluorides, such as $CaF_2$, $BaF_2$, $SrF_2$, $MgF_2$ and $BeF_2$, and halides other than fluorides.

Examples of the semiconductor include an oxide, a nitride and an oxynitride of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. The electron injecting layer formed from such an insulating thin film decreases the pixel defects, such as dark spots, because the insulating thin film is highly uniform. Examples of such an inorganic compound include the alkali metal chalcogenide, the alkaline earth metal chalcogenide, the alkali metal halide and the alkaline earth metal halide.

The thickness of a layer comprising the insulating material or the semiconductor is preferably about 0.1 to 15 nm. The electron injecting layer of the organic EL device in an aspect of the invention may comprise the electron-donating dopant mentioned above.

Hole Transporting Layer

The hole transporting layer is an organic layer formed between a light emitting layer and an anode and has a function of transporting holes from the anode to the light emitting layer. If two or more hole transporting layers are provided, the organic layer closer to the anode may be defined as the hole injecting layer in some cases. The hole injecting layer has a function of efficiently injecting holes from the anode to the organic layer unit. The carbazole derivative and the material for organic EL devices in an aspect of the invention may be used in the hole transporting layer (first charge transporting layer) as a hole transporting material.

Another preferred material for use in the hole transporting layer may include an aromatic amine compound, for example, an aromatic amine derivative represented by formula (H):

(H)

wherein:

$Ar^{211}$ to $Ar^{214}$ each represent a substituted or unsubstituted aromatic hydrocarbon group or fused aromatic hydrocarbon group each having 6 to 50 ring carbon atoms, a substituted or unsubstituted aromatic heterocyclic group or fused aromatic heterocyclic group each having 5 to 50 ring atoms, or a group wherein the aromatic hydrocarbon group or fused aromatic hydrocarbon group is bonded to the aromatic heterocyclic group or fused aromatic heterocyclic group; and $L^{211}$ represents a substituted or unsubstituted aromatic hydrocarbon group or fused aromatic hydrocarbon group each having 6 to 50 ring carbon atoms or a substituted or unsubstituted aromatic heterocyclic group or fused aromatic heterocyclic group each having 5 to 50 ring atoms.

Examples of the compound represented by formula (H) are shown below.

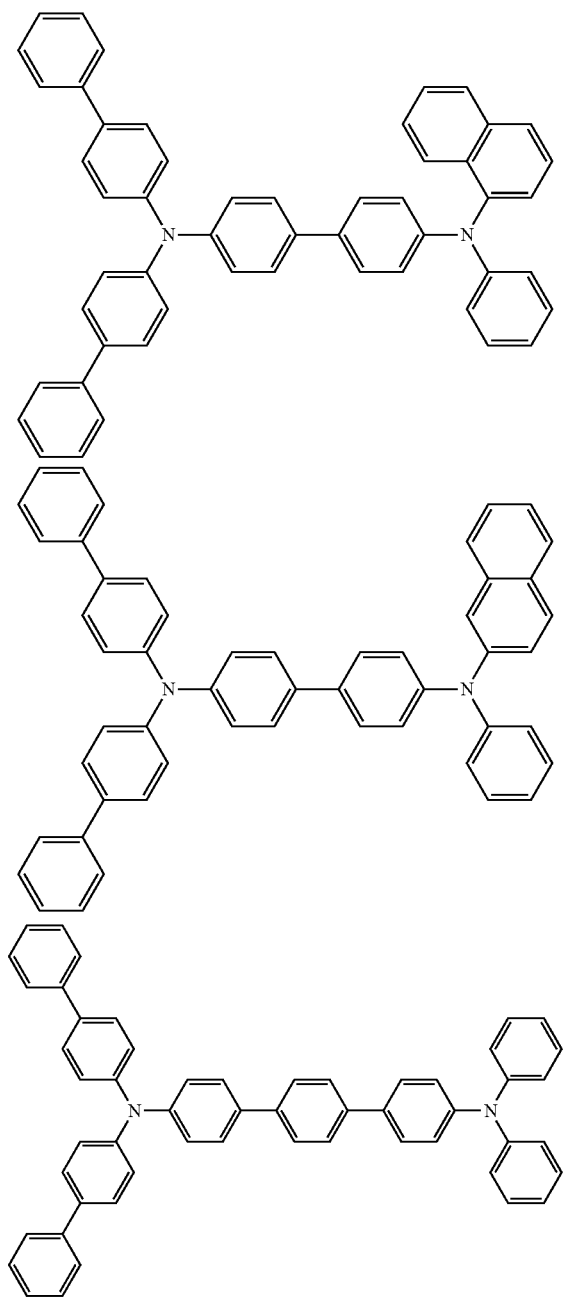

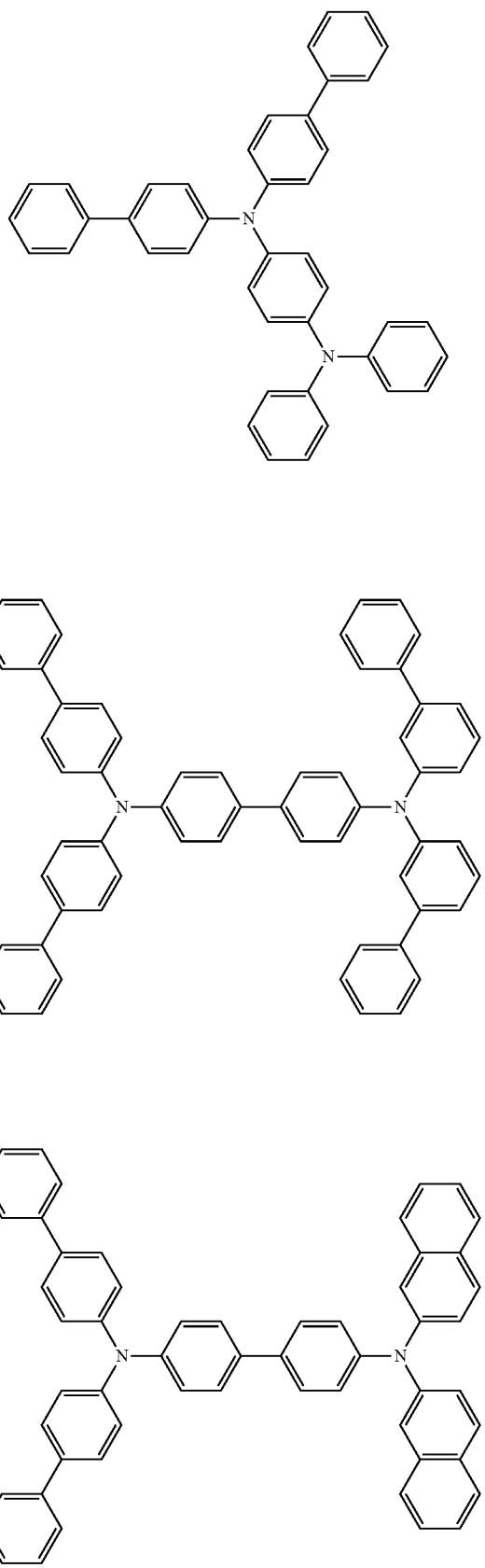

71
-continued
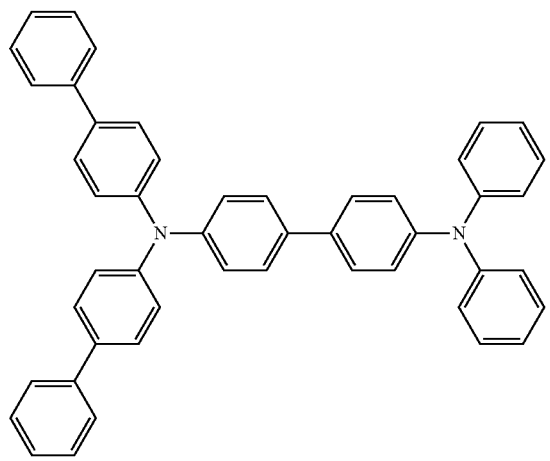
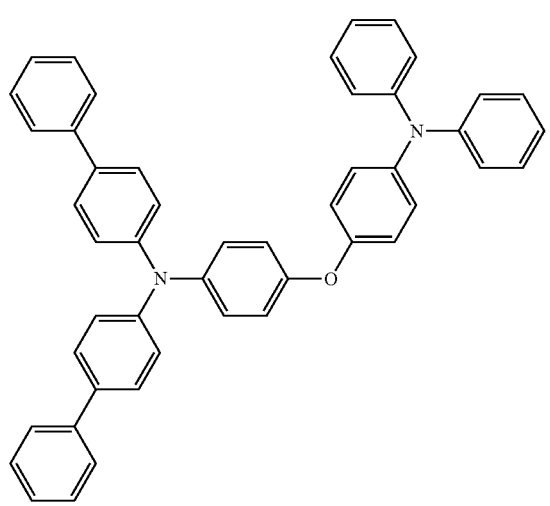
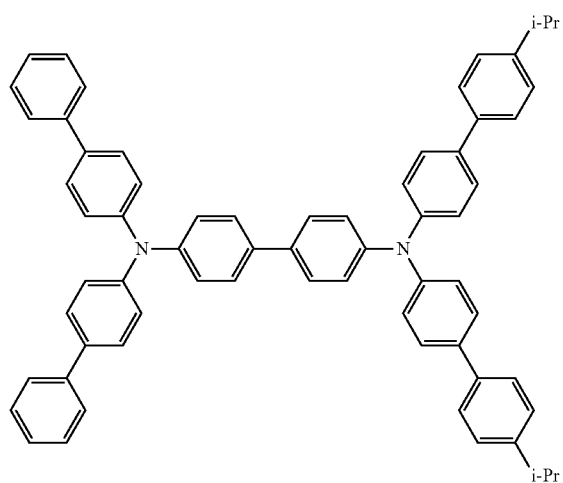
72
-continued
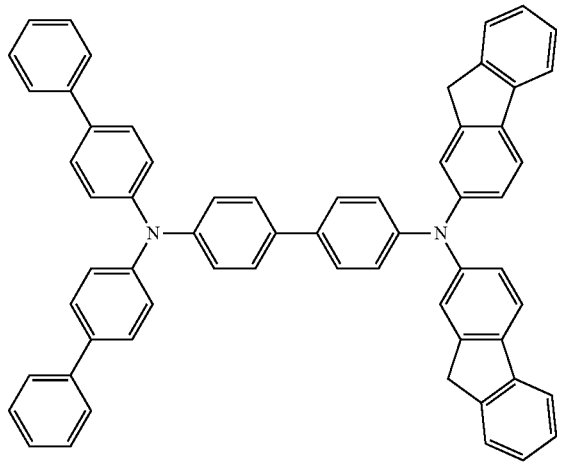
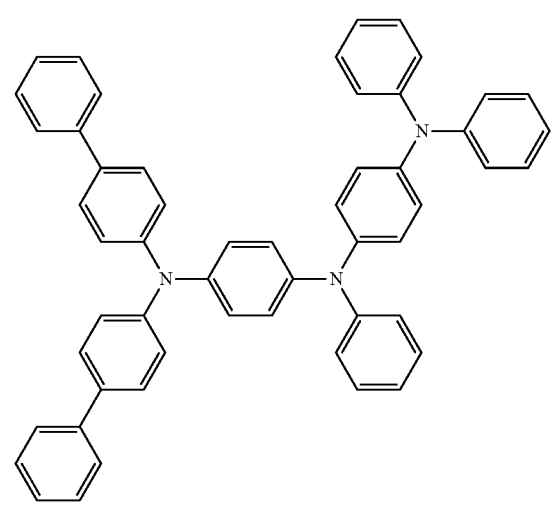
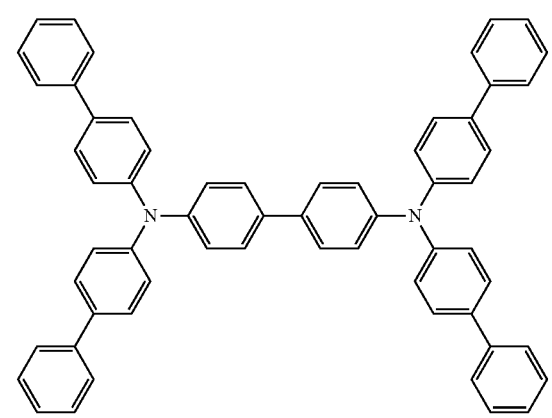

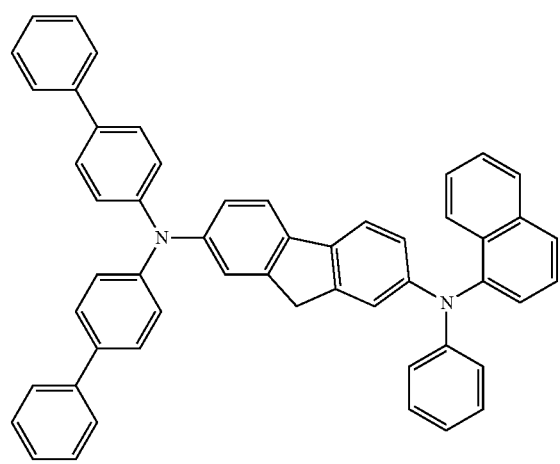
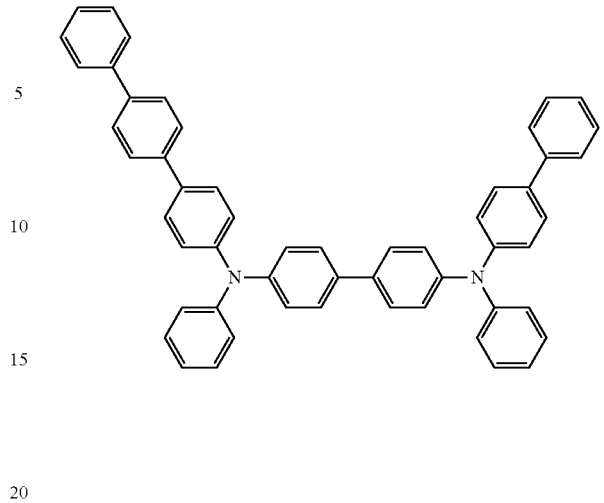
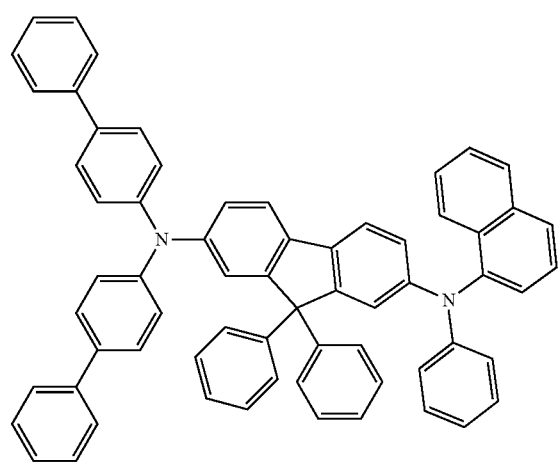
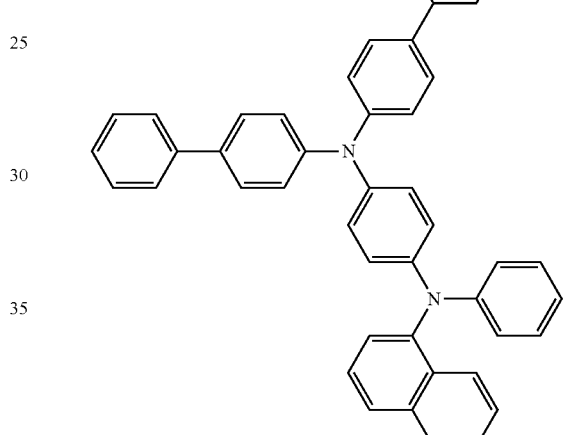
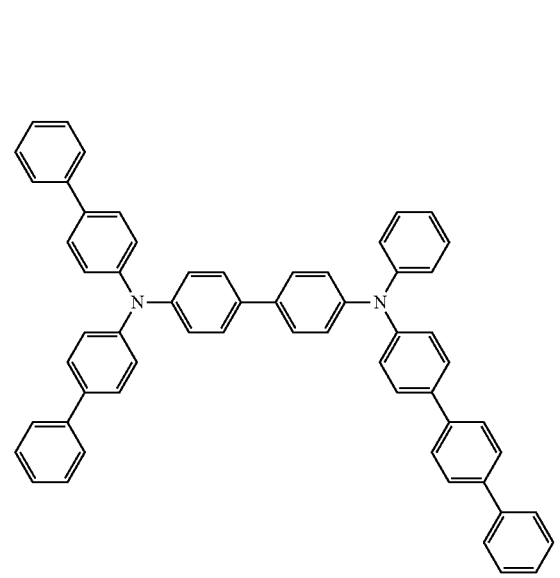
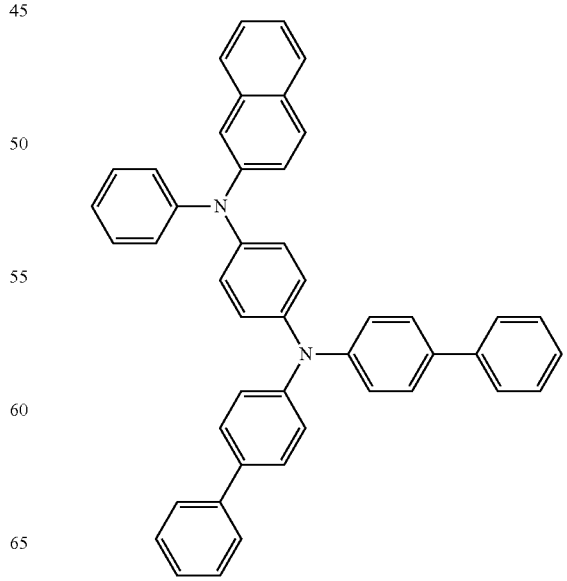

75
-continued
76
-continued
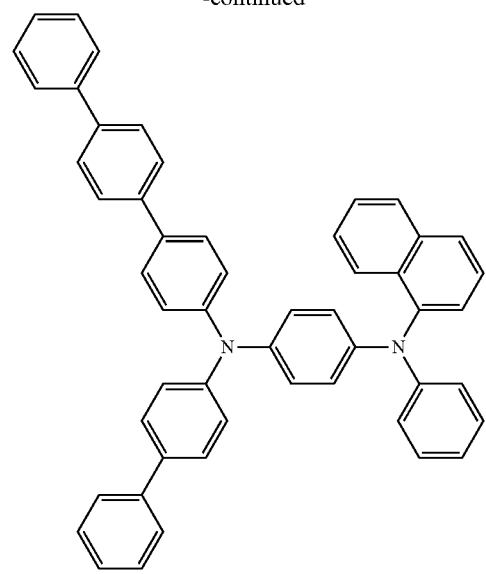
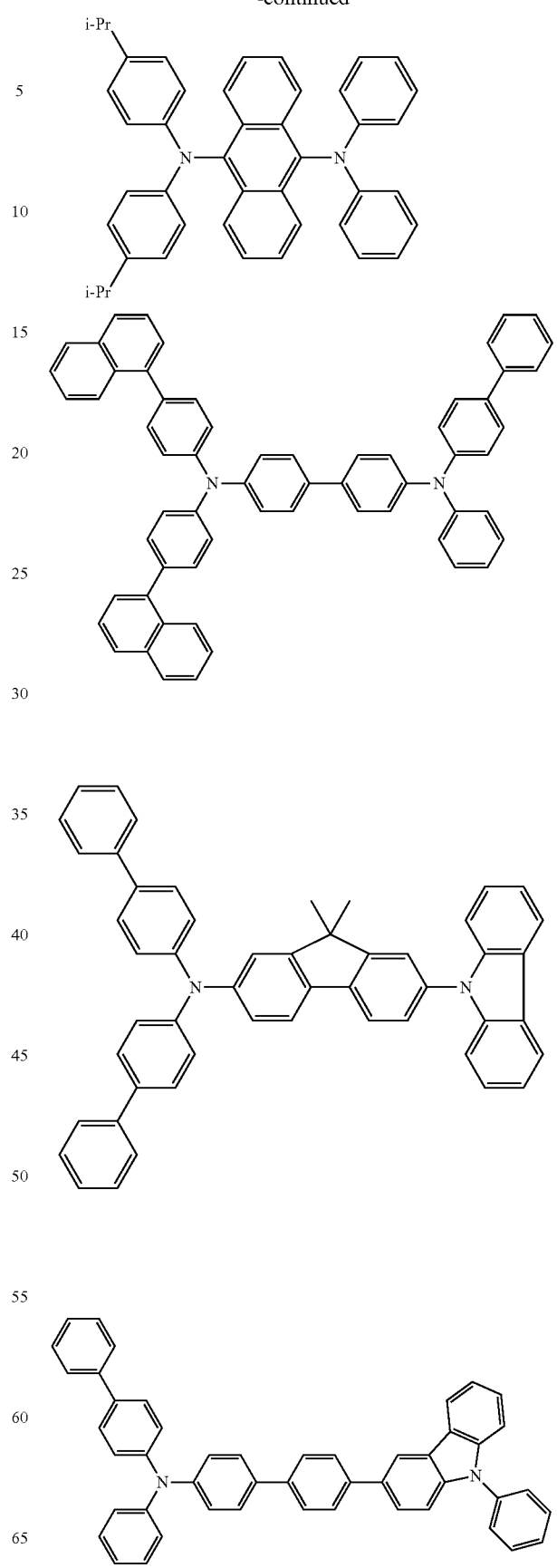

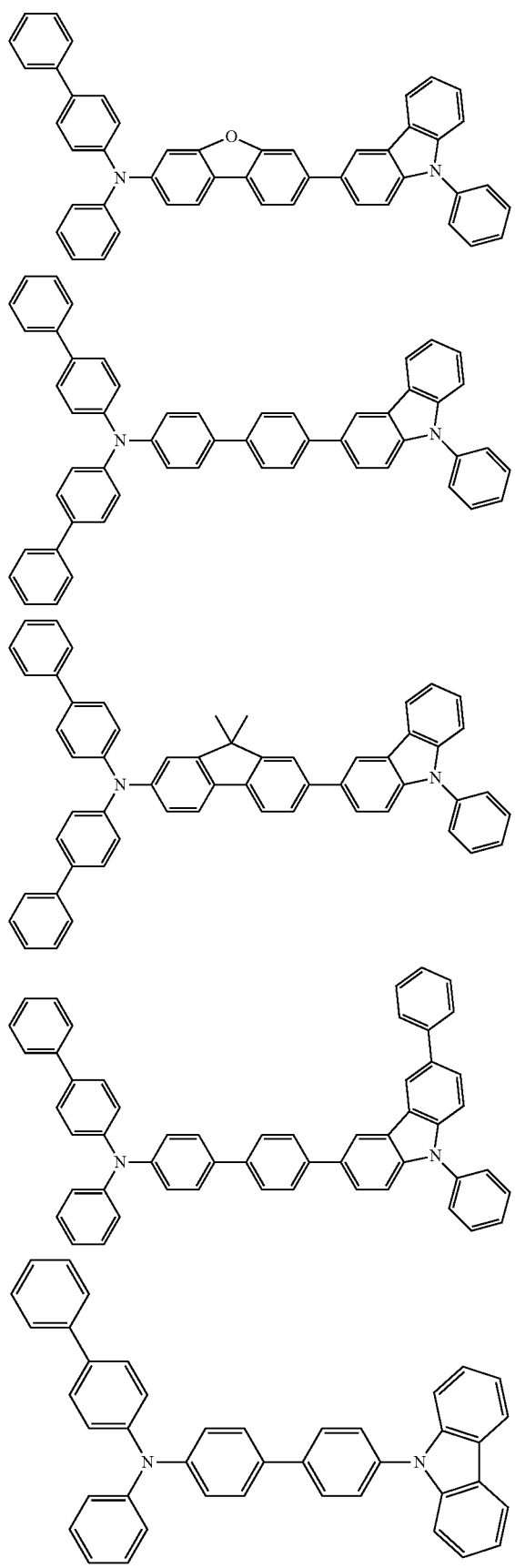
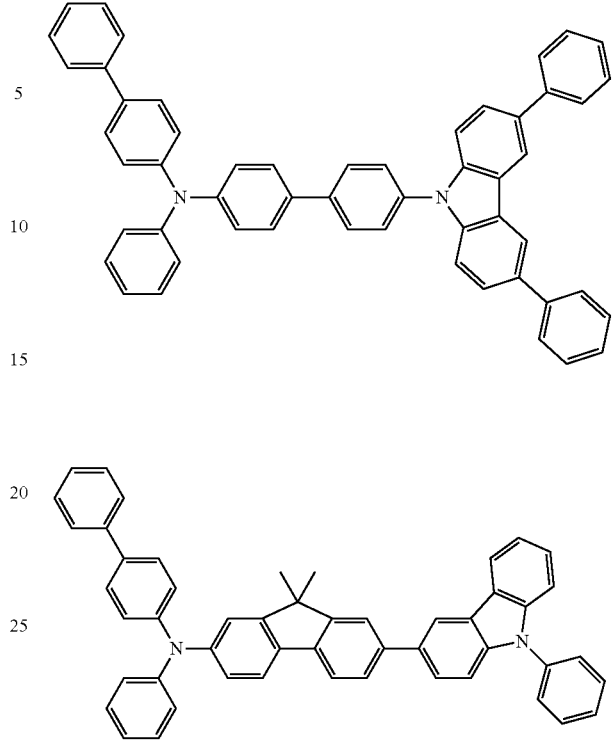
In addition, an aromatic amine represented by formula (J) is preferably used in the hole transporting layer:
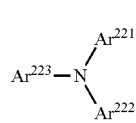
(J)
wherein $Ar^{221}$ to $Ar^{223}$ are the same as defined above with respect to $Ar^{211}$ to $Ar^{214}$ of formula (H). Examples of the compound represented by formula (J) are shown below, although not limited thereto.
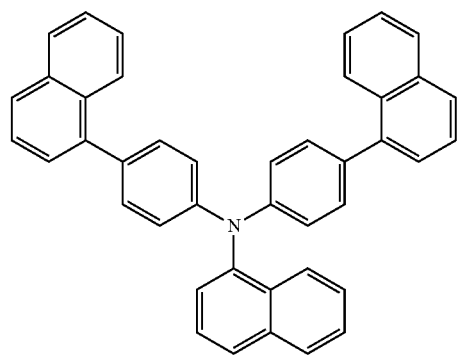

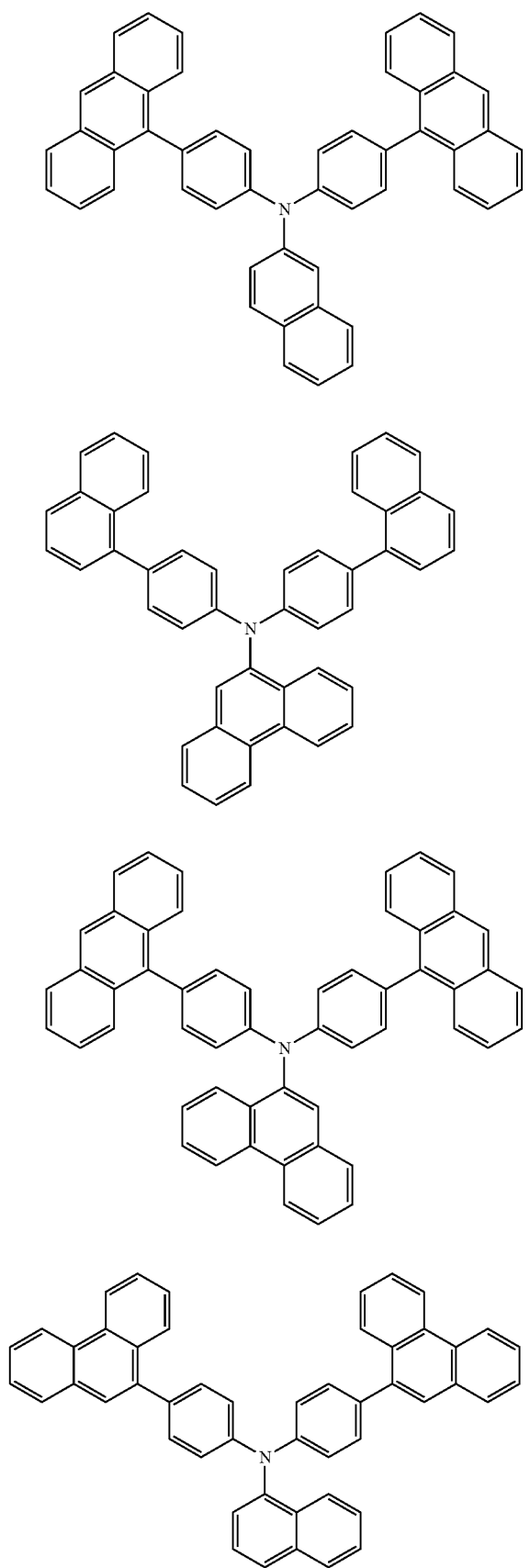
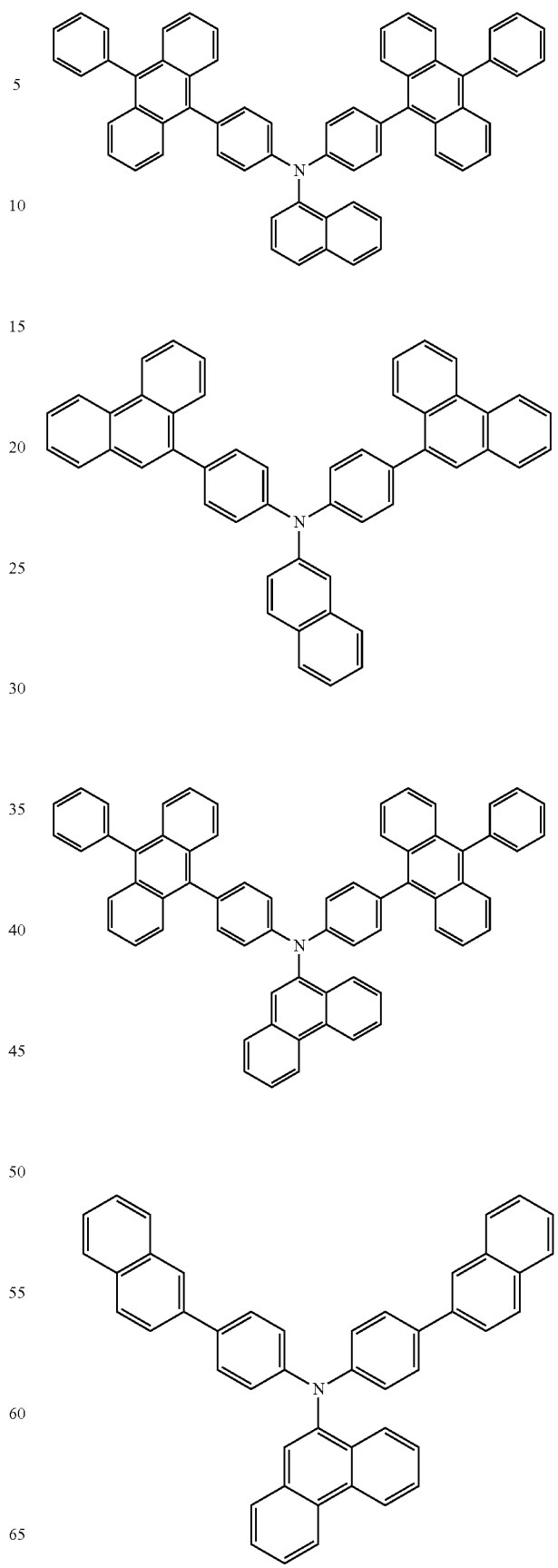

81
-continued
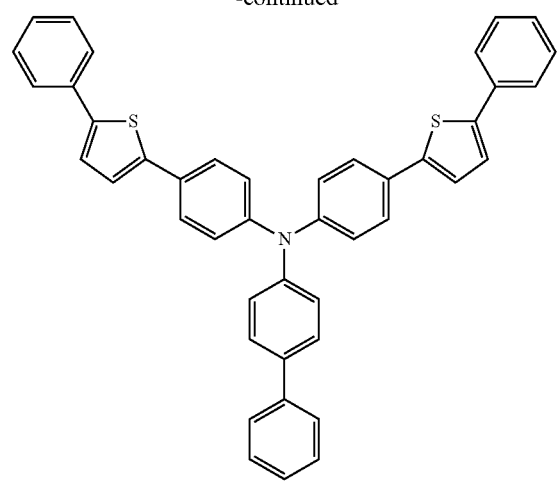
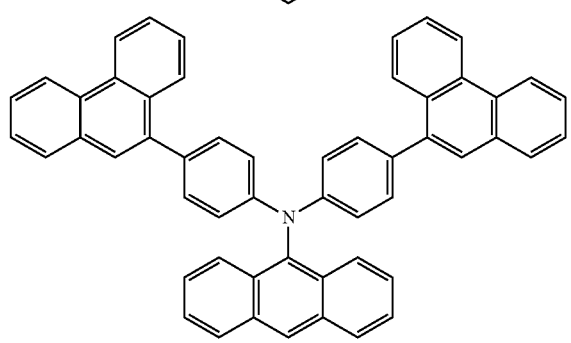
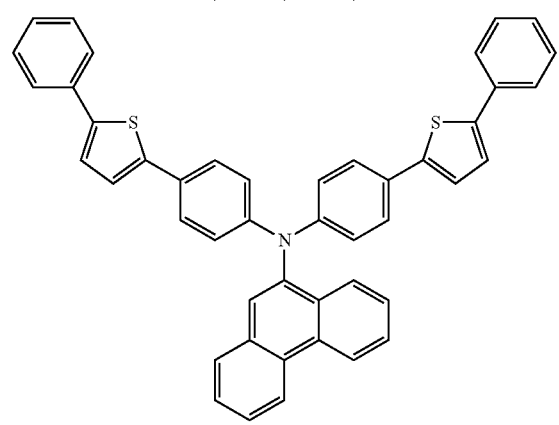
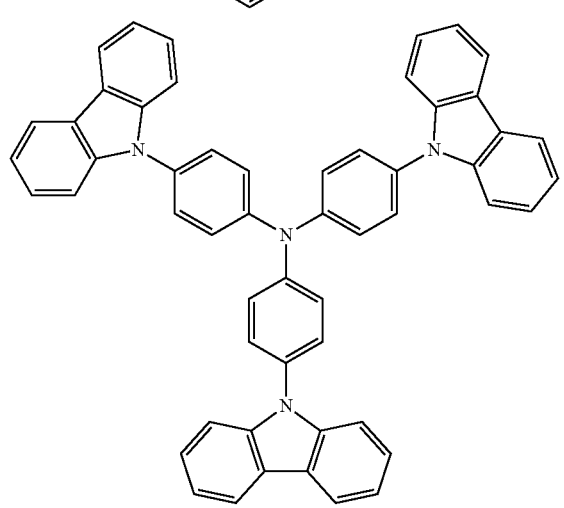
82
-continued
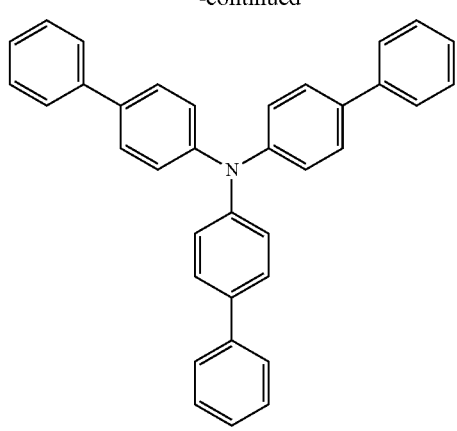
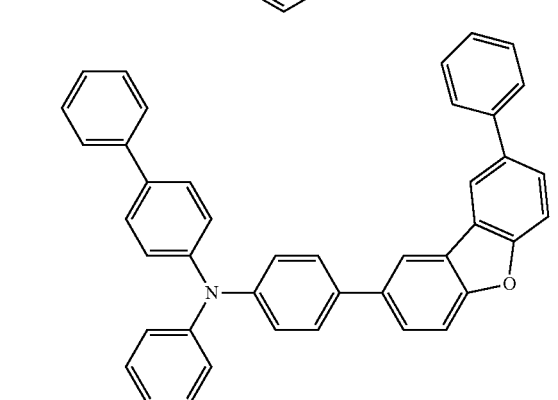
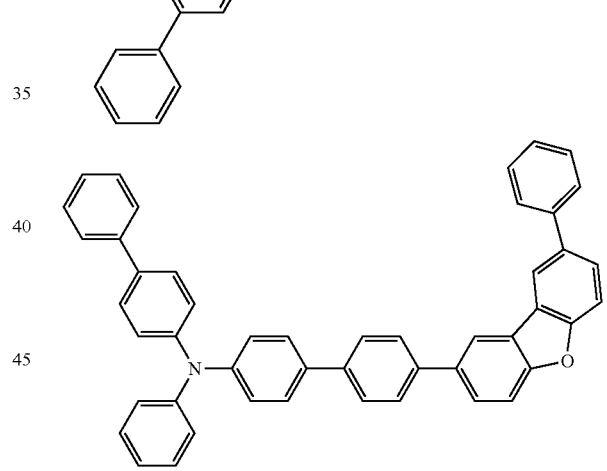
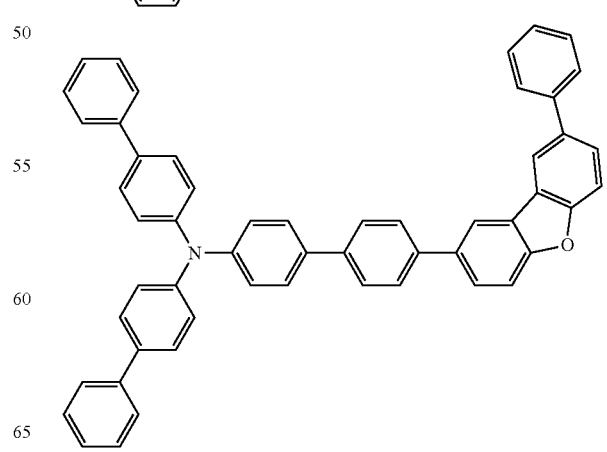

83
-continued
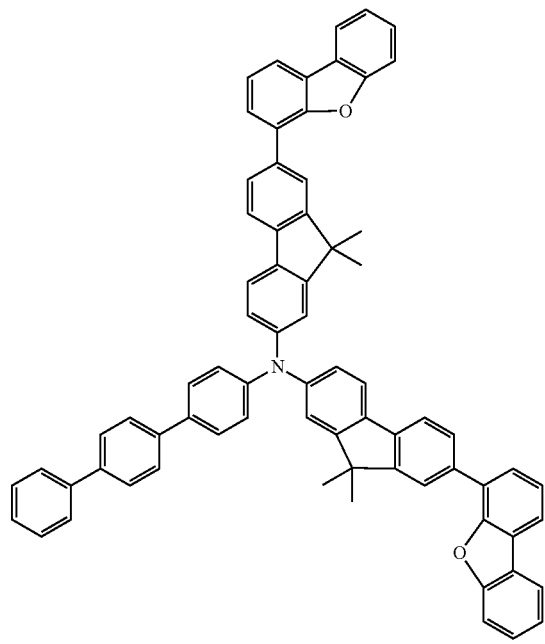
84
-continued
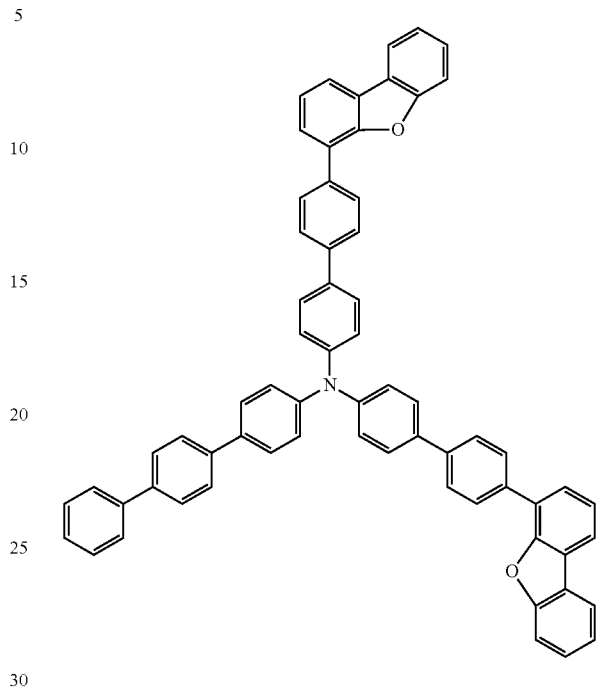
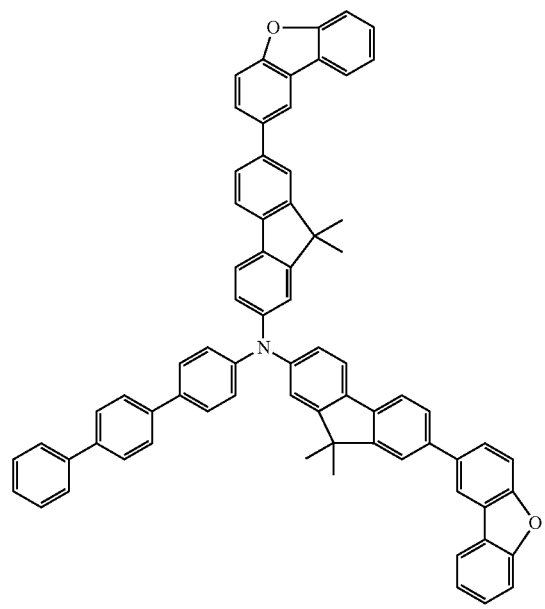
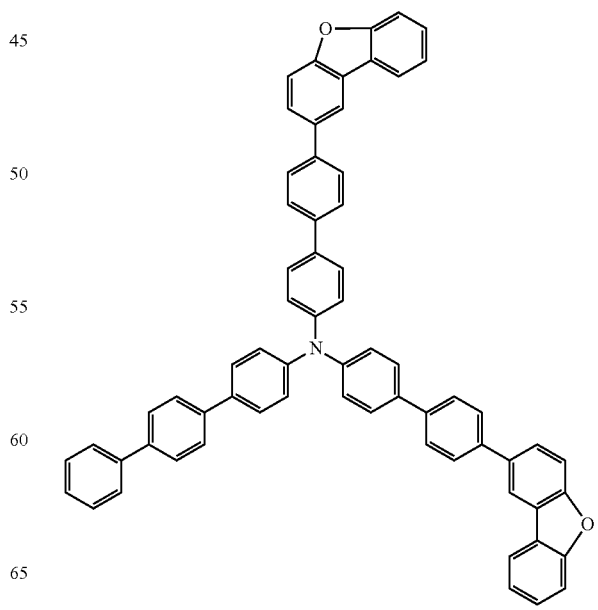

85
-continued
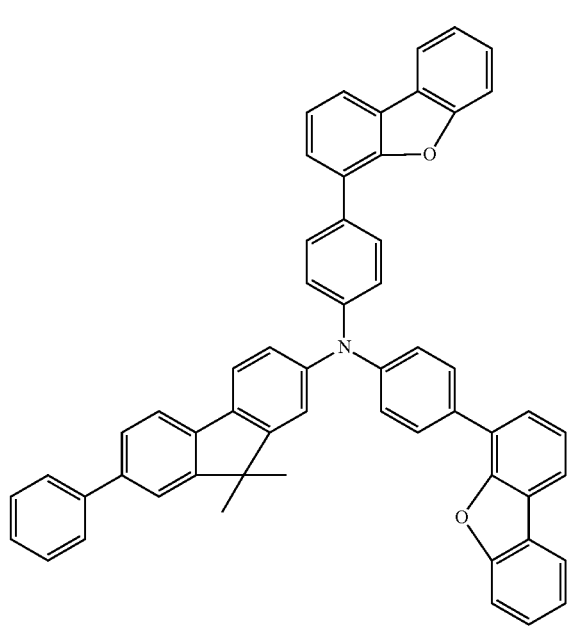
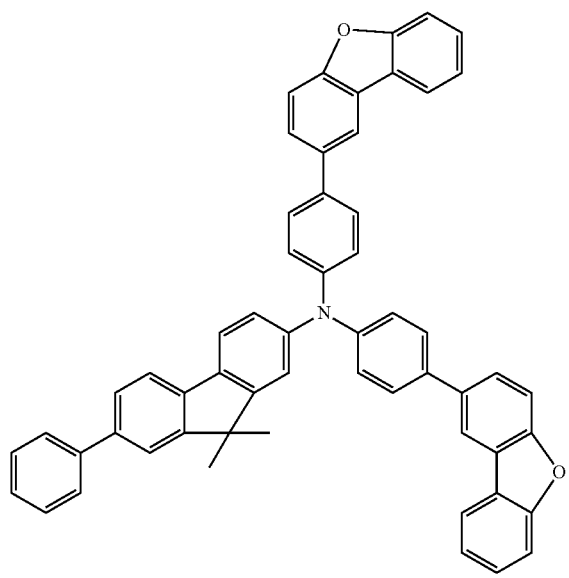
86
-continued
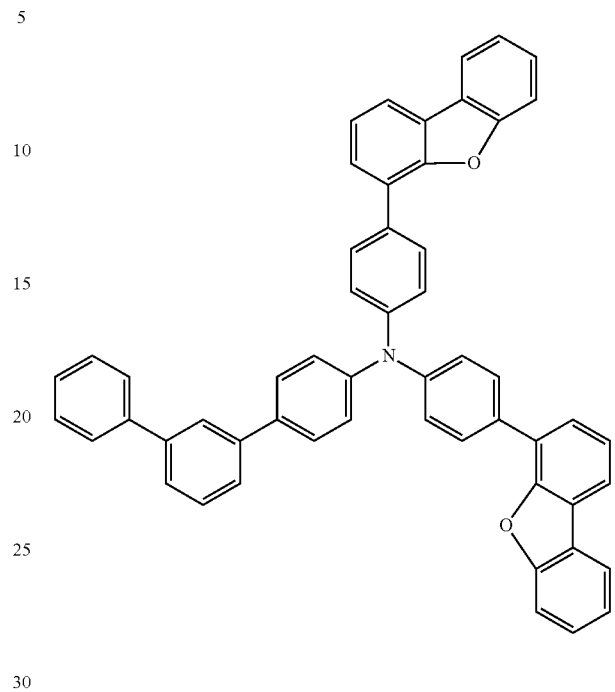
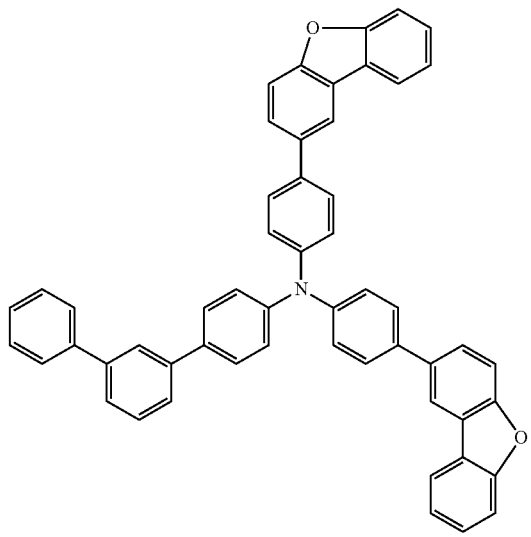

87
88
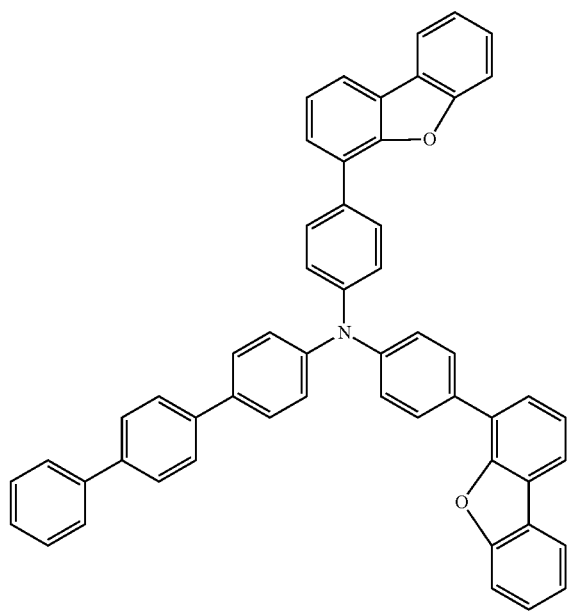
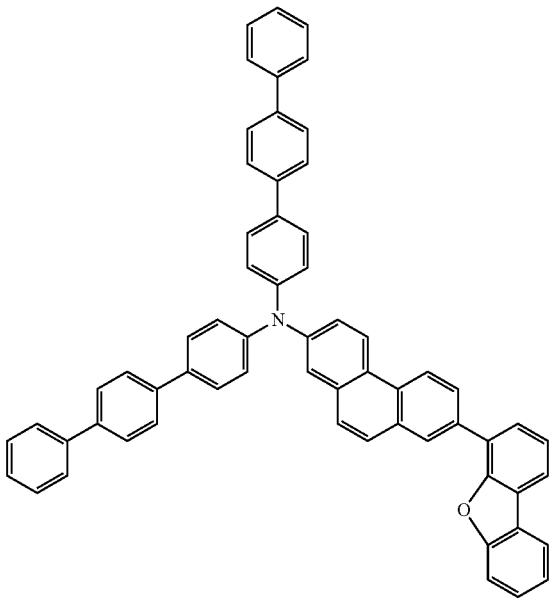
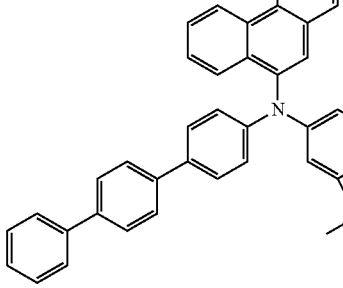
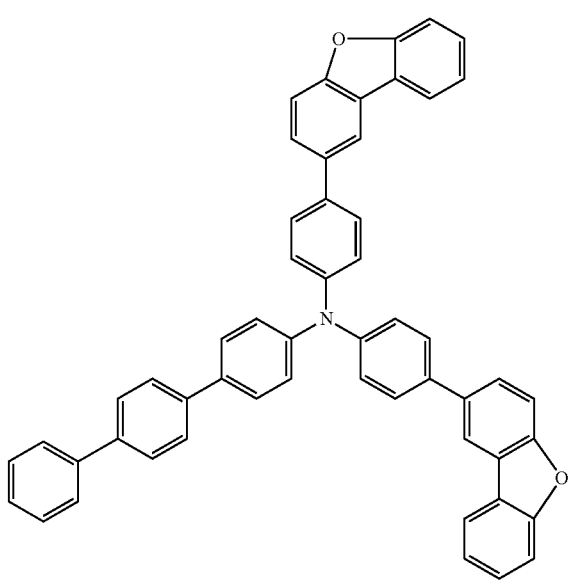

89
-continued
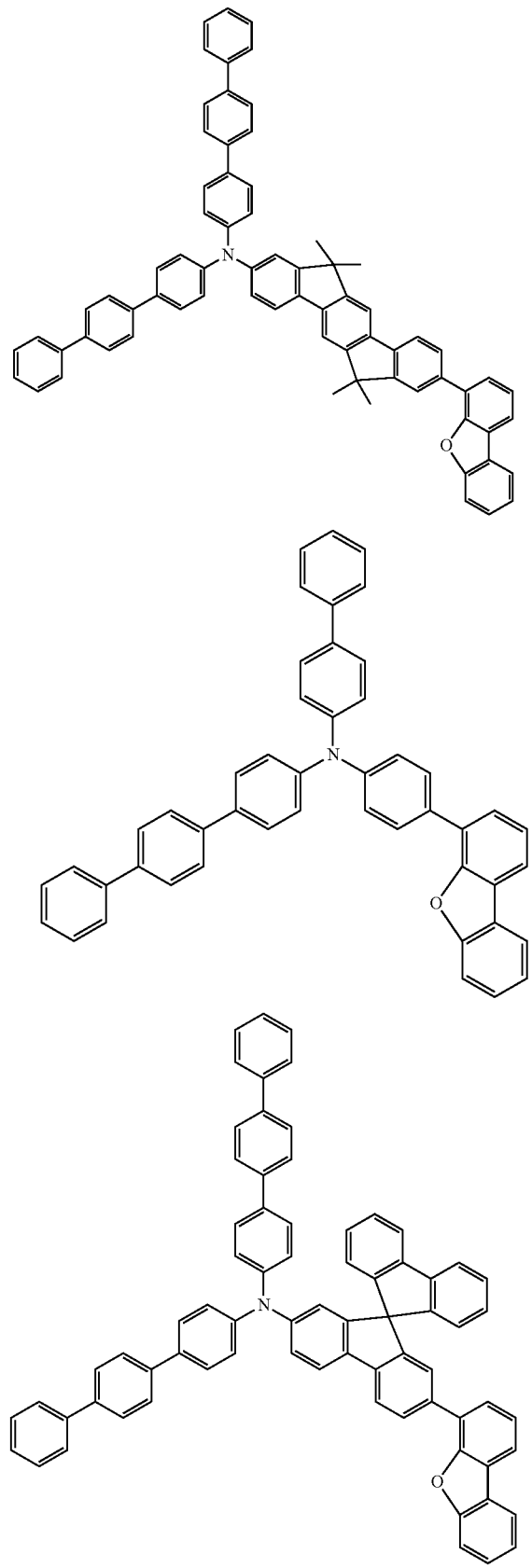
90
-continued
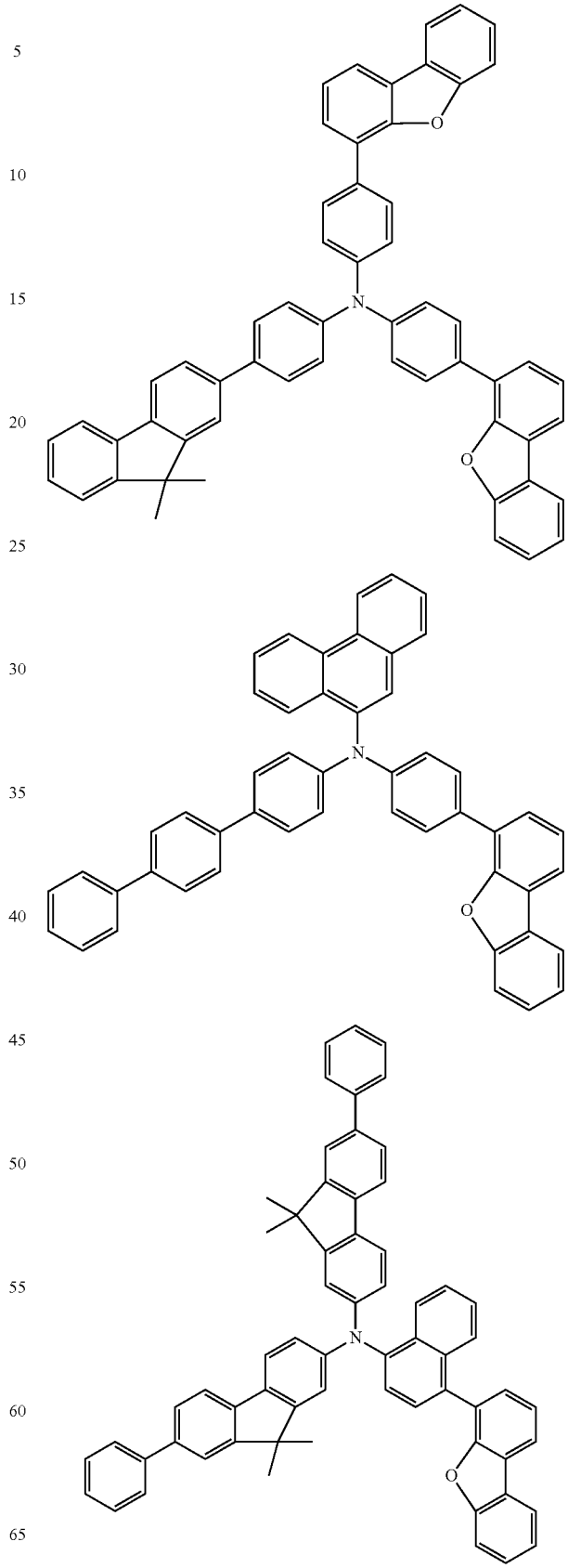

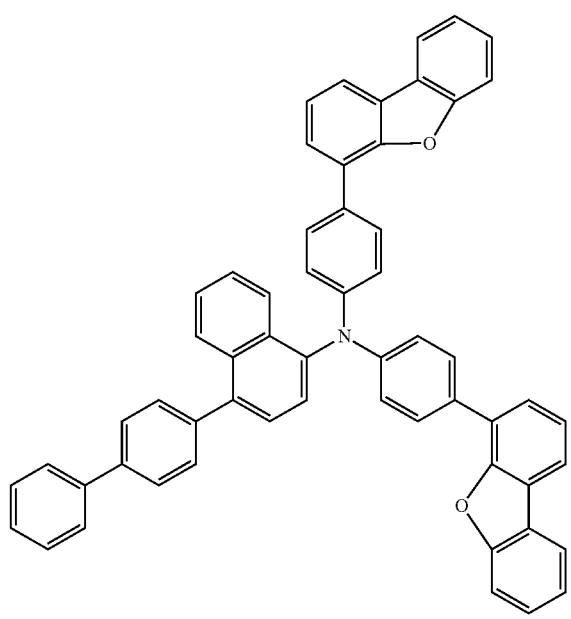

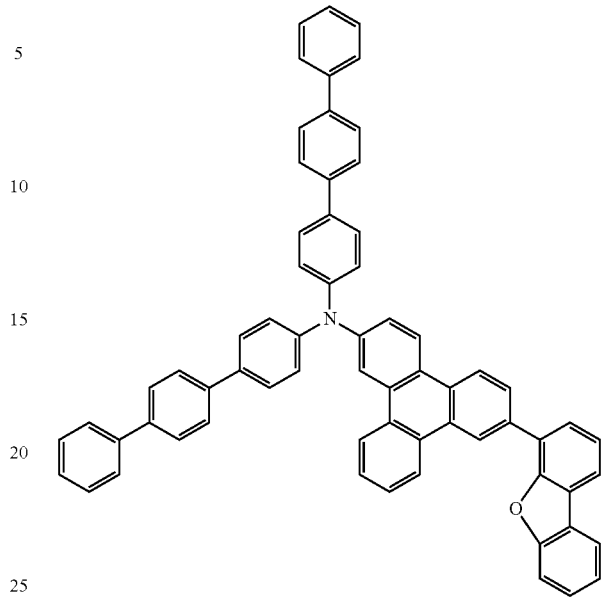

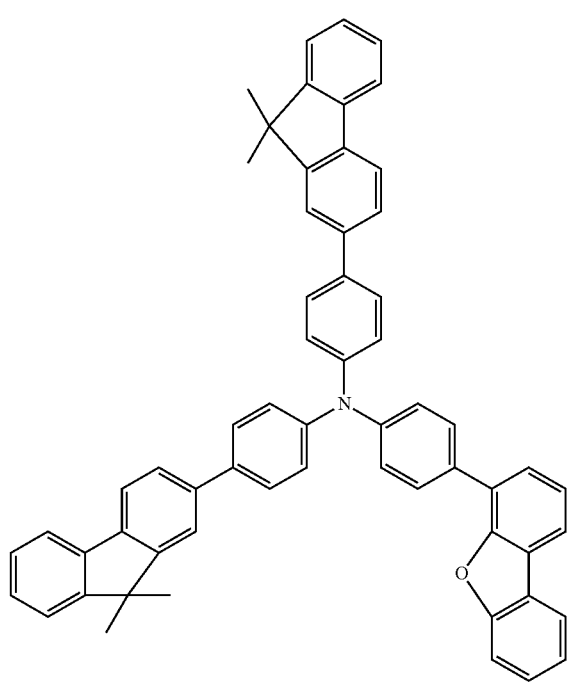

The hole transporting layer of the organic EL device in an aspect of the invention may be made into two-layered structure of a first hole transporting layer (anode side) and a second hole transporting layer (cathode side).

The thickness of the hole transporting layer is preferably 10 to 200 nm, although not particularly limited thereto.

The organic EL device in an aspect of the invention may include a layer comprising an acceptor material which is disposed in contact with the anode side of the hole transporting layer or the first hole transporting layer. With such a layer, it is expected that the driving voltage is lowered and the production cost is reduced.

The acceptor material is preferably a compound represented by formula (K):

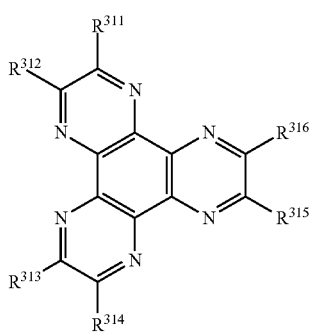

(K)

wherein R³¹¹ to R³¹⁶ may be the same or different and each independently represent a cyano group, —CONH$_2$, a carboxyl group, or —COOR³¹⁷ wherein R³¹⁷ represents an alkyl group having 1 to 20 carbon atoms or a cycloalkyl group having 3 to 20 carbon atoms; and one or more pairs selected from R³¹¹ and R³¹², R³¹³ and R³¹⁴, and R³¹⁵ and R³¹⁶ may bond to each other to form a group represented by —CO—O—CO—.

Examples of R³¹⁷ include a methyl group, an ethyl group, a n-propyl group, an isopropyl group, a n-butyl group, an isobutyl group, a t-butyl group, a cyclopentyl group, and a cyclohexyl group.

The thickness of the layer comprising the acceptor material is preferably 5 to 20 nm, although not particularly limited thereto.

The following compounds may be used as the acceptor material.

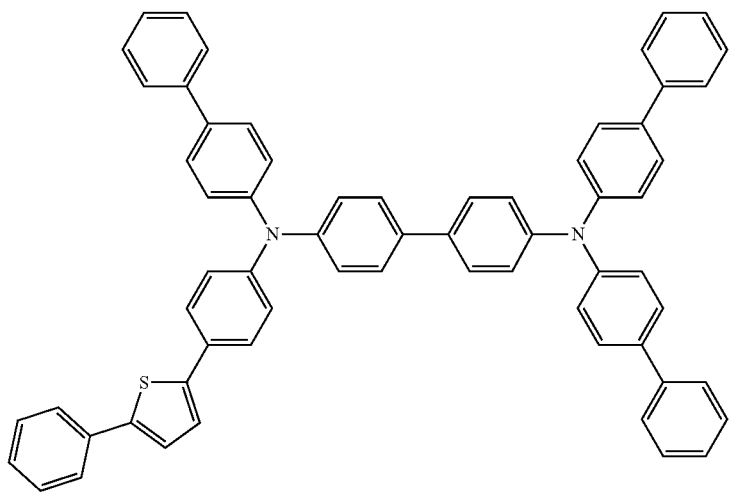

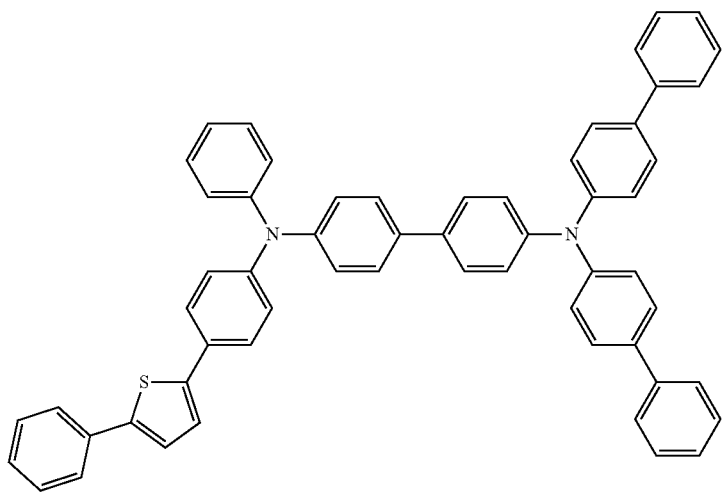

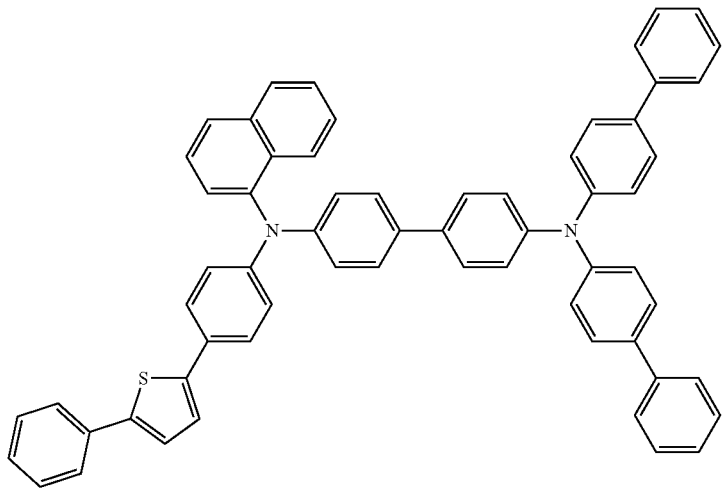
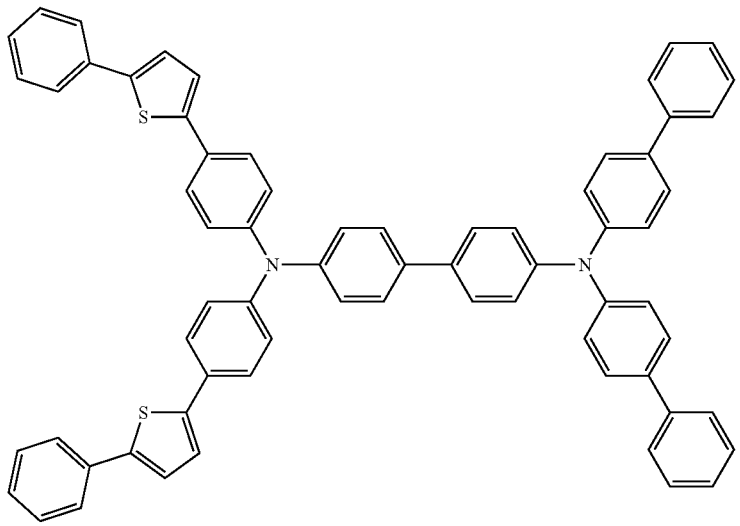
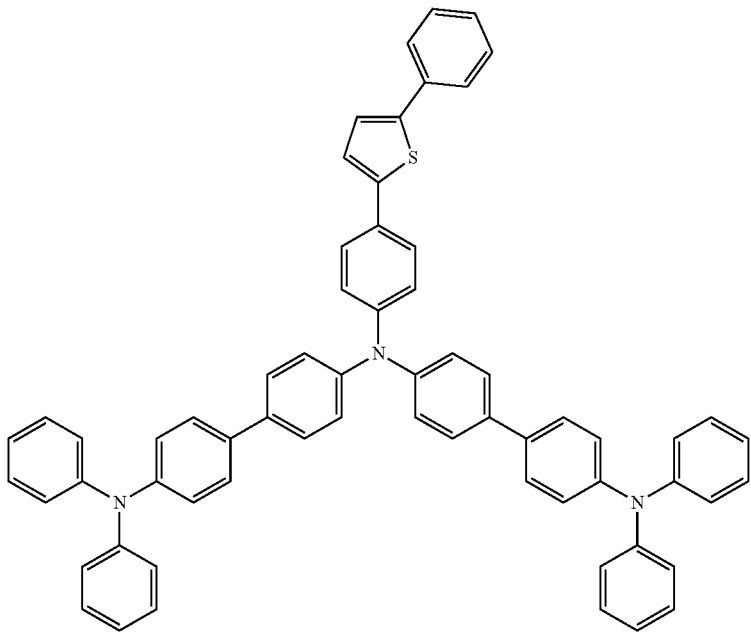

-continued
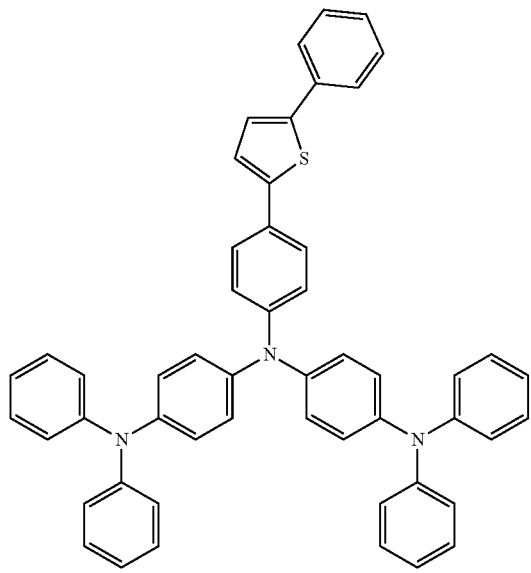
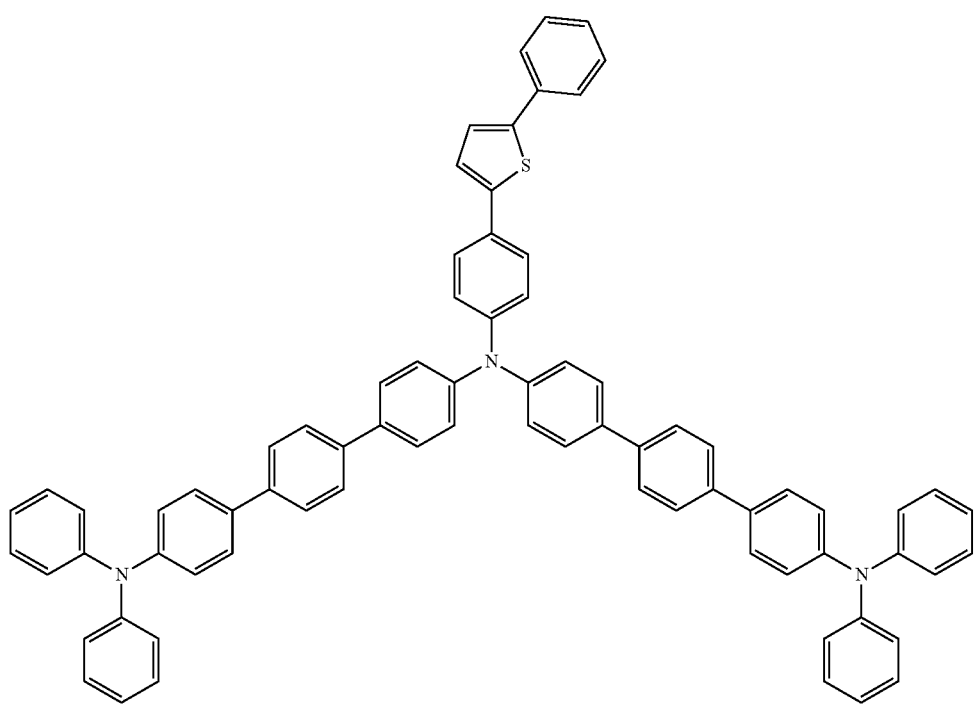

-continued
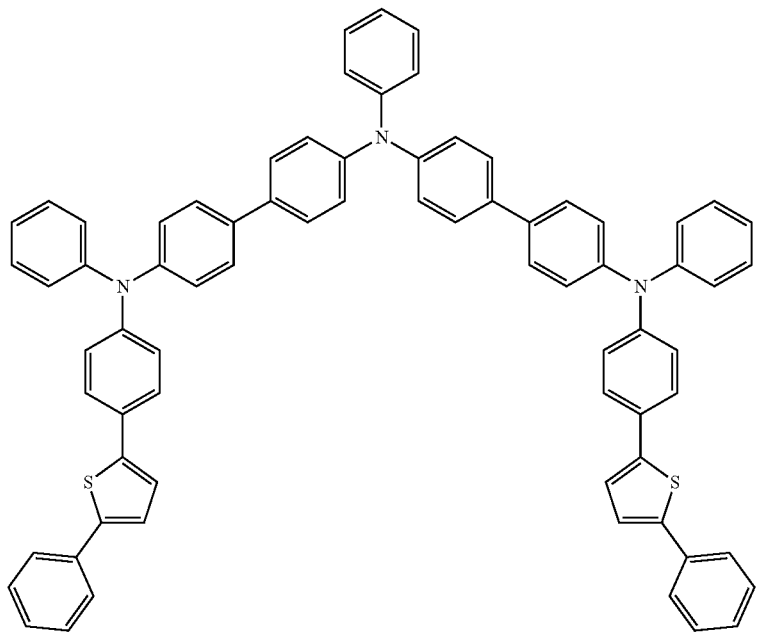
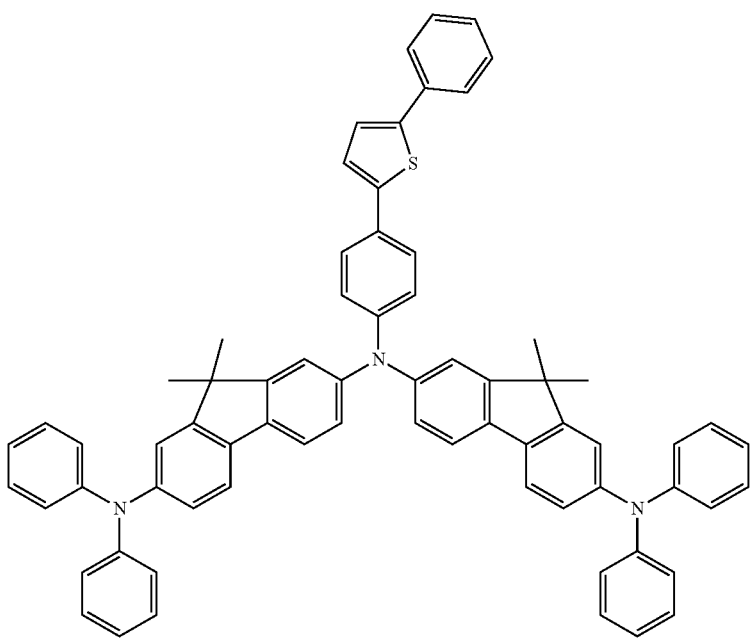

-continued
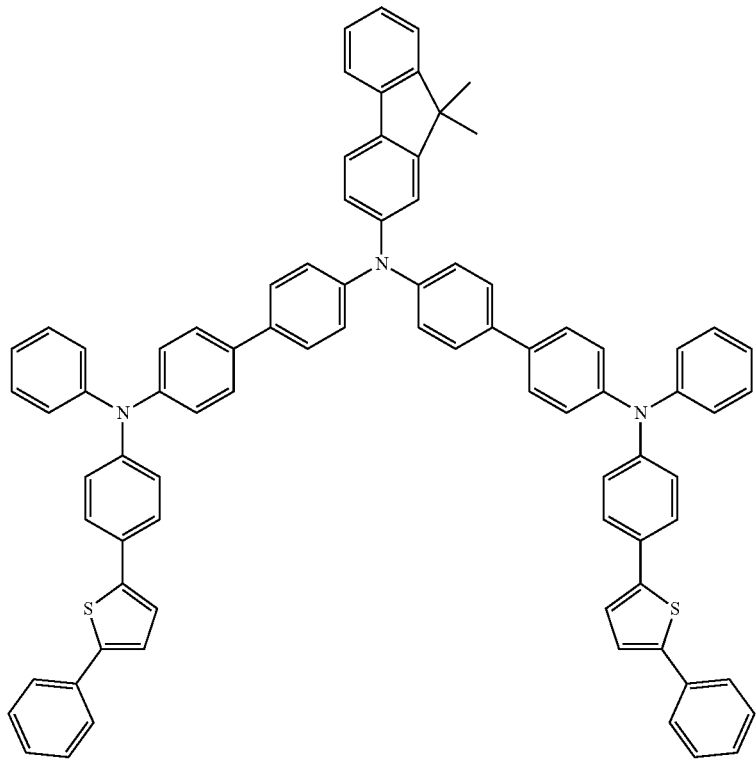
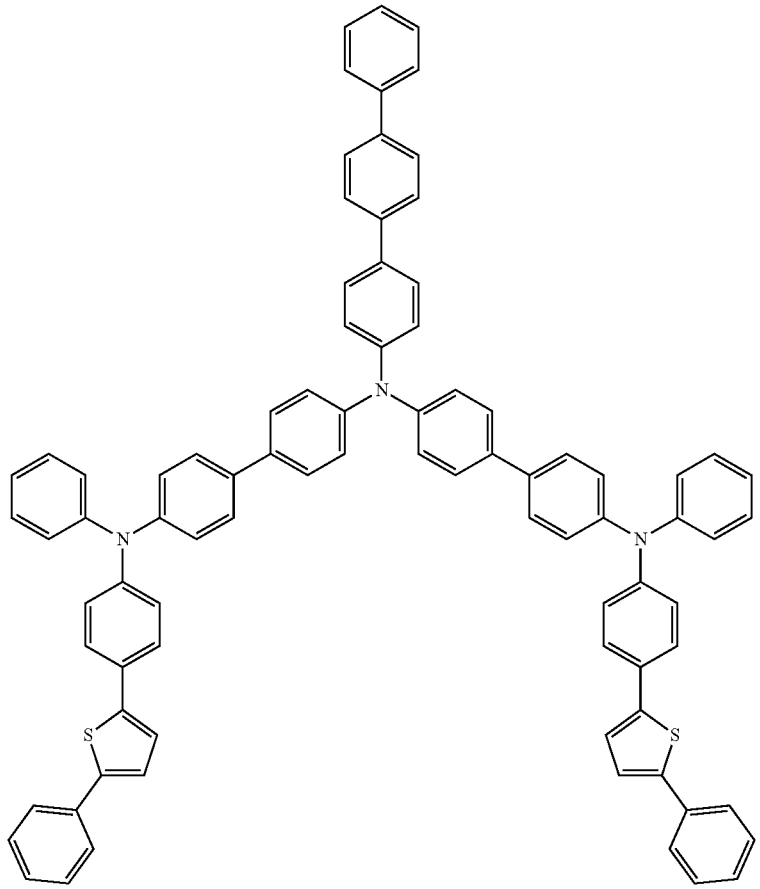

-continued
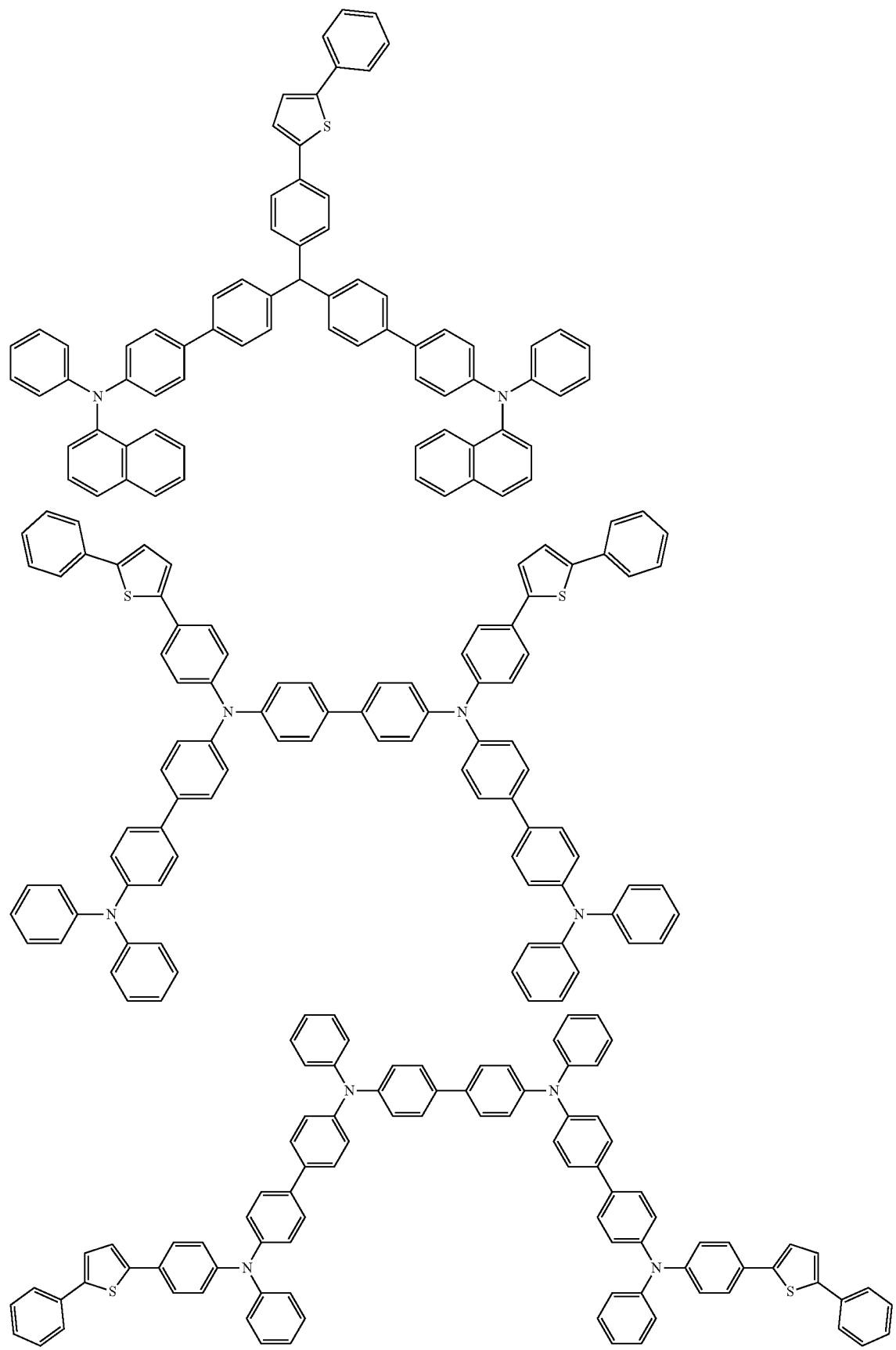

-continued
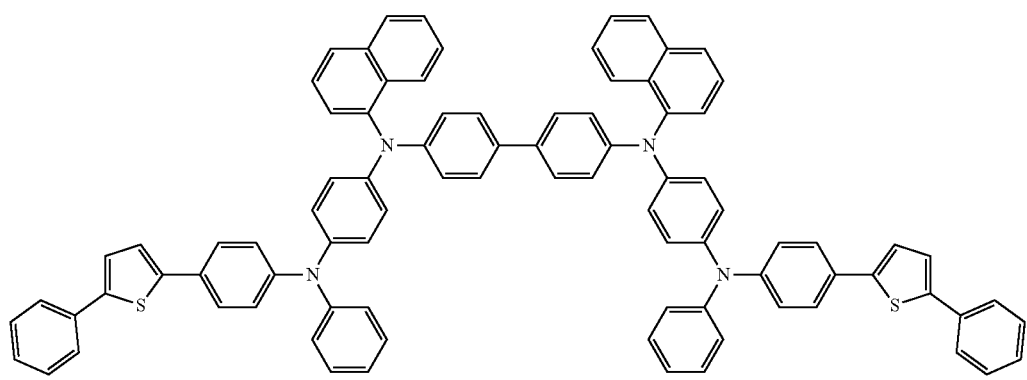
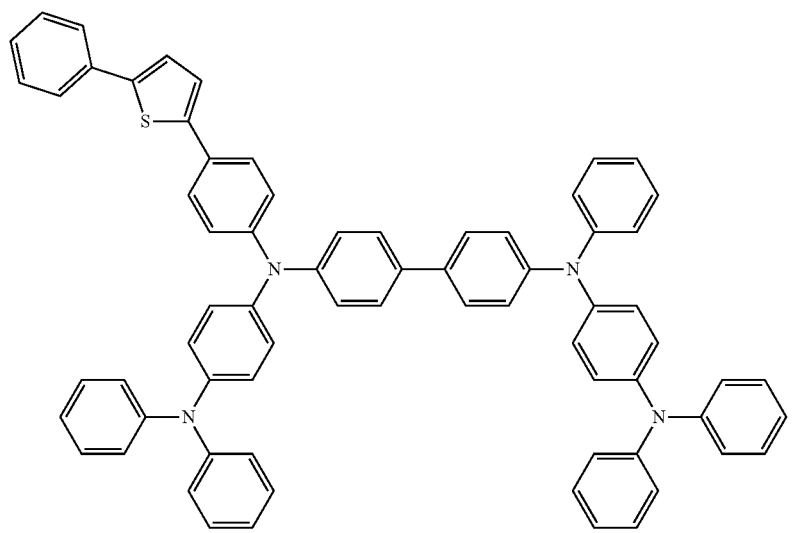
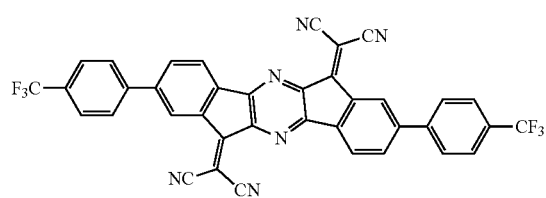
(A-1)
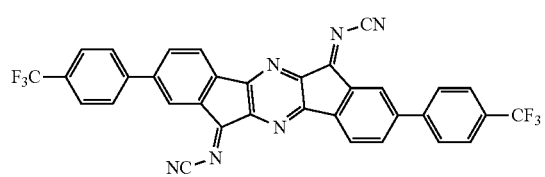
(A-2)
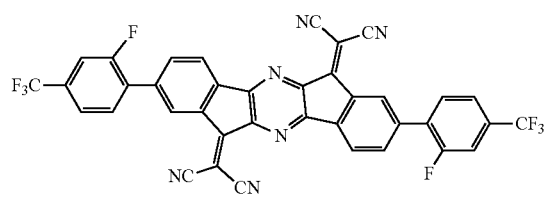
(A-3)
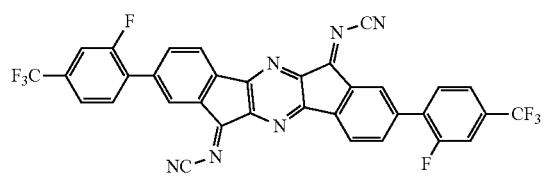
(A-4)
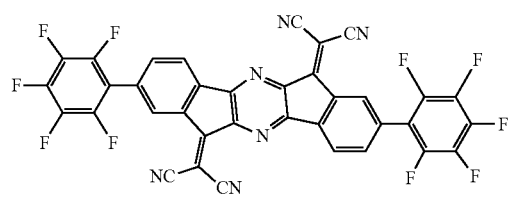
(A-5)
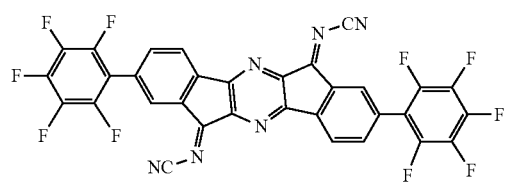
(A-6)

-continued
(A-7)
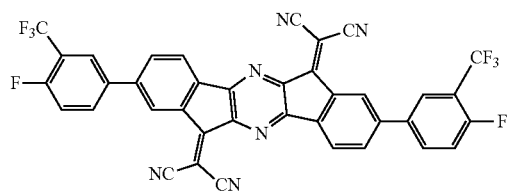
(A-8)
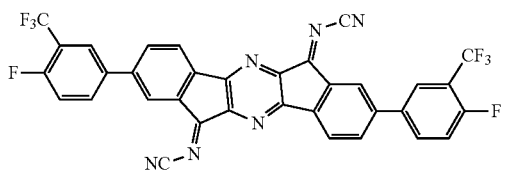
(A-9)
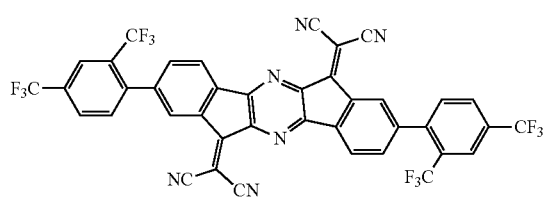
(A-10)
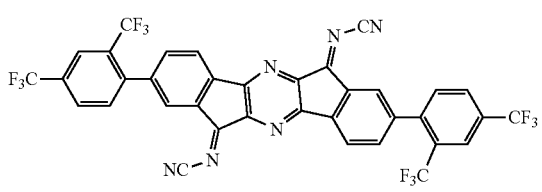
(A-11)
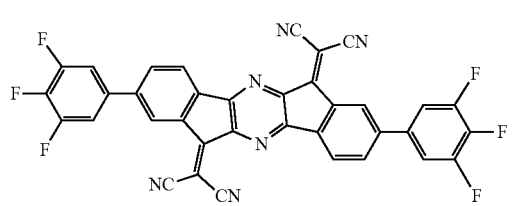
(A-12)
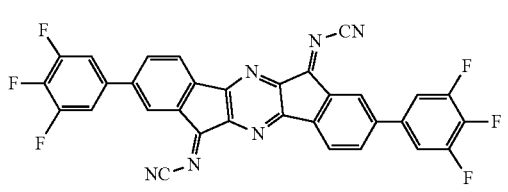
(A-13)
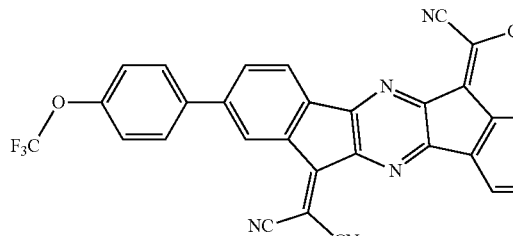
(A-14)
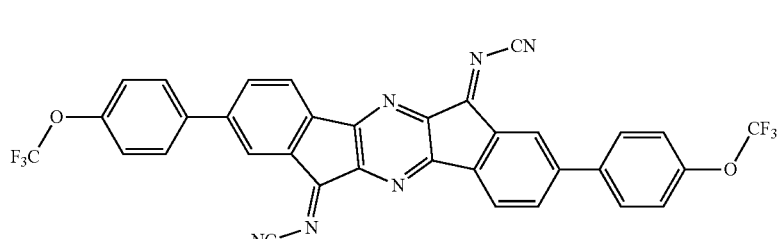
(A-15)
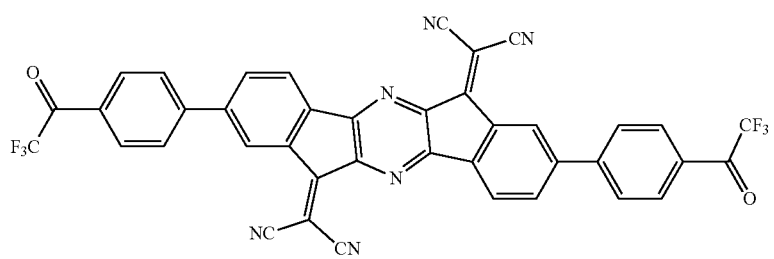
(A-16)
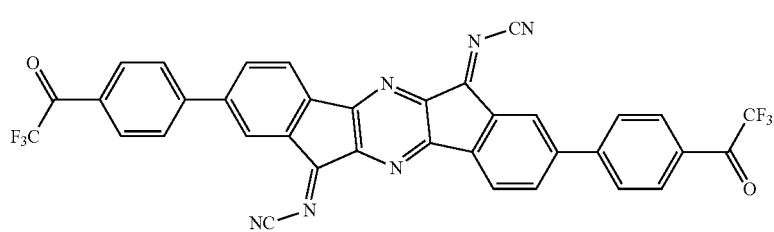

-continued
(A-17) 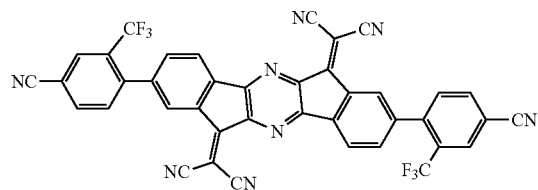
(A-18) 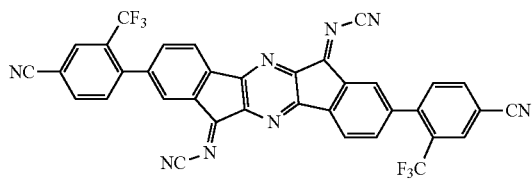
(A-19) 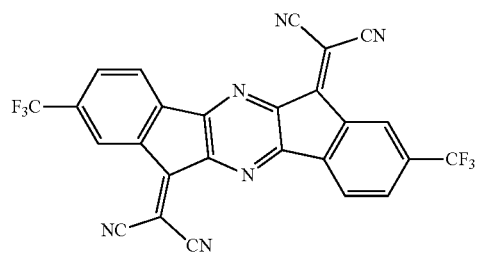
(A-20) 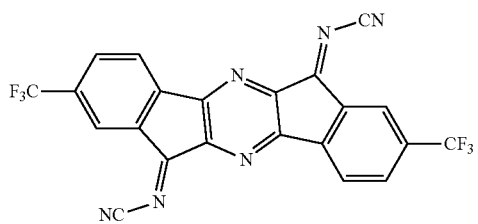
(A-21) 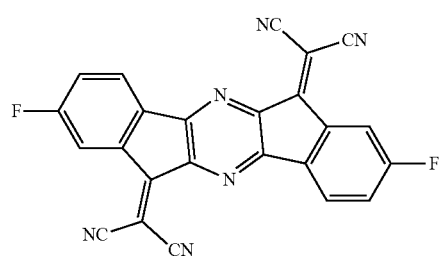
(A-22) 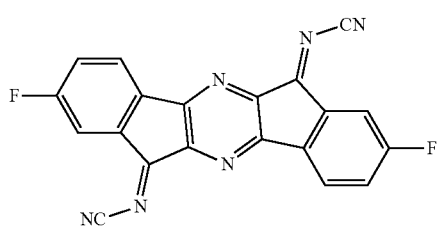
(A-23) 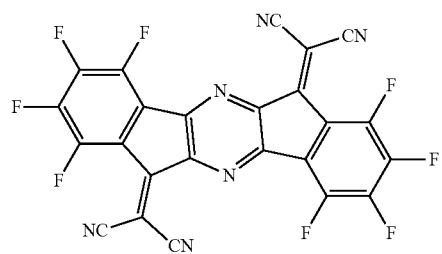
(A-24) 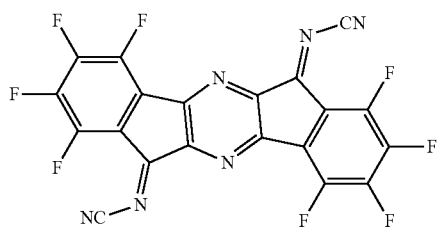
(A-25) 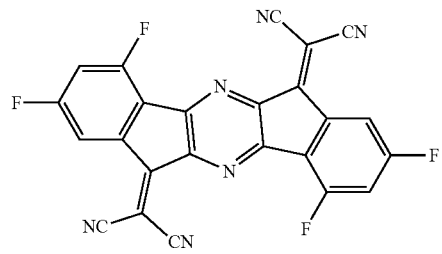
(A-26) 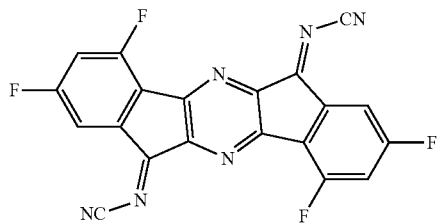
(A-27) 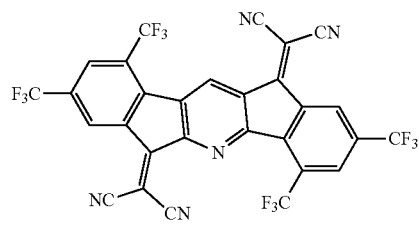
(A-28) 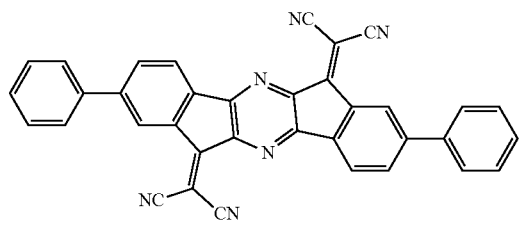

-continued
(A-29)
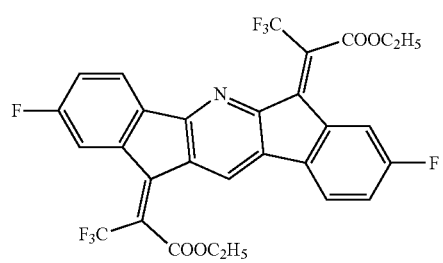
(A-30)
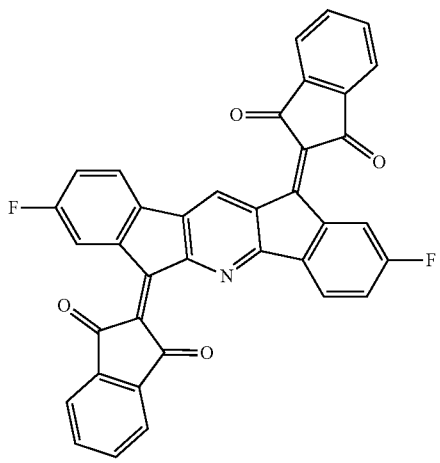
(A-31)
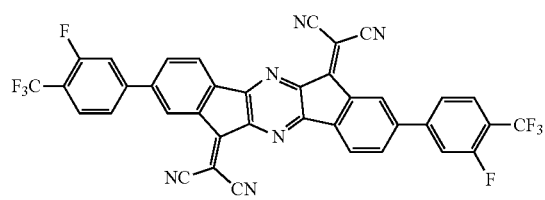
(A-32)
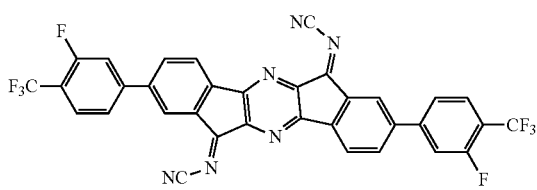
(A-33)
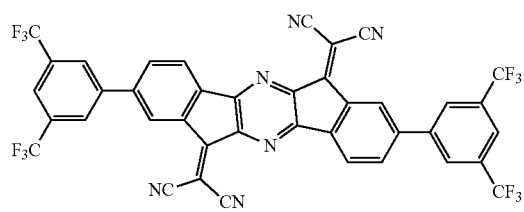
(A-34)
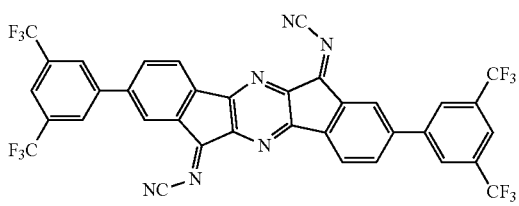
(A-35)
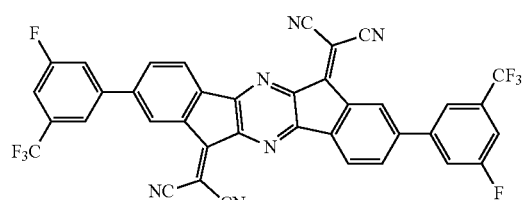
(A-36)
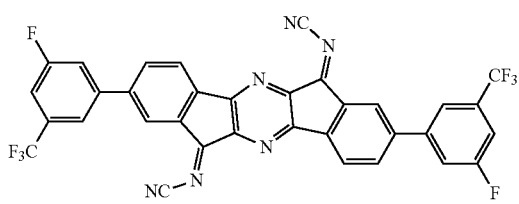
(A-37)
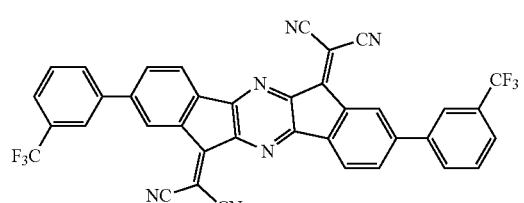
(A-38)
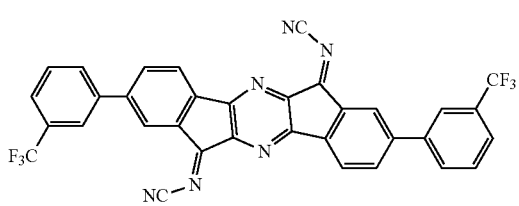
(A-39)
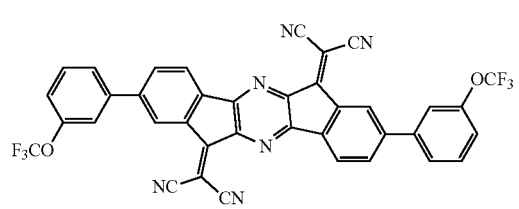
(A-40)
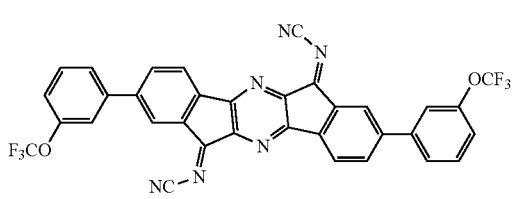

-continued
(A-41)
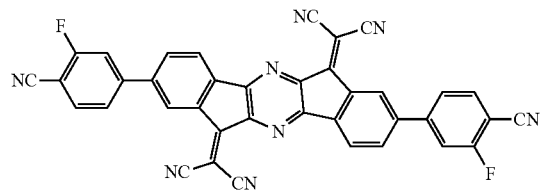
(A-42)
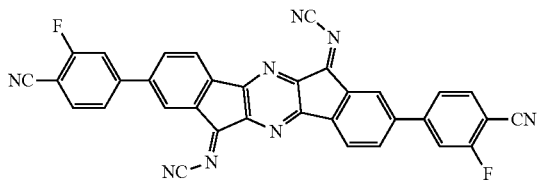
(A-43)
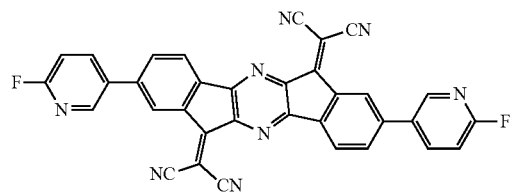
(A-44)
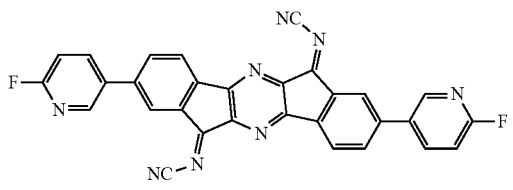
(A-45)
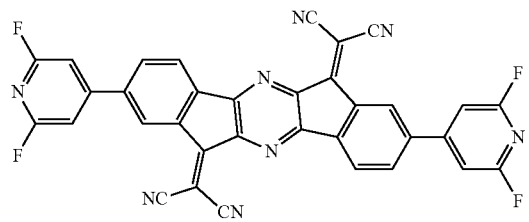
(A-46)
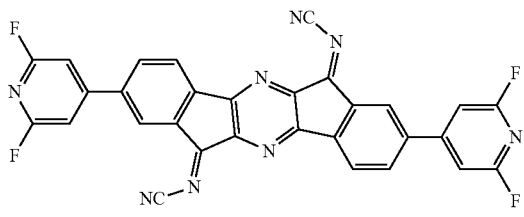
(A-47)
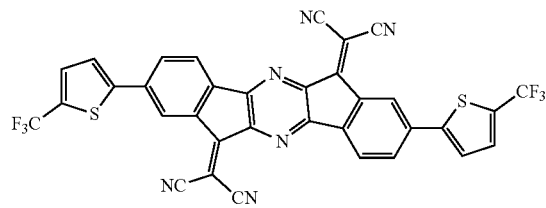
(A-48)
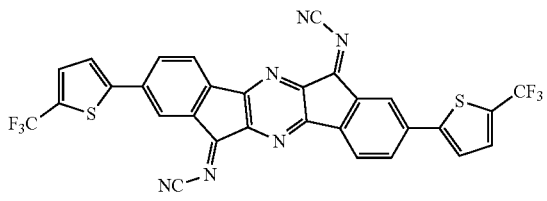
(A-49)
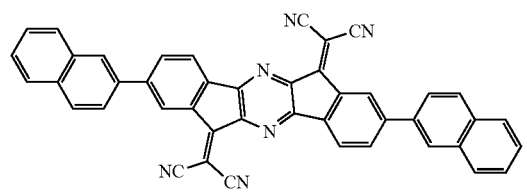
(A-50)
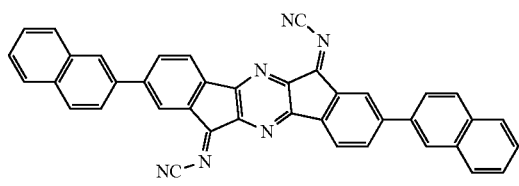
(A-51)
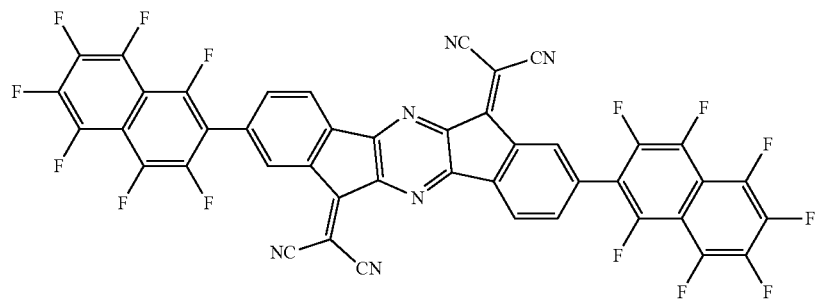

(A-52)
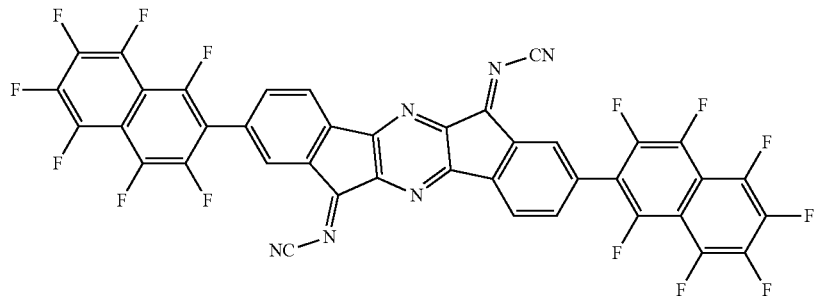
(A-53)
(A-54)
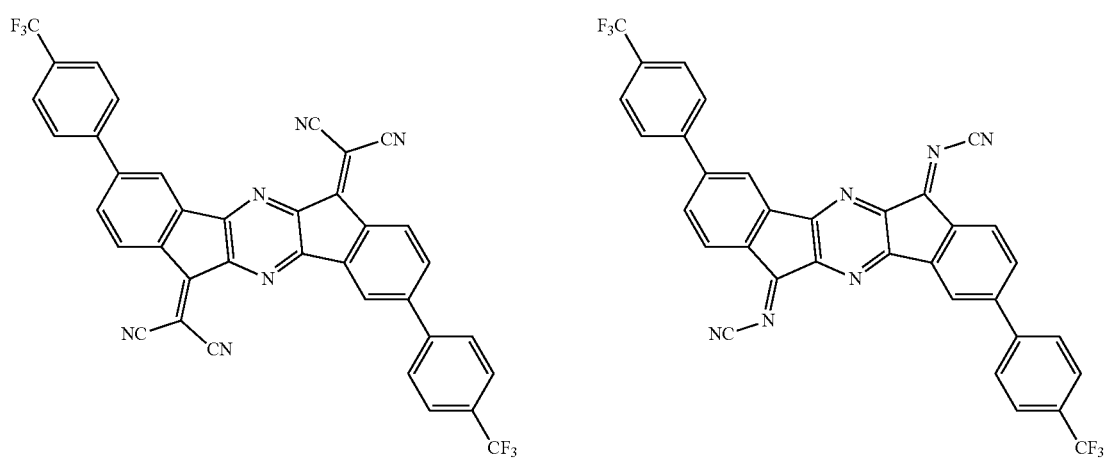
(A-55)
(A-56)
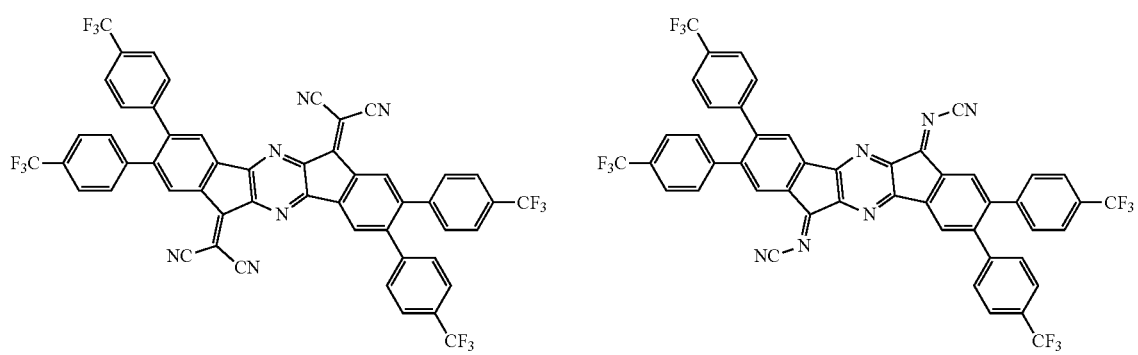
(A-57)
(A-58)
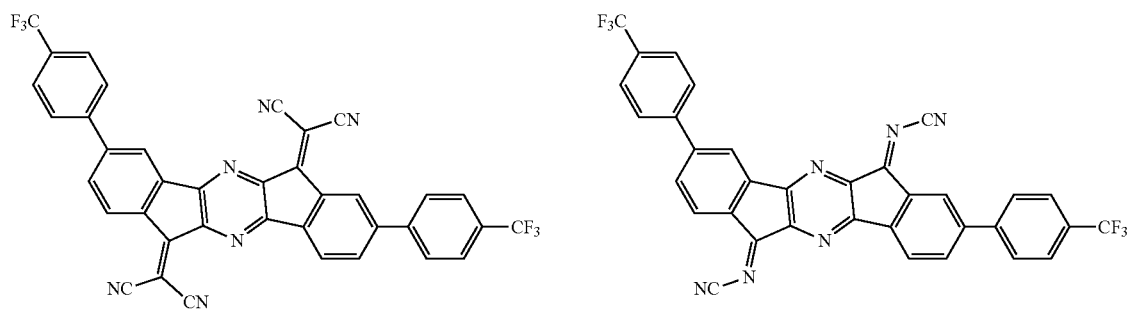

-continued
(A-59) 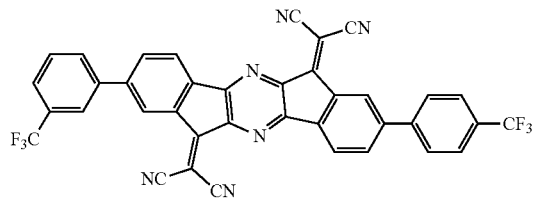
(A-60) 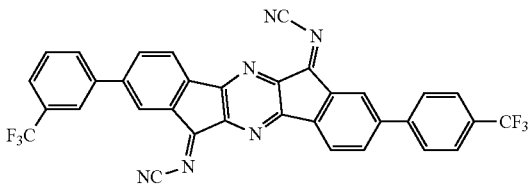
(A-61) 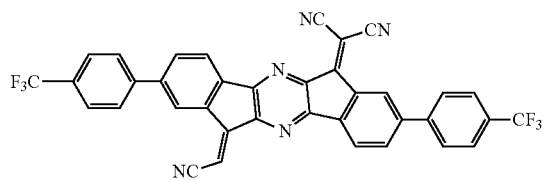
(B-1) 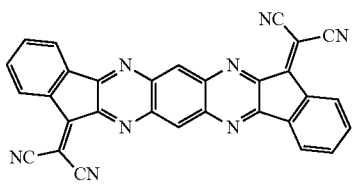
(B-2) 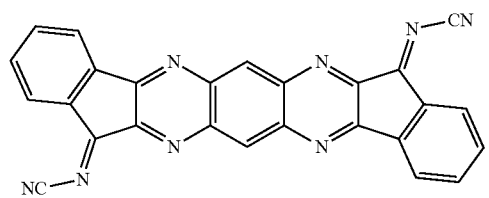
(B-3) 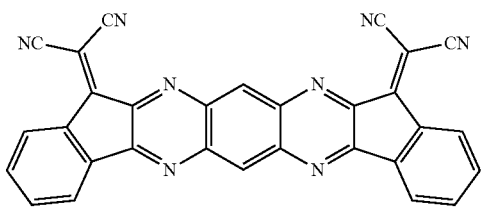
(B-4) 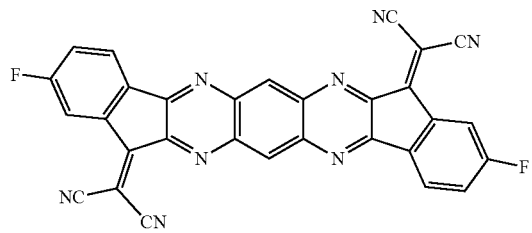
(B-5) 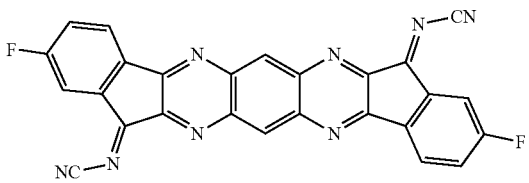
(B-6) 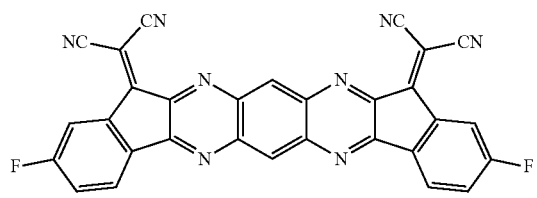
(B-7) 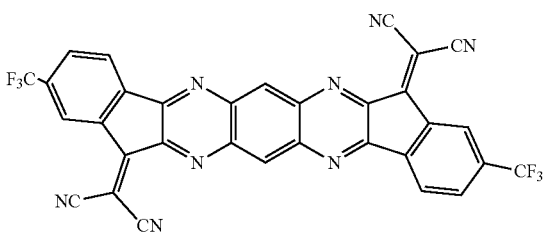
(B-8) 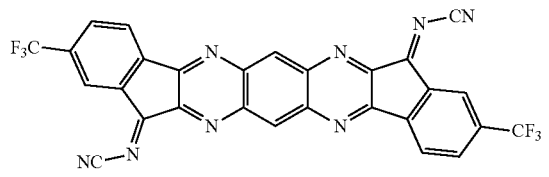
(B-9) 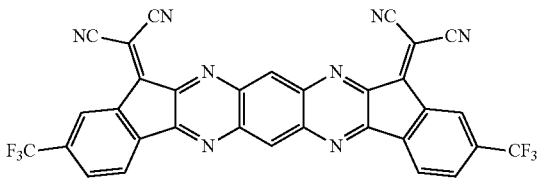
(B-10) 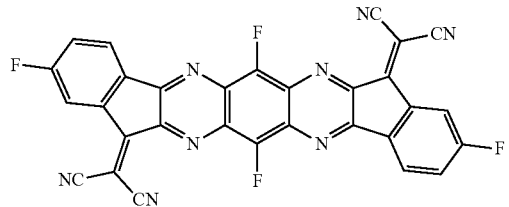

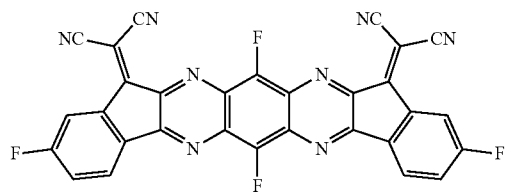
(B-12)
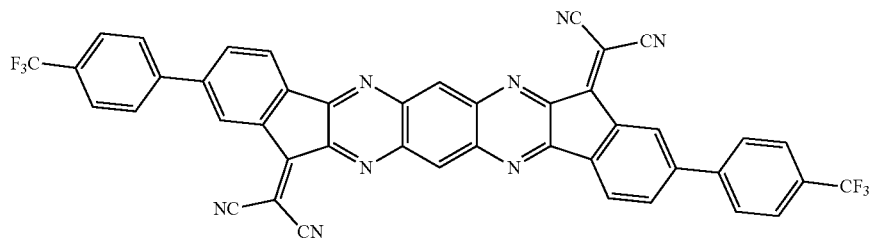
(B-13)
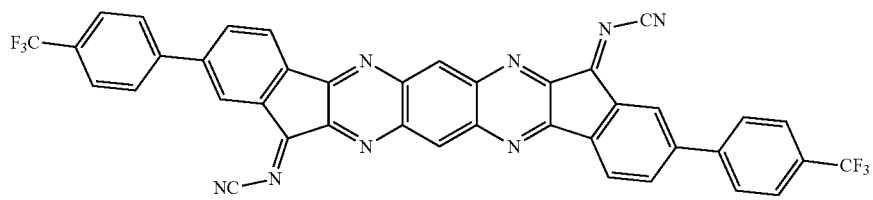
(B-14)
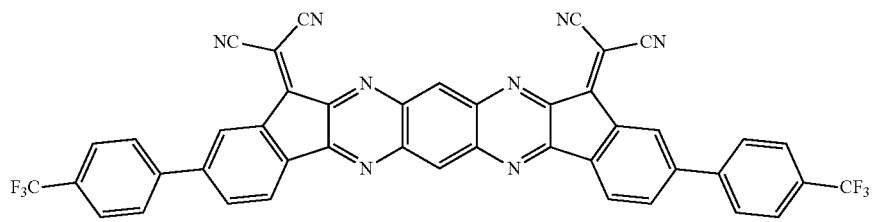
(B-15)
(B-16)
(B-17)
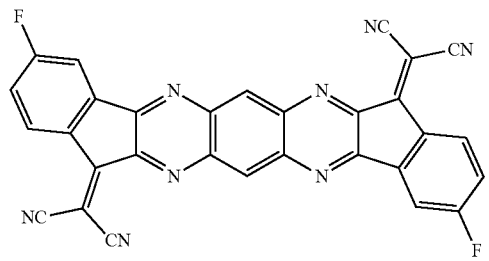
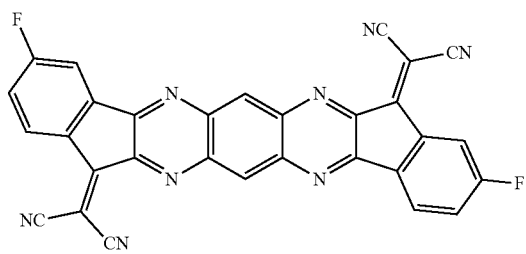
(B-18)
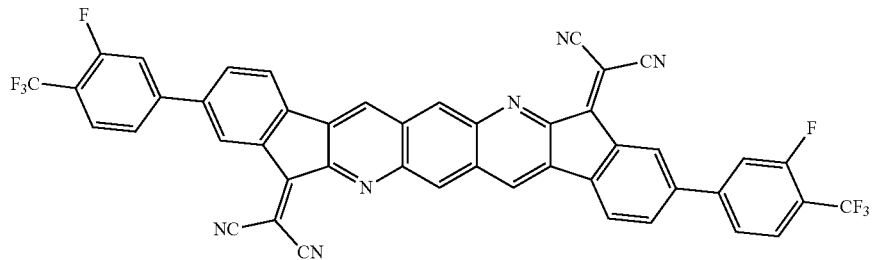

-continued
(B-19)
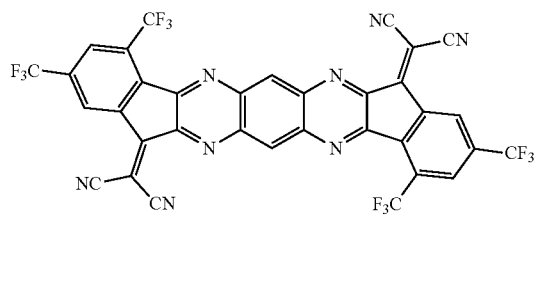
(B-20)
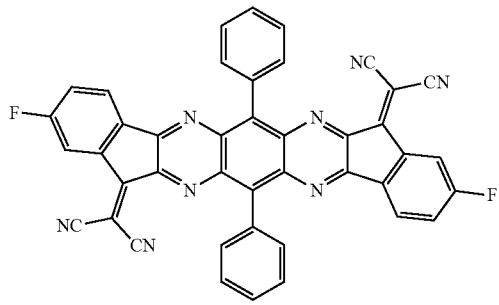
(A'-1)
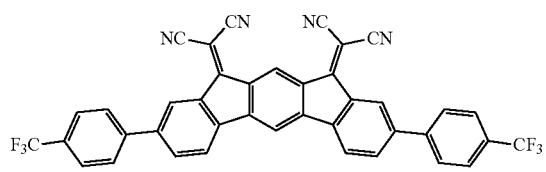
(A'-2)
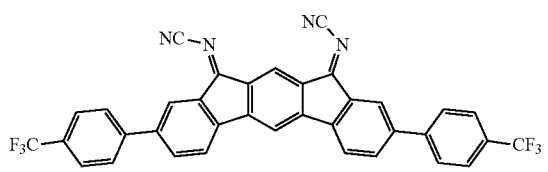
(A'-3)
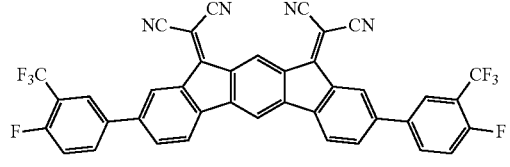
(A'-4)
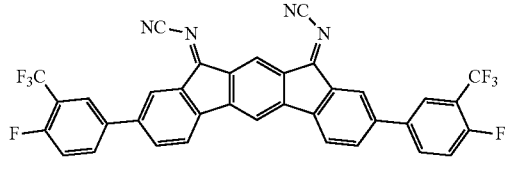
(A'-5)
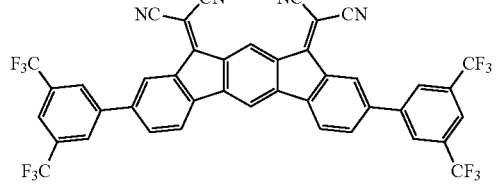
(A'-6)
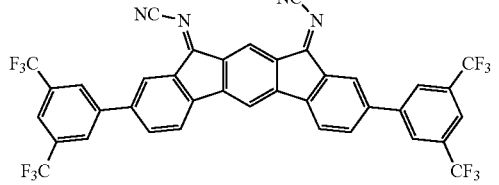
(A'-7)
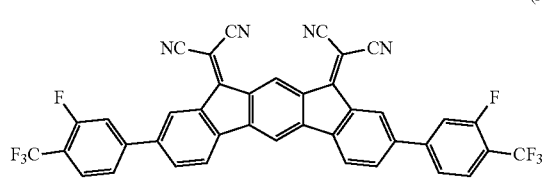
(A'-8)
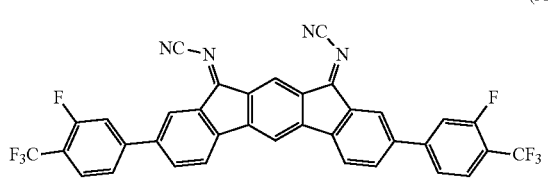
(A'-9)
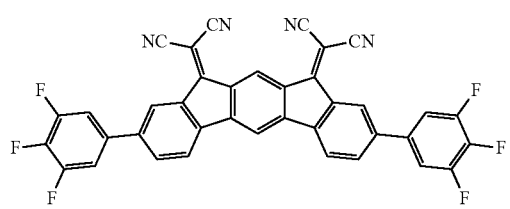
(A'-10)
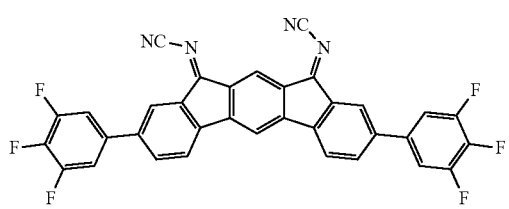
(A'-11)
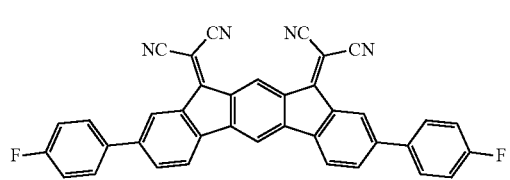
(A'-12)
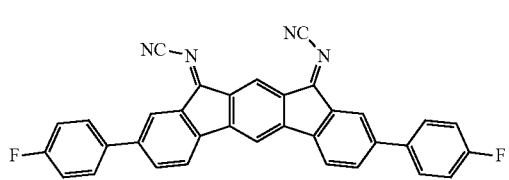

-continued
| | |
|---|---|
| (A'-13) 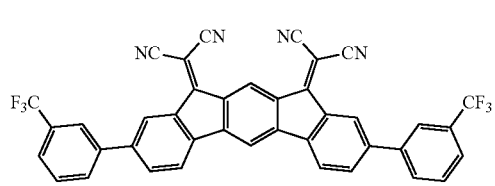 | (A'-14) 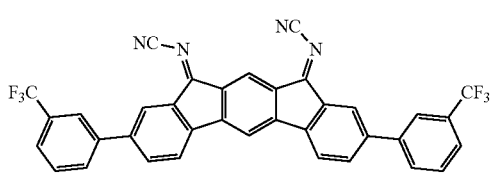 |
| (A'-15) 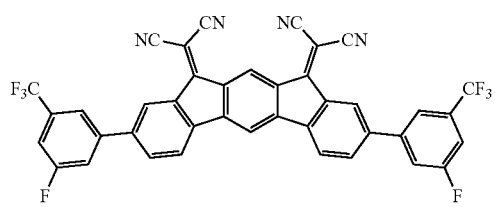 | (A'-16) 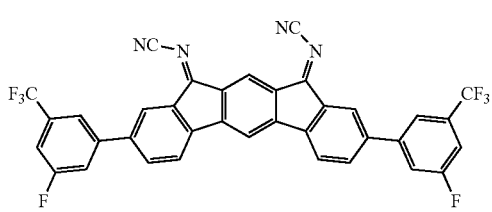 |
| (A'-17) 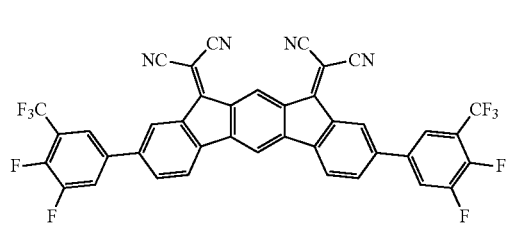 | (A'-18) 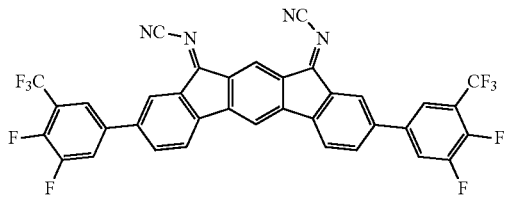 |
| (A'-19) 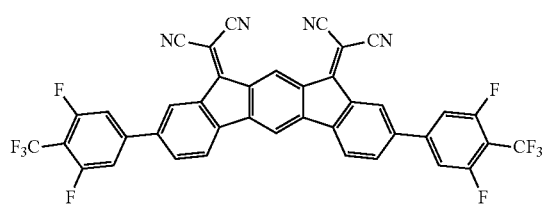 | (A'-20) 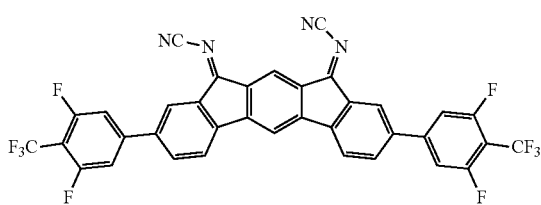 |
| (A'-21) 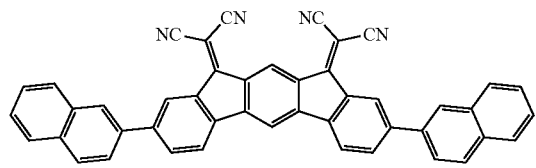 | (A'-22) 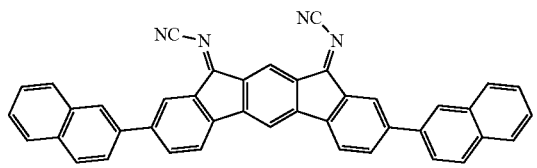 |
| (A'-23) 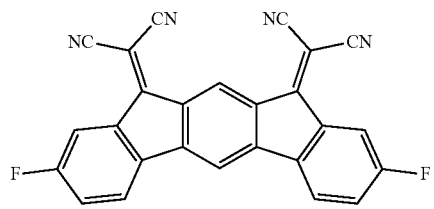 | (A'-24) 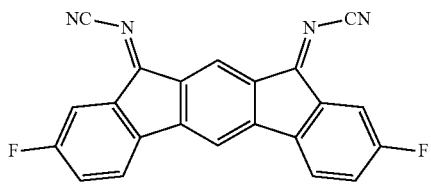 |
| (A'-25) 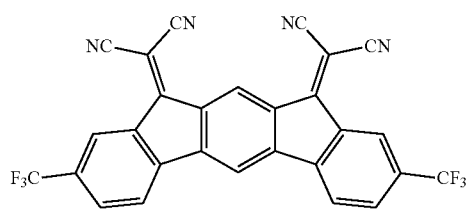 | (A'-26) 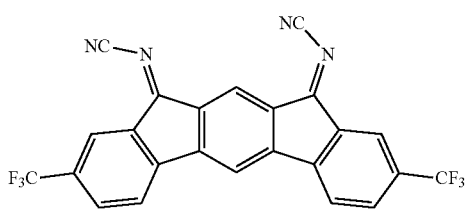 |

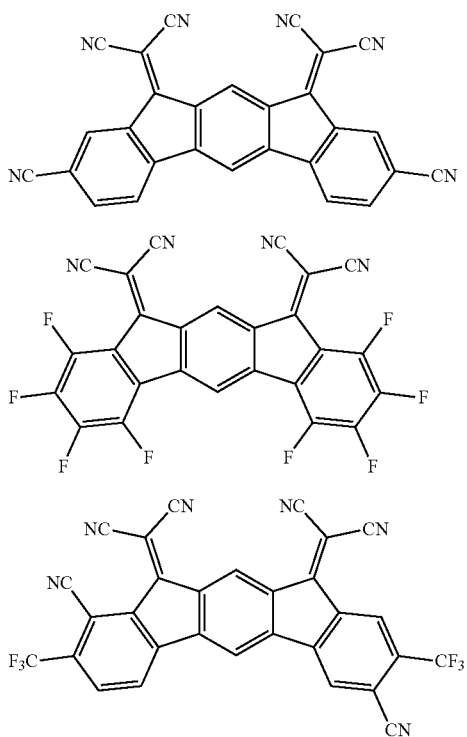
(A'-27)
(A'-29)
(A'-31)

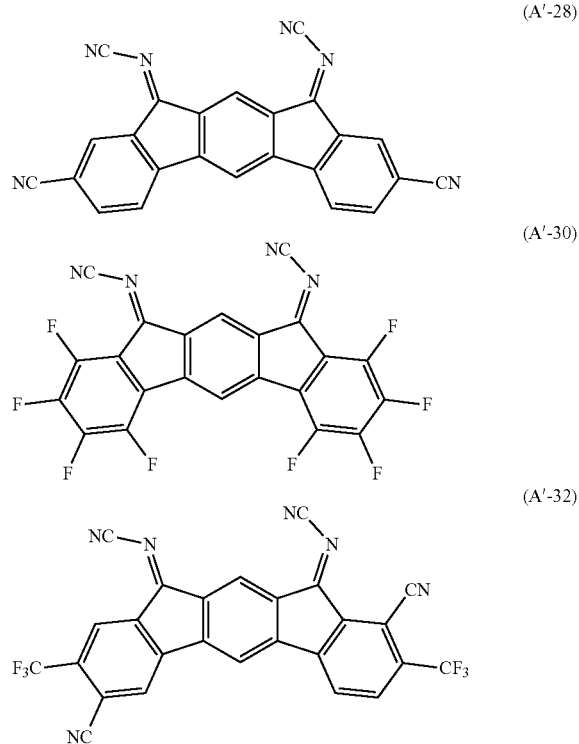
(A'-28)
(A'-30)
(A'-32)

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4$TCNQ (2,3,5,6-Tetrafluoro-7,7,8,8-tetracyanoquinodimethane).

Space Layer

The space layer is a layer, for example, disposed between a fluorescent emitting layer and a phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used as a material for the space layer. To prevent the diffusion of triplet energy in the adjacent phosphorescent emitting layer, the triplet energy of the material for the space layer is preferably 2.6 eV or more. The materials described above with respect to the hole transporting layer are usable as the material for the space layer. The material for organic EL device in an aspect of the invention may be used as the material for the space layer.

Blocking Layer

The organic EL device in an aspect of the invention preferably comprises a blocking layer, such as an electron blocking layer, a hole blocking layer, and a triplet blocking layer, which is disposed adjacent to a light emitting layer. The electron blocking layer is a layer which prevents the diffusion of electrons from a light emitting layer to a hole transporting layer. The hole blocking layer is a layer which prevents the diffusion of holes from a light emitting layer to an electron transporting layer. The material for organic EL device in an aspect of the invention may be used as the material for hole blocking layer.

The triplet blocking layer prevents the diffusion of triplet excitons generated in a light emitting layer to adjacent layers and has a function of confining the triplet excitons within a light emitting layer, thereby preventing the deactivation of energy on a molecule other than the emitting dopant of triplet excitons, for example, on a molecule in an electron transporting layer.

If a phosphorescent device having a triplet blocking layer satisfies the following energy relationship:

$$E^T_d < E^T_{TB}$$

wherein $E^T_d$ is the triplet energy of a phosphorescent dopant in a light emitting layer and $E^T_{TB}$ is the triplet energy of a compound forming the triplet blocking layer,
the triplet excitons of phosphorescent dopant are energetically confined (not move into other molecules). Therefore, the energy deactivation process other than the emission on the phosphorescent dopant may be prevented, thereby enabling the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of the ambient heat energy when a device is operated at around room temperature as generally employed in practical operation. As compared with the fluorescent emission, the phosphorescent emission is likely to be affected by the endothermic diffusion of excitons because the lifetime of triplet excitons is longer. Therefore, as for the energy difference $\Delta E^T$, the larger as compared with the heat energy of room temperature, the better, i.e., the energy difference $\Delta E^T$ is more preferably 0.1 eV or more and particularly preferably 0.2 eV or more. In fluorescent devices, the material for organic EL device in an aspect of the invention is usable as the material for triplet blocking layer of the TTF device described in WO 2010/134350A1.

The electron mobility of the material for the triplet blocking layer is preferably $10^{-6}$ cm$^2$/Vs or more at an electric field strength of 0.04 to 0.5 MV/cm. There are several methods for measuring the electron mobility of organic material, for example, Time of Flight method. In the present invention, the electron mobility is determined by an impedance spectroscopy.

The electron mobility of the electron injecting layer is preferably $10^{-6}$ cm$^2$/Vs or more at an electric field strength of 0.04 to 0.5 MV/cm. Within the above range, the injection of electrons from the cathode to the electron transporting layer is promoted and the injection of electrons to the adjacent blocking layer and the light emitting layer is also promoted, thereby enabling to drive a device at lower voltage.

Each layer of the organic EL device of the invention may be formed by any of known methods such as a vacuum vapor deposition method and a spin coating method, although not particularly limited thereto. The organic thin-film layer comprising the compound of the invention in the organic EL device of the invention is formed by a known method such as a vacuum vapor deposition method, a molecular beam epitaxy method (MBE method) and a coating method using a solution of the compound of the invention in a solvent, for example, a dipping method, a spin coating method, a casting method, a bar coating method and a roll coating method.

The thickness of each organic thin film layer in the organic EL device of the invention is not particularly limited and preferably several nanometers to 1 μm because an excessively small thickness may cause defects, such as pin holes, and an excessively large thickness may require a high applied voltage to reduce the efficiency. The layer comprising the compound of the invention, particularly the light emitting layer, is preferably formed by forming a solution containing the compound of the invention and another material, such as a dopant, into a film.

Examples of the film-forming method include known coating methods, and preferably a spin coating method, a casting method, a microgravure coating method, a gravure coating method, a bar coating method, a roll coating method, a slit coating method, a wire bar coating method, a dip coating method, a spray coating method, a screen printing method, a flexographic printing method, an off-set printing method, an ink-jet printing method, and a nozzle printing method. When a pattern is formed, a screen printing method, a flexographic printing method, an off-set printing method, and an ink-jet printing method are preferred. The film formation by these methods can be made under the conditions well known by a skilled person.

After coating, the solvent is removed by heating (250° C. or below) and drying under vacuum, and the irradiation of light and the high temperature heating exceeding 250° C. for polymerization reaction are not needed. Therefore, the deterioration of the device in its performance due to the irradiation of light and the high temperature heating exceeding 250° C. can be prevented.

The film-forming solution contains at least one compound of the invention and may further contain another material, for example, a hole transporting material, an electron transporting material, a light emitting material, an acceptor material, a solvent, and an additive, such as a stabilizer.

The film-forming solution may contain an additive for controlling the viscosity and/or surface tension, for example, a thickener (a high molecular weight compound, etc.), a viscosity depressant (a low molecular weight compound, etc.) and a surfactant. In addition, an antioxidant not adversely affecting the performance of the organic EL device, for example, a phenol antioxidant and a phosphine antioxidant, may be included so as to improve the storage stability.

The content of the compound of the invention in the film-forming solution is preferably 0.1 to 15% by mass and more preferably 0.5 to 10% by mass based on the total amount of the film-forming solution.

Examples of the high molecular weight compound usable as the thickener include an insulating resin, such as polystyrene, polycarbonate, polyarylate, polyester, polyamide, polyurethane, polysulfone, polymethyl methacrylate, polymethyl acrylate, cellulose, and a copolymer thereof; a photoconductive resin, such as poly-N-vinylcarbazole and polysilane; and an electroconductive resin, such as polythiophene and polypyrrole.

Examples of the solvent for the film-forming solution include a chlorine-containing solvent, such as chloroform, methylene chloride, 1,2-dichloroethane, 1, 1,2-trichloroethane, chlorobenzene, and o-dichlorobenzene; an ether solvent, such as tetrahydrofuran, dioxane, dioxolane, and anisole; an aromatic hydrocarbon solvent, such as toluene and xylene; an aliphatic hydrocarbon solvent, such as cyclohexane, methylcyclohexane, n-pentane, n-hexane, n-heptane, n-octane, n-nonane, and n-decane; a ketone solvent, such as acetone, methyl ethyl ketone, cyclohexanone, benzophenone, and acetophenone; an ester solvent, such as ethyl acetate, butyl acetate, ethyl cellosolve acetate, methyl benzoate, and phenyl acetate; a polyhydric alcohol and its derivatives, such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol; an alcoholic solvent, such as methanol, ethanol, propanol, isopropanol, and cyclohexanol; a sulfoxide solvent, such as dimethyl sulfoxide; and an amide solvent, such as N-methyl-2-pyrrolidone and N,N-dimethylformamide. These solvents may be used alone or in combination of two or more.

Of the above solvents, in view of solubility, uniform film formation, viscosity, etc., preferred are the aromatic hydrocarbon solvent, the ether solvent, the aliphatic hydrocarbon solvent, the ester solvent and the ketone solvent, and more preferred are toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetralin, 1,3-dioxane, 1,4-dioxane, 1,3-dioxolane, anisole, ethoxybenzene, cyclohexane, bicyclohexyl, cyclohexenylcyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexyl ketone, acetophenone, and benzophenone.

The organic electroluminescence device in an aspect of the invention is usable in electronic equipment, for example, as display parts, such as organic EL panel module, display devices of television sets, mobile phones, personal computer, etc., and light emitting sources of lighting equipment and vehicle lighting equipment.

EXAMPLES

The present invention will be described in more detail with reference to the examples. However, it should be noted that the scope of the present invention is not limited thereto.

Synthesis Example (1-1): Synthesis of Intermediate 1

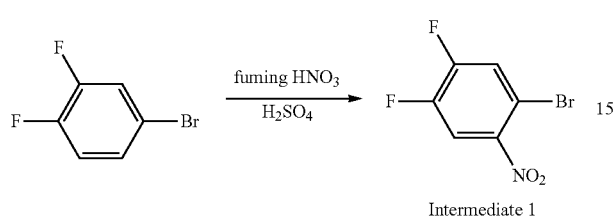

Intermediate 1

Under argon stream, a reaction vessel containing 83 mL of concentrated sulfuric acid was cooled on an ice bath and then 30 g of fuming nitric acid and 17.0 g (88 mmol) of 1-bromo-3,4-difluorobenzene were added. After raising the temperature to 20° C., the mixture was stirred for 2 h.

The reaction solution was poured into an iced water and extracted with methylene chloride. The separated organic layer was washed with an aqueous solution of sodium hydrogencarbonate and a saturated saline and then dried over sodium sulfate. Then, the organic solvent was evaporated off under reduced pressure to obtain 20.3 g (85 mmol) of a product, which was identified as the intermediate 1 by FD-MS (Field Desorption Mass Spectrometry) analysis (yield: 97%).

Synthesis Example (1-2): Synthesis of Intermediate 2

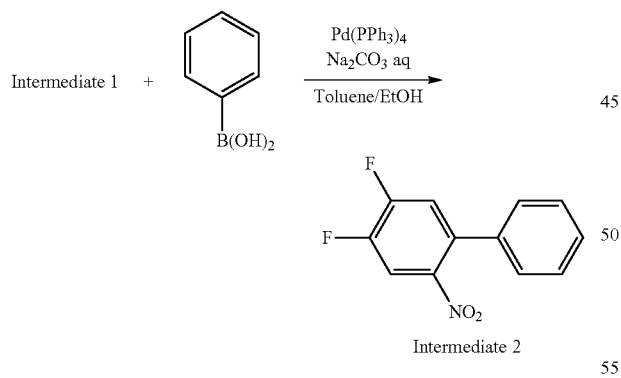

Intermediate 2

Under argon stream, the intermediate 1 (11.9 g, 50 mmol), phenylboronic acid (7.9 g, 65 mmol), tetrakis(triphenylphosphine)palladium (1.73 g, 1.5 mmol), toluene (170 mL), ethanol (30 mL), and a 2 M aqueous solution of sodium carbonate (50 mL) were added to a reaction vessel successively. The obtained mixture was refluxed under heating for 8 h.

After cooling the reaction solution to room temperature, the organic layer was separated and the organic solvent was evaporated off under reduced pressure. The obtained residue was purified by silica gel column chromatography to obtain 11.6 g (49 mmol) of a product, which was identified as the intermediate 2 by FD-MS analysis (yield: 98%).

Synthesis Example (1-3): Synthesis of Intermediate 3

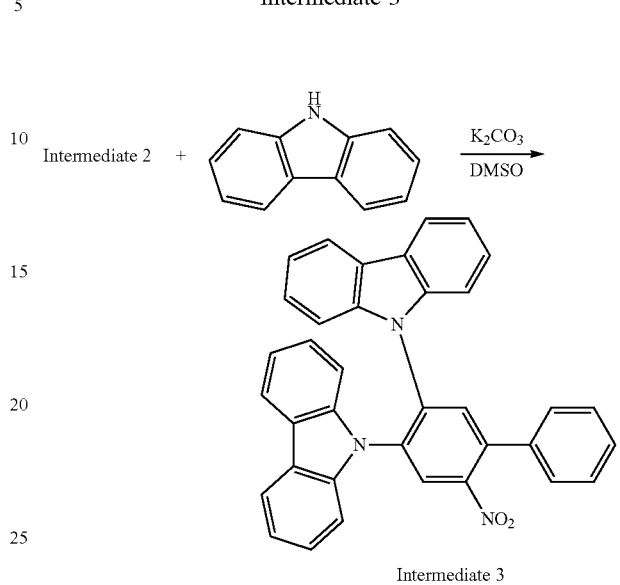

Intermediate 3

Under argon stream, the intermediate 2 (10.0 g, 43 mmol), carbazole (17.3 g, 103 mmol), potassium carbonate (35.7 g, 258 mmol), and dehydrated dimethylsulfoxide (85 mL) were added to a reaction vessel successively. The obtained mixture was stirred at 180° C. for 8 h.

After cooling the reaction solution to room temperature, distilled water and methylene chloride were added. The organic layer was separated and the organic solvent was evaporated off under reduced pressure. The obtained residue was purified by silica gel column chromatography to obtain 8.9 g (17 mmol) of a product, which was identified as the intermediate 3 by FD-MS analysis (yield: 40%).

Synthesis Example (1-4): Synthesis of Intermediate 4

Intermediate 3 $\xrightarrow{\underset{\text{o-Dichlorobenzene}}{PPh_3}}$

Intermediate 4

Under argon stream, the intermediate 3 (8.9 g, 17 mmol), triphenylphosphine (11.2 g, 43 mmol), and o-dichlorobenzene (34 mL) were added to a reaction vessel successively. The obtained mixture was stirred at 180° C. for 6 h.

After cooling to room temperature, the reaction solution was purified by silica gel column chromatography to obtain 5.7 g (11.5 mmol) of a product, which was identified as the intermediate 4 by FD-MS analysis (yield: 67%).

Synthesis of Intermediates 5 to 7

The following intermediates 5 to 7 were synthesized in accordance with the method described in WO 2011/132683.

Intermediate 5

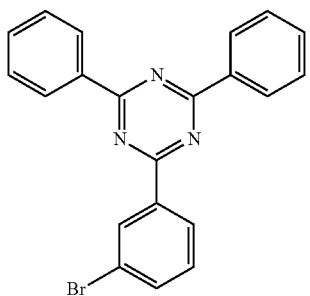

Intermediate 6

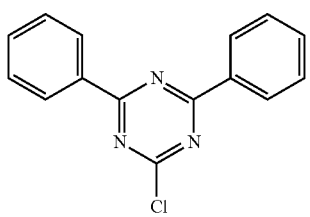

Intermediate 7

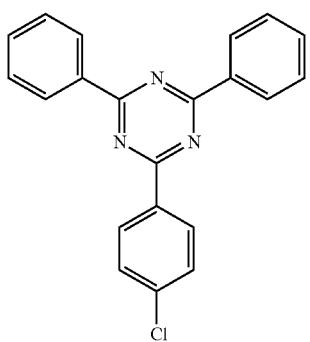

Synthesis Example (1-5): Synthesis of Compound 1

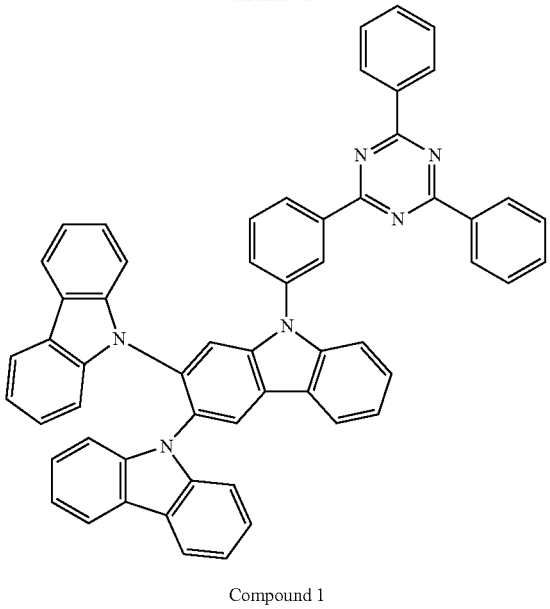

Compound 1

Under argon stream, the intermediate 4 (1.6 g, 3.2 mmol), the intermediate 5 (1.5 g, 3.8 mmol), tris(dibenzylideneacetone)dipalladium (117 mg, 0.13 mmol), tri-tert-butylphosphonium tetrafluoroborate (93 mg, 0.32 mmol), sodium tert-butoxide (615 mg, 6.4 mmol), and dehydrated xylene (16 mL) were added to a reaction vessel successively. The obtained mixture was refluxed for 8 h under heating.

After cooling the reaction solution to room temperature, the organic layer was separated and the organic solvent was evaporated off under reduced pressure. The obtained residue was purified by silica gel column chromatography to obtain 1.9 g (2.4 mmol) of a product, which was identified as the compound 1 by FD-MS analysis (yield: 67%).

The result of FD-MS of the obtained compound is shown below. FDMS: calcd for $C_{57}H_{36}N_6$. found m/z=804 (M+).

Synthesis Example (2-1): Synthesis of Compound 2

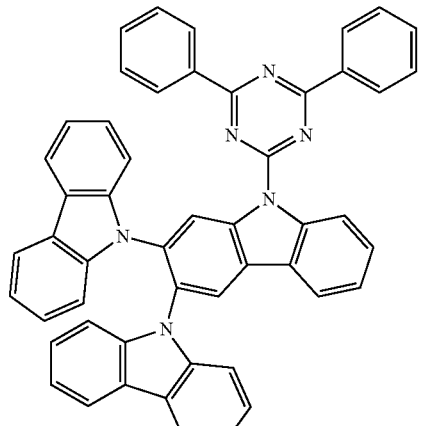

Compound 2

The compound 2 was synthesized in the same manner as in the synthesis of compound 1 except for using the intermediate 6 in place of the intermediate 5.

The result of FD-MS of the obtained compound is shown below. FDMS: calcd for $C_{51}H_{32}N_6$. found m/z=728 (M+).

Synthesis Example (3-1): Synthesis of Compound 3

Intermediate 4 + Intermediate 7 ⟶

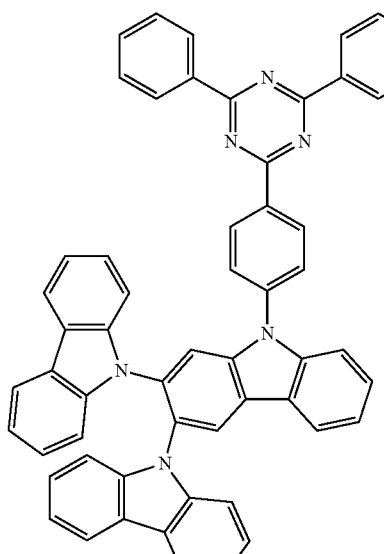

Compound 3

The compound 3 was synthesized in the same manner as in the synthesis of compound 1 except for using the intermediate 7 in place of the intermediate 5.

The result of FD-MS of the obtained compound is shown below. FDMS: calcd for $C_{57}H_{36}N_6$. found m/z=804 (M+).

Synthesis Example (4-1): Synthesis of Intermediate 8

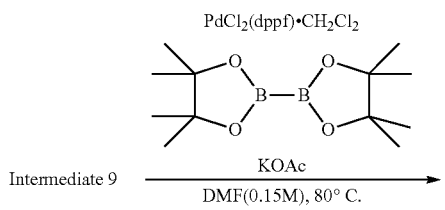

Intermediate 8

The same synthetic procedure as in the synthesis of intermediate 2 was repeated except for using 2,4,6-trichloropyridine in place of the intermediate 1 to obtain a product, which was identified as the intermediate 8 by FD-MS analysis.

Synthesis Example (4-2): Synthesis of Intermediate 9

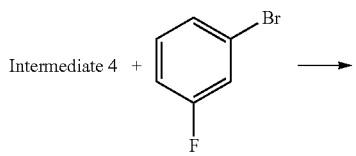

Intermediate 4 +

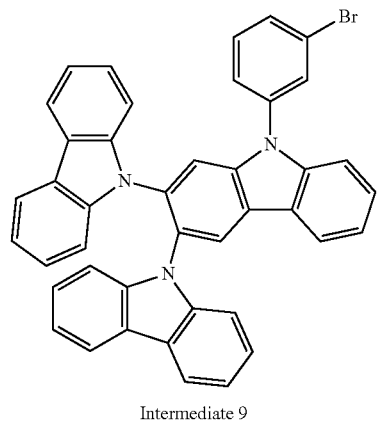

Intermediate 9

The same synthetic procedure as in the synthesis of intermediate 3 was repeated except for using 3-bromofluorobenzene in place of the intermediate 2 and using the intermediate 4 in place of carbazole to obtain a product, which was identified as the intermediate 9 by FD-MS analysis.

Synthesis Example (4-3): Synthesis of Intermediate 10

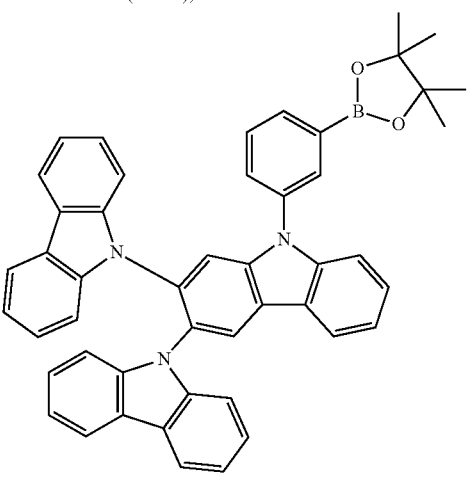

Intermediate 10

Under argon stream, the intermediate 9 (3.3 g, 5 mmol), bis(pinacolato)diboron (1.7 g, 6.6 mmol), [1,1'-bis(diphenylphosphino)ferrocene]palladium(II) dichloride dichloromethane adduct (0.12 g, 0.15 mmol), potassium acetate (1.5 g, 15 mmol), and N,N-dimethylformamide (34 mL) are added to a reaction vessel successively. The obtained mixture was refluxed for 8 h under heating.

After cooling the reaction solution to room temperature, organic layer was separated and the organic solvent was evaporated off under reduced pressure. The obtain residue was purified by silica gel column chromatography to obtain 1.75 g of a product, which was identified as the intermediate 10 by FD-MS analysis (yield: 80%).

Synthesis Example (4-4): Synthesis of Compound 4

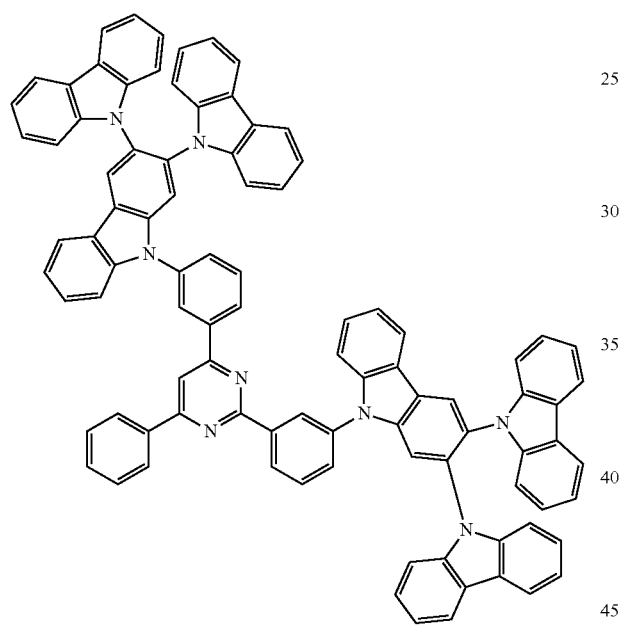

Compound 4

The compound 4 was synthesized in the same manner as in the synthesis of intermediate 2 except for using the intermediate 8 in place of the intermediate 1 and using the intermediate 10 in place of phenylboronic acid.

The result of FD-MS of the obtained compound is shown below. FDMS: calcd for $C_{91}H_{58}N_8$. found m/z=1298 (M+).

Synthesis Example (5-1): Synthesis of Compound 5

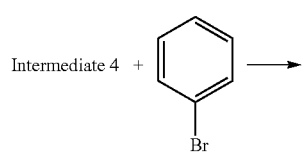

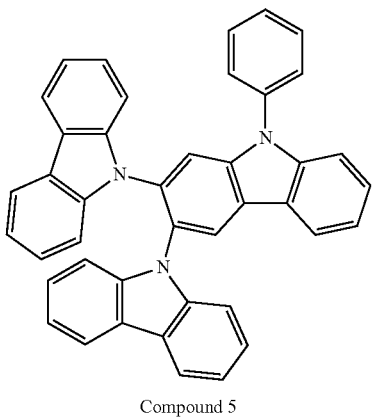

Compound 5

The compound 5 was synthesized in the same manner as in the synthesis of compound 1 except for using bromobenzene in place of the intermediate 5.

The result of FD-MS of the obtained compound is shown below. FDMS: calcd for $C_{42}H_{27}N_3$. found m/z=573 (M+).

Synthesis Example (6-1): Synthesis of Compound 6

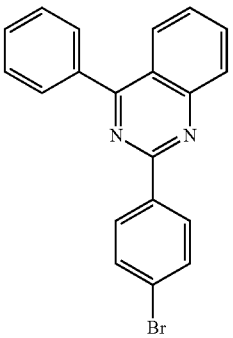

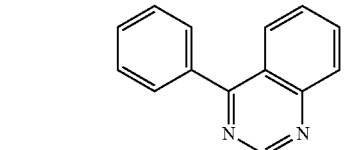

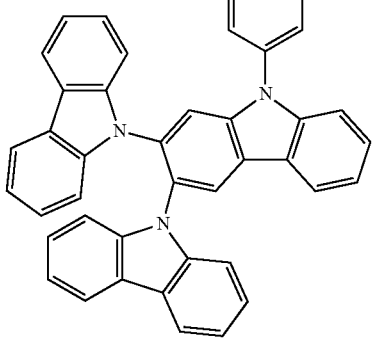

Compound 6

The compound 6 was synthesized in the same manner as in the synthesis of compound 1 except for using 2-(4-bromophenyl)-4-phenylquinazoline in place of the intermediate 5.

The result of FD-MS of the obtained compound is shown below. FDMS: calcd for $C_{56}H_{35}N_5$. found m/z=777 (M+).

Synthesis Example (7-1): Synthesis of Compound 7

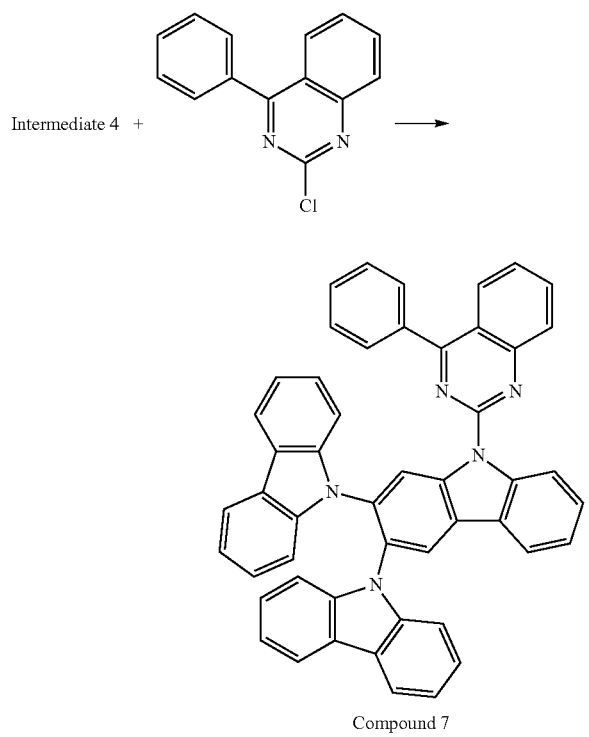

Compound 7

The compound 7 was synthesized in the same manner as in the synthesis of compound 1 except for using 2-chloro-4-phenylquinazoline in place of the intermediate 5.

The result of FD-MS of the obtained compound is shown below. FDMS: calcd for $C_{50}H_{31}N_5$. found m/z=701 (M+).

Synthesis Example (8-1): Synthesis of Compound 8

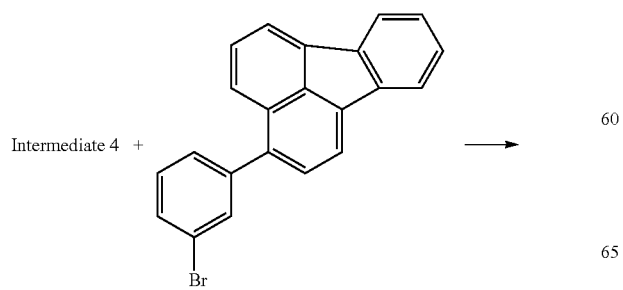

-continued

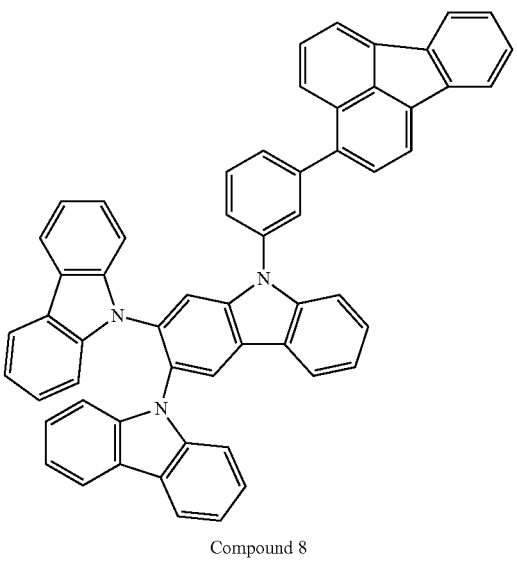

Compound 8

The compound 8 was synthesized in the same manner as in the synthesis of compound 1 except for using 3-(3-bromophenyl)fluoranthene in place of the intermediate 5.

The result of FD-MS of the obtained compound is shown below. FDMS: calcd for $C_{58}H_{35}N_3$. found m/z=773 (M+).

Synthesis Example (9-1): Synthesis of Compound 9

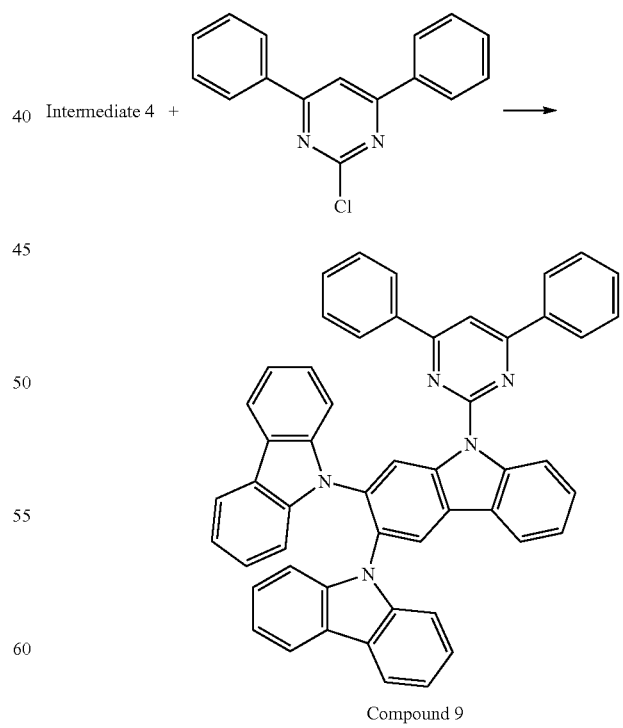

Compound 9

The compound 9 was synthesized in the same manner as in the synthesis of compound 1 except for using 2-chloro-4,6-diphenylpyrimidine in place of the intermediate 5.

The result of FD-MS of the obtained compound is shown below. FDMS: calcd for $C_{52}H_{33}N_5$. found m/z=727 (M+).

Example 1

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min. The thickness of the ITO transparent electrode was 100 nm.

The cleaned glass substrate having an ITO transparent electrode line was mounted to a substrate holder of a vacuum vapor deposition apparatus. The compound HA1 was vapor-deposited so as to cover the ITO transparent electrode to form a film HA1 with a thickness of 10 nm, thereby forming a hole injecting layer.

On the hole injecting layer, the compound HT1 as a first hole transporting material was vapor-deposited to form a first hole transporting layer with a thickness of 40 nm. Successively after forming the first hole transporting layer, the compound HT2 as a second hole transporting material was vapor-deposited to form a second hole transporting layer with a thickness of 10 nm.

On the second hole transporting layer, the above compound 1 as a host material and the compound YD1 as a phosphorescent emitting material were vapor co-deposited to form a phosphorescent emitting layer with a thickness of 20 nm. The concentration of the compound YD1 in the light emitting layer was 12% by mass. The co-deposited film works as a light emitting layer.

Successively after forming the light emitting layer, the compound ET1 was vapor-deposited into a film with a thickness of 45 nm. The compound ET1 film works as a first electron transporting layer.

Then, LiF was vapor-deposited into a film with a thickness of 1 nm at a film-forming speed of 0.1 Å/sec to form an electron injecting electrode (cathode). On the LiF film, metallic Al was vapor-deposited to form a metallic cathode with a thickness of 80 nm, thereby obtaining an organic EL device.

The compounds used in the examples and the comparative examples are shown below.

HA1
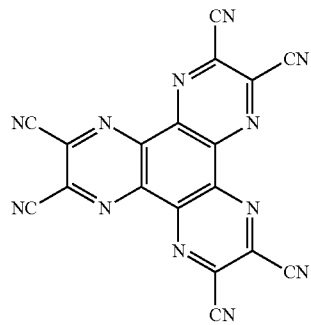

HT1
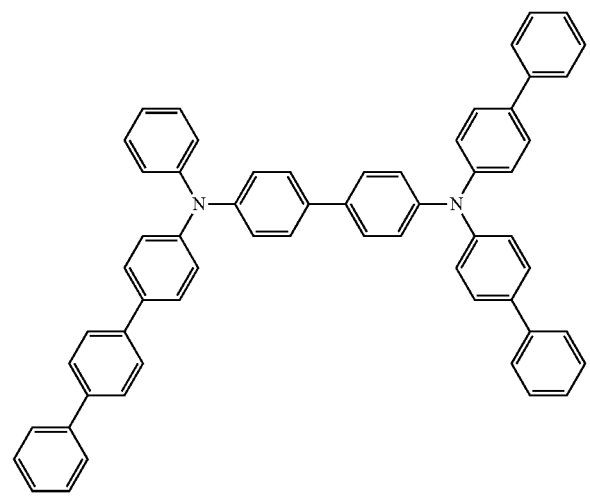

HT2
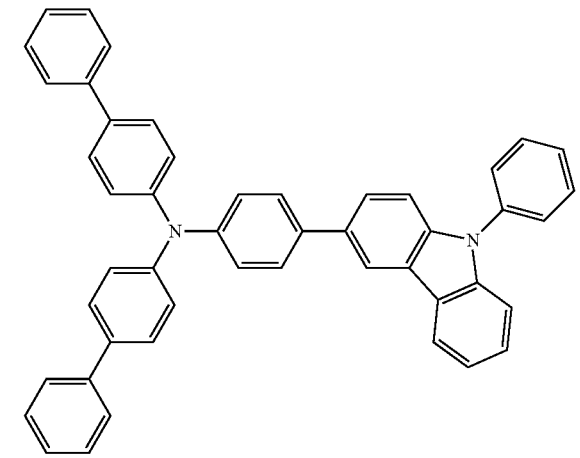

ET1
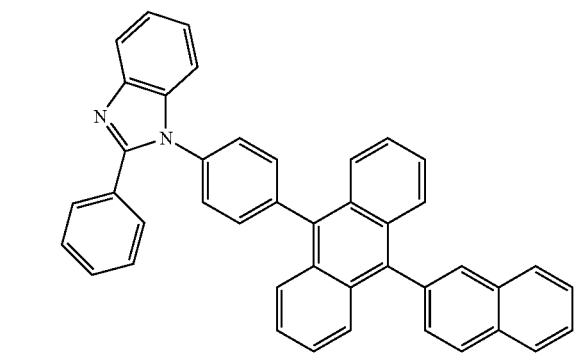

YD1
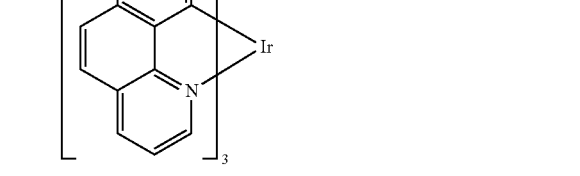

The organic EL device thus produced was measured for the 80% lifetime (time taken until the luminance was reduced to 80% of the initial luminance when operated at a constant current drive) at an initial luminance of 10000 cd/m$^2$.

Examples 2 to 3

Each organic EL device was produced in the same manner as in Example 1 except for using the compound 2 or 3 as the host material of the phosphorescent emitting layer in place of the compound 1. The evaluation results obtained in the same manner as in Example 1 are shown in Table 1.

Comparative Example 1

An organic EL device was produced in the same manner as in Example 1 except for using the following comparative compound 1 as the host material of the phosphorescent emitting layer in place of the compound 1. The evaluation result obtained in the same manner as in Example 1 is shown in Table 1.

Comparative Compound 1

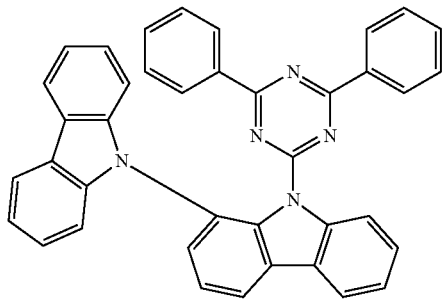

Example 4

An organic EL device was produced in the same manner as in Example 1 except for forming a phosphorescent emitting layer with 20 nm thick by co-vapor depositing the host material (the compound 1 and the compound PG1) and the phosphorescent emitting material (the compound YD1). The evaluation result obtained in the same manner as in Example 1 is shown in Table 1.

The concentration in the light emitting layer was 44% by mass for the compound PG1 and 12% by mass for the compound YD1.

PG1

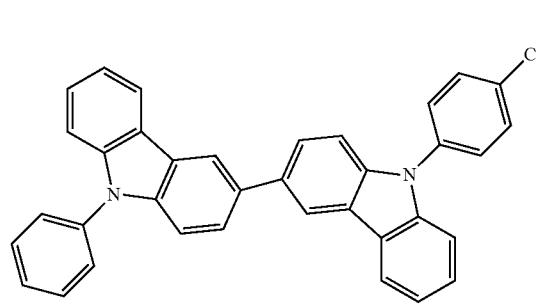

Example 5

An organic EL device was produced in the same manner as in Example 4 except for using the compound 2 as the host material of the phosphorescent emitting layer in place of the compound 1. The evaluation results obtained in the same manner as in Example 1 are shown in Table 1.

Comparative Example 2

An organic EL device was produced in the same manner as in Example 4 except for using the comparative compound 1 as the host material of the phosphorescent emitting layer in place of the compound 1. The evaluation results obtained in the same manner as in Example 1 are shown in Table 1.

Example 6

An organic EL device was produced in the same manner as in Example 1 except for changing the thickness of the first hole transporting layer to 20 nm, forming a phosphorescent emitting layer with 40 nm thick by co-vapor depositing the compound 6 (host material) and the compound RD1 (phosphorescent emitting material), and changing the thickness of the first electron transporting layer to 40 nm. The concentration of the compound RD1 in the light emitting layer was 5% by mass. The evaluation results obtained in the same manner as in Example 1 are shown in Table 1.

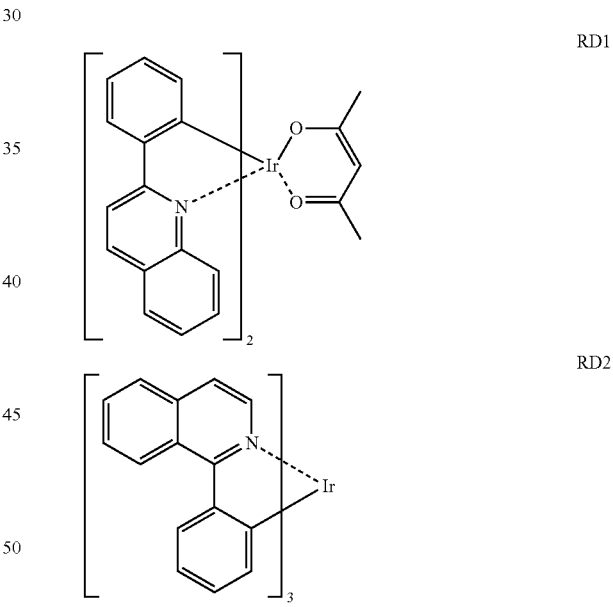

Example 7

An organic EL device was produced in the same manner as in Example 6 except for using the compound 7 as the host material of the phosphorescent emitting layer in place of the compound 6. The evaluation results obtained in the same manner as in Example 1 are shown in Table 1.

Example 8

An organic EL device was produced in the same manner as in Example 6 except for using the compound 8 as the host material of the phosphorescent emitting layer and using the compound RD2 as the phosphorescent emitting material. The evaluation results obtained in the same manner as in Example 1 are shown in Table 1.

Comparative Example 3

An organic EL device was produced in the same manner as in Example 6 except for using the comparative compound 1 as the host material of the phosphorescent emitting layer in place of the compound 6. The evaluation results obtained in the same manner as in Example 1 are shown in Table 1.

Comparative Example 4

An organic EL device was produced in the same manner as in Example 8 except for using the comparative compound 1 as the host material of the phosphorescent emitting layer in place of the compound 8. The evaluation results obtained in the same manner as in Example 1 are shown in Table 1.

TABLE 1

|  | Host material in light emitting layer | 80% lifetime (h) |
| --- | --- | --- |
| Example 1 | Compound 1 | 700 |
| Example 2 | Compound 2 | 600 |
| Example 3 | Compound 3 | 600 |
| Comparative Example 1 | Comparative Compound 1 | 300 |
| Example 4 | Compound 1 | 800 |
| Example 5 | Compound 2 | 700 |
| Comparative Example 2 | Comparative Compound 1 | 350 |
| Example 6 | Compound 6 | 600 |
| Example 7 | Compound 7 | 800 |
| Example 8 | Compound 8 | 800 |
| Comparative Example 3 | Comparative Compound 1 | 200 |
| Comparative Example 4 | Comparative Compound 1 | 200 |

Upon comparing the examples 1 to 5 with the comparative example 1 to 2 and comparing the examples 6 to 8 with the comparative examples 3 to 4, it can be found that the organic EL devices employing the carbazole derivative of an embodiment of the present invention have the lifetimes longer than those of the organic EL devices employing the comparative compound 1.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

What is claimed is:

1. A carbazole derivative represented by formula (1):

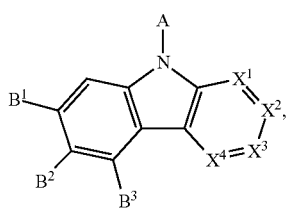

(1)

wherein:
A represents a substituted or unsubstituted aryl group having 6 to 60 ring carbon atoms;
$X^1$ represents N or CH;
$X^2$ to $X^4$ each represent N or CR;
R and $B^3$ each independently represent a hydrogen atom or a substituent, wherein adjacent substituents may be bonded to each other to form a saturated or unsaturated ring structure and when more than one R occurs, groups R may be the same or different; and
at least $B^1$ and $B^2$ are represented by formula (2):

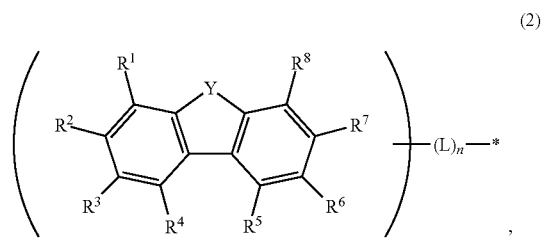

(2)

wherein
* represents a bonding site of $B^1$ and $B^2$ to the carbon atom shown in formula (1);
n is an integer of 0 to 4;
L represents a substituted or unsubstituted arylene group having 6 to 60 ring carbon atoms, a substituted or unsubstituted heteroarylene group having 5 to 60 ring atoms, or a substituted or unsubstituted alkylene group having 1 to 50 carbon atoms;
Y represents NZ;
$R^2$ to $R^7$ and Z each independently represent a single bond, a hydrogen atom or a substituent, wherein adjacent substituents may be bonded to each other to form a saturated or unsaturated ring structure;
$R^1$ and $R^8$ are hydrogen atoms; and
one selected from $R^1$ to $R^8$, Z, R', and R'' represents a single bond which bonds to L, wherein when n is 0, formula (2) bonds to formula (1) via a single bond, and when n is 2 or more, groups L may be the same or different and may be bonded to each other to form a saturated or unsaturated ring structure.

2. A carbazole derivative represented by formula (1):

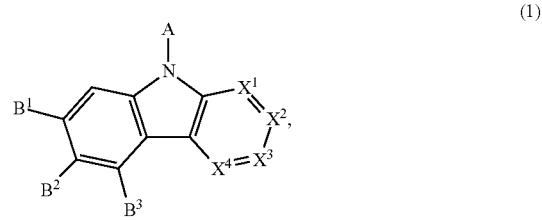

(1)

wherein:
A represents a substituted or unsubstituted aryl group having 6 to 60 ring carbon atoms or a substituted or unsubstituted heteroaryl group having 5 to 60 ring atoms;
$X^1$ represents N or CH;
$X^2$ to $X^4$ each represent N or CR;
R and $B^1$ to $B^3$ each independently represent a hydrogen atom or a substituent, wherein adjacent substituents may be bonded to each other to form a saturated or unsaturated ring structure and when more than one R occurs, groups R may be the same or different; and at least two selected from $B^1$ to $B^3$ are represented by formula (2-2):

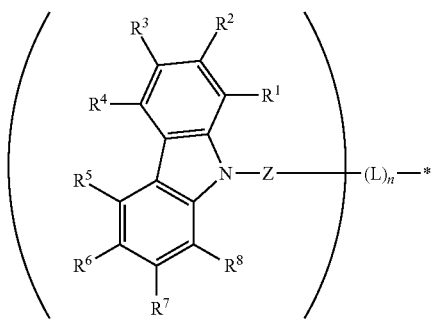

(2-2)

wherein

* represents a bonding site of $B^1$ to $B^3$ to the carbon atom shown in formula (1);

n is an integer of 0 to 4;

L represents a substituted or unsubstituted arylene group having 6 to 60 ring carbon atoms, a substituted or unsubstituted heteroarylene group having 5 to 60 ring atoms, or a substituted or unsubstituted alkylene group having 1 to 50 carbon atoms;

$R^2$ to $R^7$ and Z each independently represent a single bond, a hydrogen atom or a substituent, wherein adjacent substituents may be bonded to each other to form a saturated or unsaturated ring structure;

$R^1$ and $R^8$ are hydrogen atoms; and one selected from $R^2$ to $R^7$ and Z represents a single bond which bonds to L, wherein when n is 0, formula (2) bonds to formula (1) via a single bond, and when n is 2 or more, groups L may be the same or different and may be bonded to each other to form a saturated or unsaturated ring structure.

3. The carbazole derivative according to claim 1, wherein formula (2) is represented by formula (2-3):

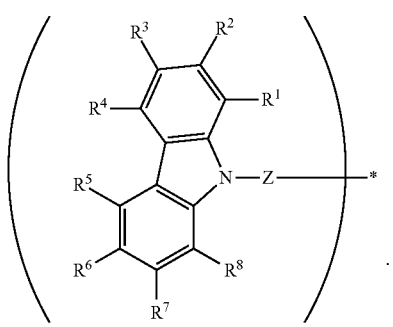

(2-3)

4. The carbazole derivative according to claim 1, wherein the carbazole derivative is represented by formula (3):

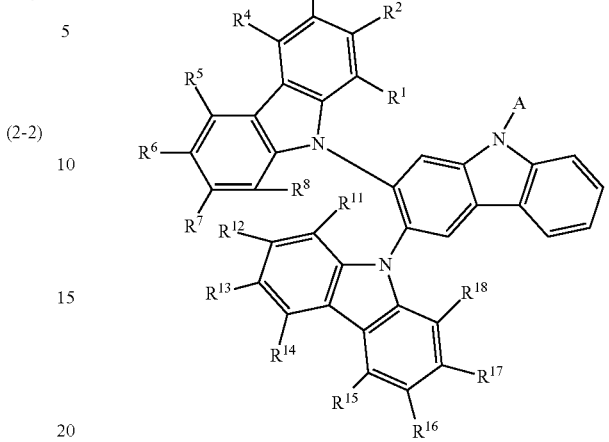

(3)

wherein $R^{11}$ to $R^{18}$ are the same as $R^1$ to $R^8$, respectively.

5. The carbazole derivative according to claim 1, wherein the carbazole derivative is represented by formula (5):

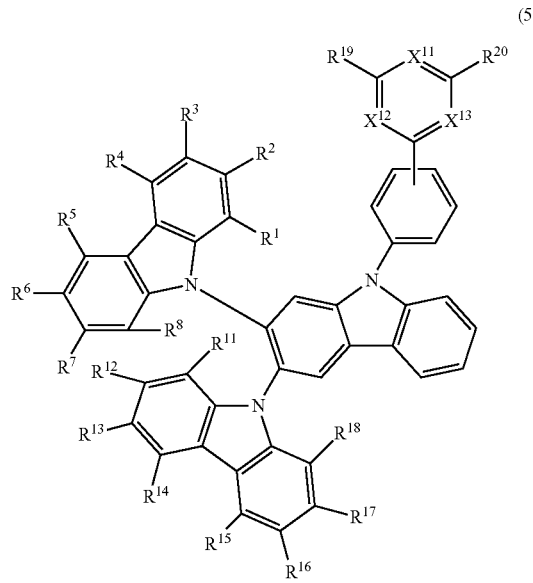

(5)

wherein:

$X^{11}$ to $X^{13}$ each independently represent $CR^{51}$ or N, provided that at least one selected from $X^{11}$ to $X^{13}$ represents N; and $R^{11}$ to $R^{18}$ are the same as defined above with respect to $R^1$ to $R^8$, and $R^{19}$ to $R^{20}$ and $R^{51}$ each independently represent a hydrogen atom or a substituent.

6. The carbazole derivative according to claim 1, wherein the substituent represented by R, $B^3$, $R^2$ to $R^7$ and Z is selected from the group consisting of a substituted or unsubstituted alkyl group having 1 to 50 carbon atoms; a substituted or unsubstituted cycloalkyl group having 3 to 50 ring carbon atoms; a substituted or unsubstituted aryl group having 6 to 60 ring carbon atoms; a substituted or unsubstituted aralkyl group having 7 to 61 carbon atoms; an amino group; a mono- or disubstituted amino group having a substituent selected from a substituted or unsubstituted alkyl group having 1 to 50 carbon atoms and a substituted or unsubstituted aryl group having 6 to 60 ring carbon atoms; a substituted or unsubstituted alkoxy group having 1 to 50 carbon atoms; a substituted or unsubstituted aryloxy group having 6 to 60 ring carbon atoms; a substituted or unsubstituted alkylthio group having 1 to 50 carbon atoms; a substituted or unsubstituted arylthio group having 6 to 60 ring carbon atoms; a mono-, di-, or trisubstituted silyl group having a substituent selected from a substituted or unsubstituted alkyl group having 1 to 50 carbon atoms and a substituted or unsubstituted aryl group having 6 to 60 ring carbon atom; a substituted or unsubstituted heteroaryl group having 5 to 60 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 60 ring carbon atoms; a disubstituted phosphoryl group having a substituent selected from a substituted or unsubstituted alkyl group having 1 to 50 carbon atoms and a substituted or unsubstituted aryl group having 6 to 60 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl- or aryl-substituted carbonyl group; a carboxyl group; a vinyl group; a (meth)acryloyl group; an epoxy group; and an oxetanyl group.

7. The carbazole derivative according to claim 1, wherein the substituent represented by R, $B^1$ to $B^3$, $R^1$ to $R^8$, Z, R', and R" is selected from the group consisting of a substituted or unsubstituted phenyl group; a substituted or unsubstituted biphenylyl group; a substituted or unsubstituted terphenylyl group; a substituted or unsubstituted naphthyl group; a substituted or unsubstituted phenanthryl group; a substituted or unsubstituted fluorenyl group; a substituted or unsubstituted 9,9'-spirobifluorenyl group; a substituted or unsubstituted chrysenyl group; a substituted or unsubstituted triphenylenyl group; a substituted or unsubstituted 9,9-dimethylfluorenyl group; a substituted or unsubstituted 9,9-diphenylfluorenyl group; a substituted or unsubstituted pyridyl group; a substituted or unsubstituted pyrimidinyl group; a substituted or unsubstituted triazinyl group; a substituted or unsubstituted benzofuranyl group; a substituted or unsubstituted isobenzofuranyl group; a substituted or unsubstituted quinolyl group; a substituted or unsubstituted isoquinolyl group; a substituted or unsubstituted quinazolinyl group; a substituted or unsubstituted benzothiophenyl group; a substituted or unsubstituted isobenzothiophenyl group; a substituted or unsubstituted indolizinyl group; a substituted or unsubstituted dibenzofuranyl group; a substituted or unsubstituted dibenzothiophenyl group; a substituted or unsubstituted carbazolyl group; a substituted or unsubstituted azatriphenylenyl group; a substituted or unsubstituted diazatriphenylenyl group; a substituted or unsubstituted xanthenyl group; a substituted or unsubstituted azacarbazolyl group; a substituted or unsubstituted azadibenzofuranyl group; and a substituted or unsubstituted azadibenzothiophenyl group.

8. A material for organic electroluminescence devices, which comprises the carbazole derivative according to claim 1.

9. An organic electroluminescence device which comprises an organic thin film layer between a cathode and an anode, wherein the organic thin film layer comprises one or more layers which comprise a light emitting layer and at least one layer of the organic thin film layer comprises the carbazole derivative according to claim 1.

10. The organic electroluminescence device according to claim 9, wherein the light emitting layer comprises the carbazole derivative.

11. The organic electroluminescence device according to claim 9, wherein the organic electroluminescence device comprises a first charge transporting layer between the anode and the light emitting layer and the first charge transporting layer comprises the carbazole derivative.

12. The organic electroluminescence device according to claim 9, wherein the organic electroluminescence device comprises a second charge transporting layer between the cathode and the light emitting layer and the second charge transporting layer comprises the carbazole derivative.

13. The organic electroluminescence device according to claim 9, wherein the light emitting layer comprises a phosphorescent emitting material.

14. The organic electroluminescence device according to claim 9, wherein the light emitting layer comprises a fluorescent emitting material.

15. The organic electroluminescence device according to claim 13, wherein the phosphorescent emitting material is an ortho-metallated complex comprising a metal selected from iridium (Ir), osmium (Os), and platinum (Pt).

16. The organic electroluminescence device according to claim 15, wherein the phosphorescent emitting material is a complex represented by formula (X):

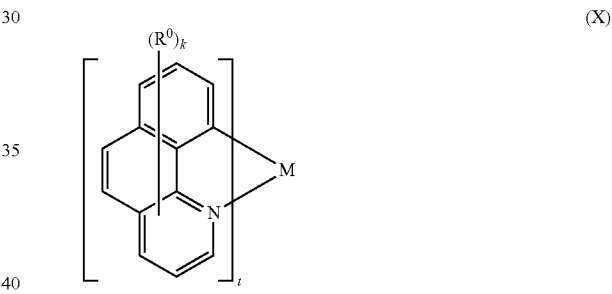

wherein each $R^0$ independently represents a hydrogen atom or a substituent, k is an integer of 1 to 8, t is an integer of 2 to 4, and M is Ir, Os, or Pt.

17. An electronic equipment, comprising the organic electroluminescence device according to claim 9.

18. A carbazole derivative represented by formula (10):

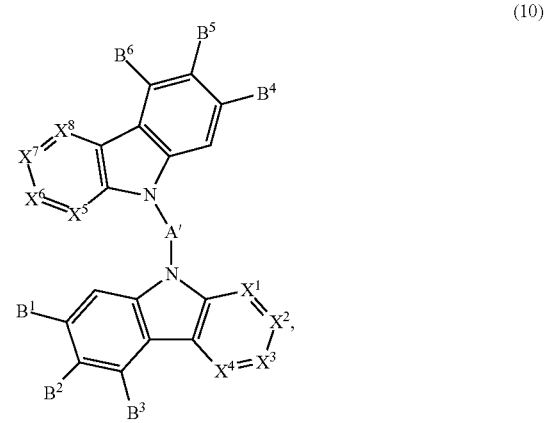

wherein:
A' represents a substituted or unsubstituted arylene group having 6 to 60 ring carbon atoms or a substituted or unsubstituted heteroarylene group having 5 to 60 ring atoms;
$X^1$ and $X^5$ each represent N or CH;
$X^2$ to $X^4$ and $X^6$ to $X^8$ each represent N or CR;
R and $B^1$ to $B^6$ each independently represent a hydrogen atom or a substituent, wherein adjacent substituents may be bonded to each other to form a saturated or unsaturated ring structure and when more than one R occurs, groups R may be the same or different; and
at least two selected from $B^1$ to $B^3$ are represented by formula (2):

(2)

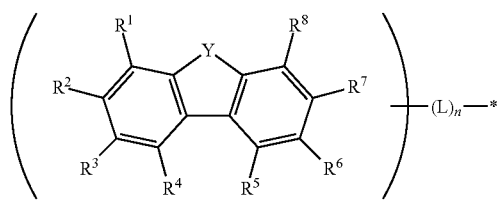

wherein:
* represents a bonding site of $B^1$ to $B^3$ to the carbon atom shown in formula (10);
n is an integer of 0 to 4;
L represents a substituted or unsubstituted arylene group having 6 to 60 ring carbon atoms, a substituted or unsubstituted heteroarylene group having 5 to 60 ring atoms, or a substituted or unsubstituted alkylene group having 1 to 50 carbon atoms;
Y represents NZ, O, S, or CR'R";
$R^1$ to $R^8$, Z, R', and R" each independently represent a single bond, a hydrogen atom or a substituent, wherein adjacent substituents may be bonded to each other to form a saturated or unsaturated ring structure;
provided that when Y is NZ, $R^1$ and $R^8$ are hydrogen atoms; and
one selected from $R^1$ to $R^8$, Z, R', and R" represents a single bond which bonds to L, wherein when n is 0, formula (2) bonds to formula (10) via a single bond, and when n is 2 or more, groups L may be the same or different and may be bonded to each other to form a saturated or unsaturated ring structure.

19. The carbazole derivative according to claim 18, wherein two of $B^1$ to $B^3$ are represented by formula (2).

20. The carbazole derivative according to claim 18, wherein $B^1$ and $B^2$ are represented by formula (2).

21. The carbazole derivative according to claim 18, wherein formula (2) is represented by formula (2-1):

(2-1)

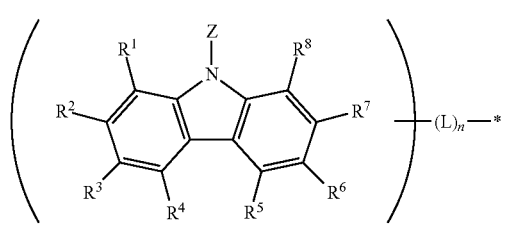

22. The carbazole derivative according to claim 18, wherein formula (2) is represented by formula (2-2):

(2-2)

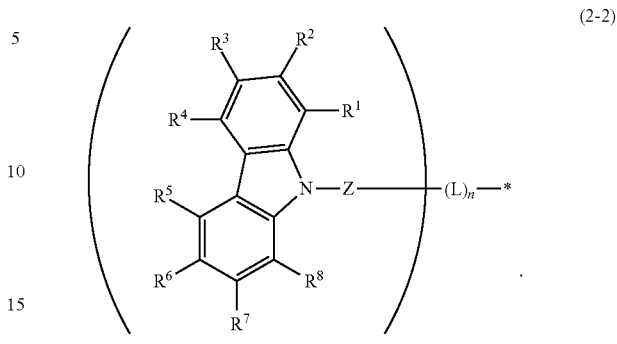

23. The carbazole derivative according to claim 18, wherein formula (2) is represented by formula (2-3):

(2-3)

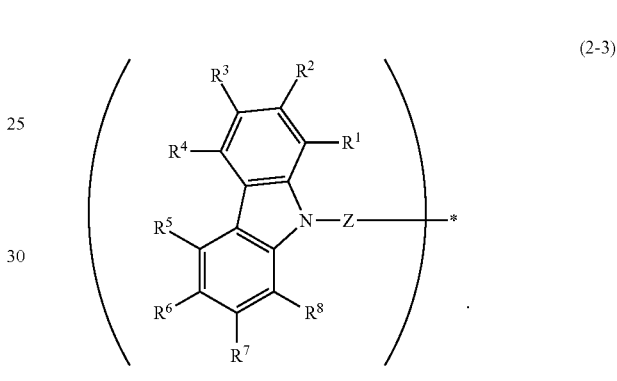

24. The carbazole derivative according to claim 18, wherein the carbazole derivative is represented by formula (11):

(11)

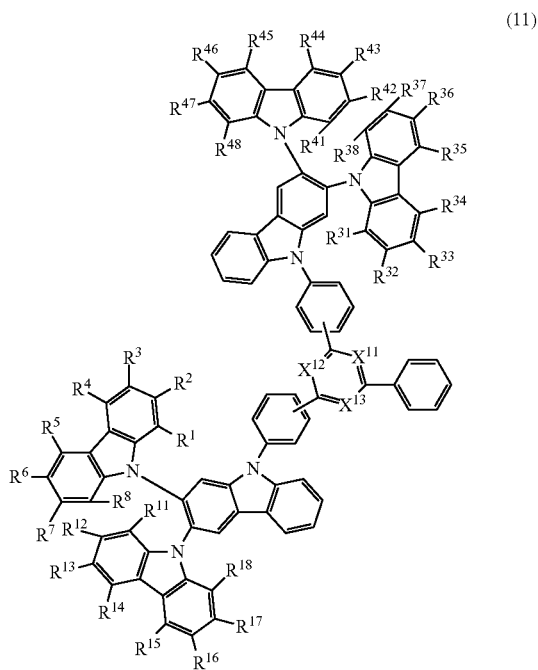

wherein:

$X^{11}$ to $X^{13}$ each independently represent $CR^{51}$ or N;

$R^{31}$ to $R^{38}$ and $R^{41}$ to $R^{48}$ are the same as defined above with respect to $R^1$ to $R^8$; and $R^{51}$ represents a hydrogen atom or a substituent, when more than one $R^{51}$ occurs, groups $R^{51}$ may be the same or different.

* * * * *